United States Patent [19]

Althuis et al.

[11] 4,044,134

[45] Aug. 23, 1977

[54] FUSED PYRIMIDIN-4(3H)-ONES AS ANTIALLERGY AGENTS

[75] Inventors: Thomas H. Althuis, Groton; Leonard J. Czuba, New London; Hans-Jurgen E. Hess, Old Lyme; Saul B. Kadin, New London, all of Conn.

[73] Assignee: Pfizer Inc., New York, N.Y.

[21] Appl. No.: 667,515

[22] Filed: Mar. 16, 1976

Related U.S. Application Data

[60] Division of Ser. No. 485,945, July 5, 1974, Pat. No. 3,974,161, which is a continuation-in-part of Ser. No. 444,138, Feb. 20, 1974, abandoned, which is a continuation-in-part of Ser. No. 351,025, April 13, 1973, abandoned.

[51] Int. Cl.² .......................................... A61K 31/505
[52] U.S. Cl. ............................... 424/251; 260/465 D; 260/295.5 A; 260/294.9; 260/287 F; 260/558 A; 260/600 R; 260/599
[58] Field of Search .................................... 424/251

[56] References Cited

U.S. PATENT DOCUMENTS

| | | | |
|---|---|---|---|
| 3,414,574 | 12/1968 | Frey et al. | 260/256.4 F |
| 3,790,573 | 2/1974 | Blackburn et al. | 260/256.4 F |
| 3,833,588 | 9/1974 | Hardtmann | 260/256.4 F |

*Primary Examiner*—Paul M. Coughlan, Jr.
*Assistant Examiner*—James H. Turnipseed
*Attorney, Agent, or Firm*—Connolly and Hutz

[57] ABSTRACT

Fused heterocyclic ring systems in which a quinoline or a pyridine component is "fused" to a pyrimidine having a 2-methyl, 2-ethyl, or 2-acetyl group and a 4-keto group, and to similar ring systems in which a quinoline, a naphthalene or a pyridine component is fused to a pyrimidine having a 2-carboxy group and a 4-keto group, derivatives, and pharmaceutically-acceptable cationic salts thereof, and their use as antiallergy agents, and intermediates therefor.

17 Claims, No Drawings

FUSED PYRIMIDIN-4(3H)-ONES AS ANTIALLERGY AGENTS

CROSS-REFERENCE TO RELATED APPLICATIONS

This application is a division of application Ser. No. 485,945 filed July 5, 1974 and now U.S. Pat. No. 3,974,161 which, in turn, is a continuation-in-part of application Ser. No. 444,138 filed Feb. 20, 1974 and now abandoned which, in turn, is a continuation-in-part of application Ser. No. 351,025 filed Apr. 13, 1973 and now abandoned.

BACKGROUND OF THE INVENTION

This invention relates to fused heterocyclic ring systems in which a quinoline, a naphthalene or a pyridine ring system is fused to a 2-methyl-, 2-ethyl, or 2-acetyl pyrimidine-4(3H)-one or to a pyrimidine-2-carboxylic acid 4(3H)-one or a derivative thereof, and their use as anti-allergy agents. More particularly, it relates to 2-alkylpyrimido[4,5-b]quinolin-4(3H)-ones, 2-alkyl-pyrido[4,5-b]pyrimidon-4(3H)-ones wherein alkyl is methyl or ethyl, and the corresponding 2-acetyl derivatives, pyrimido[4,5-b]quinolin-4(3H)-ones-2-carboxylic acids, benzo[g]quinazolin-4(3H)-one-2-carboxylic acids, and pyrido[2,3-d]pyrimidin-4-(3H)-one-2-carboxylic acids; esters, amides, and pharmaceutically-acceptable salts thereof which are useful as inhibitors of allergic reactions, and especially of allergic bronchial asthma.

A number of pyrimido[4,5-b]quinolines (1,3-diazoacridines) are described in the art (J. Chem. Soc., 727 (1927); J. Hetero. Chem. 7, 99 (1970); J. Am. Chem. Soc. 78, 5108 (1956); and J. Chem. Soc., 552 (1948). However, none of them contain a carboxy group or functional derivative thereof, i.e., an ester, amide, acid chloride, with the exception of 2,4-dihydroxy-pyrimido[4,5-b]quinoline-5-carboxylic acid, its methyl ester, amide and acid chloride; 1,3-dimethyl-1,2,3,4-tetrahydro-pyrimido[4,5-b]quinolin-2,4-dione-5-carboxylic acid methyl ester; and 10-methyl-2,3,4,10-tetrahydro-pyrimido[4,5-b]quinolin-2,4-dione-5-carboxylic acid and its methyl ester. The products were investigated as potential riboflavin antagonists, Taylor et al., J. Am. Chem. Soc. 78, 5108 (1956) describe 2-methyl-pyrimido[4,5-b]quinolin-4(3H)-one. No 2-carboxy substituted derivatives are described in the literature.

The known pyrimido[4,5-b]quinolin-4(3H)-one when tested by the passive cutaneous anaphylaxis (PCA) test described herein affords only 33% protection in rats at 3.0 mg./kg. via the intravenous route of administration. It is, relative to the compounds of this invention, of marginal value as an anti-allergy agent.

In the benzo[g]quinazolin-4(3H)-one series of compounds of formula II, no analogs wherein a carboxy group (or an ester or amide thereof) is attached directly to the nucleus appear to have been described in the art. However, 2-carbethoxymethylbenzo[g]quinazolin-4(3H)-one is described by Reid et al., Ber. 96, 1218 (1963). No utility is reported for the compound It afforded 49% protection in the PCA test when administered intravenously at 3.0 mg./kg. Upon acid hydrolysis it undergoes facile decarboxylation at room temperature to 2-methylbenzo[g]quinazolin-4(3H)-one (Reid et al., Ber. 95, 3042, 1962) which shows little or no activity in the PCA test.

Benzo[g]quinazolin-4(3H)-one, the compound related to formula II, is reported in Indian Patent 74,146, March 2, 1963 [C.A. 60, 1773f, 1964] to be active as a bronchodilator. When tested in the PCA test described below it was observed to provide 31% protection in rats at 3.0 mg./kg. by the intraveneous route of administration. It is, at best, of marginal value in the treatment of bronchial allergies.

The preparation of pyrido[2,3-d]pyrimidines containing a 5-carboxy or 5-carbalkoxy group is described by Fatutta, Cazz. Chom. Ital. 93, (5), 576–84 (1963); C.A. 59, 6401 (1963). No utility is reported for the products. Mulvey et al., J. Org. Chem. 29, 2903–7 (1964) report the synthesis of pyrido[2,3-d]pyrimidines having a 6-carboxy, 6-carboxamido, or 6-carbalkoxy group. No reports of pyrido[2,3-d]pyrimidin-4(3H)-one-2-carboxylic acids, esters, or amides of formula III below appear in the literature. The preparation of 2-methylpyrido[2,3-d]pyrimidin-4(3H)-one and its use as a saluretic and circulatory stimulating agent is described in South African Pat. No. 6,902,561, granted Oct. 21, 1969 (C.A. 72, 125071s, 1970).

Allergic reactions, the symptoms resulting from an antigen antibody interaction, manifest themselves in a wide variety of ways and in diffusely different organs and tissues. One of the most disabling and debilitating of the allergic reactions is asthma, a functional condition of the bronchi characterized by periodic and spasmodic attacks of breathlessness, wheezing, coughing, and expectoration of mucous.

Efforts to discover medicinal agents to alleviate the symptoms of the abnormal physiologic state have been extensive. As early as 1910, Metthews, Brit. Med. J., 1, 441 (1910) reported the bronchodilator effects of epinephrine. Since then, Chen and Schmidt, J. Pharmacol. Exper. Therap., 24, 339 (1924) reported the use of the alkaloid ephedrine as an orally efficacious bronchodilator with the same spectrum of activity as epinephrine. In 1940, Konzett, Arch. Exp. Path. Pharmak. 197, 27 (1940) outlined the effects of the potent aerosol bronchodilator isoproterenol. Cullum et al., Brit. J. Pharmacol. Exp. 35, 141 (1969) reported the pharmacology of solbutamol, a potent bronchodilator of prolonged duration, and active via both oral and aerosol administration. Many bronchodilator preparations contain theophylline. These are generally less potent than the sympathomimetic amines such as isoproterenol and solbutamol, and are ineffective in aerosol administration.

Recently, Cox and co-workers, Adv. in Drug. Res., 5, 115 (1970) described the pharmacology of disodium cromoglycate [1,3-bis-(2-carboxychromon-5-yloxy)-2-hydroxypropane, Intal], an agent useful in the treatment of bronchial asthma. It is not a bronchodilator but mediates its therapeutic effects by a unique mechanism of action. It suffers from the lack of oral efficacy and, for optimum results, is administered by inhalation as a solid inhalant.

Although the aforementioned agents represent outstanding contributions toward the treatment of asthma, many of them exert the undesired side effect of cardiac stimulation.

SUMMARY OF THE INVENTION

It has now been found that fused pyrimidines having the formulae

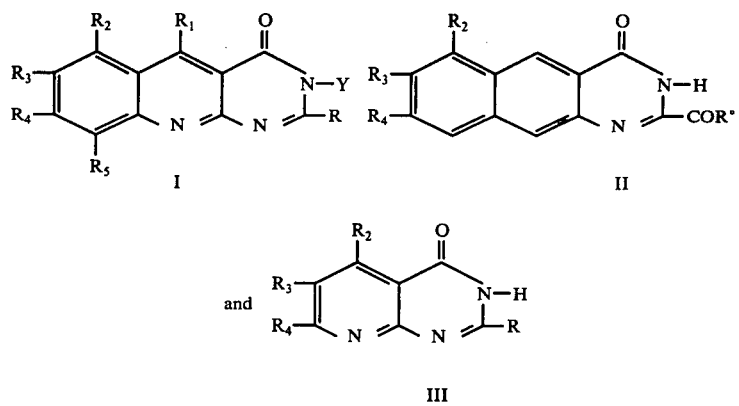

and the pharmaceutically-acceptable cationic salts thereof exert potent allergy effects in mammals, including man, by an Intal-like mechanism. In contrast to Intal, many of these compounds are effective via intraperitioneal and oral administration, as well as by inhalation and intravenous administration.

In the above formulae:

R is selected from the group consisting of methyl, ethyl, acetyl, and COR° wherein R° is selected from the group consisting of hydroxy, alkoxy, hydroxyalkoxy, amino, hydroxyamino;

Y is selected from the group consisting of (a) hydrogen and (b) alkyl, carbalkoxyalkyl, carboxyalkyl, $-(CH_2)_m-O-CO-C_6H_5$ and $(CH_2)_m-O-CO-$alkyl;

with the proviso that when R° is amino or hydroxyamino, Y is hydrogen;

$m$ is an integer from 2 up to, and including, 4;

$R_1$ is selected from the group consisting of hydrogen, alkyl and phenyl;

each of $R_2$, $R_3$, $R_4$, and $R_5$ is selected from the group consisting of hydrogen, alkyl, alkoxy, halo, benzyloxy, hydroxy, thiol, alkanoyloxy, benzoyloxy, methylthio, methylsulfinyl, benzylthio and benzylsulfinyl;

$R_2$ and $R_3$, $R_3$ and $R_4$ when taken together are alkylenedioxy and are selected from the group consisting of methylenedioxy and ethylenedioxy.

The terms "alkyl," "alkanoyloxy" and "alkoxy" as used herein include alkyl, alkanoyloxy and alkoxy groups of from 1 up to, and including, 4 carbon atoms; the term "hydroxyalkoxy" includes hydroxyalkoxy groups having from 2 up to, and including, 4 carbon atoms; and the term "carbalkoxy" includes carbalkoxy groups having from 2 up to, and including, 5 carbon atoms. The term "halo" includes chloro, bromo, fluoro, and iodo.

Compounds of the above formulae are, except for those of formula I wherein Y is hydrogen, R is methyl and each of $R_1-R_5$ is hydrogen and those of formula III wherein R is methyl and each of $R_2-R_4$ is hydrogen, new compounds.

By the term "pharmaceutically-acceptable cationic salts" is intended salts such as the alkali metal salts, e.g., sodium and potassium; alkaline earth metal salts such as calcium and magnesium; aluminum salts; ammonium salts; and salts with organic bases, e.g., amines such as triethylamine, tri-n-butylamine, piperidine, triethanolamine, diethylaminoethylamine, N,N'-dibenzylethylenediamine and pyrrolidine.

The following compounds are of particular interest to this invention:

Formula I: R is $CH_3$ or COR° wherein R° is alkoxy or hydroxy; each $R_1$, $R_2$, and $R_5$ is hydrogen; and $R_3$ and $R_4$ are hydrogen, hydroxy, or alkoxy; provided that when one of $R_3$ or $R_4$ is hydroxy, the other is alkoxy.

Formula II: R is COR" wherein R" is hydroxy; $R_2$ is hydrogen; and each of $R_3$ and $R_4$ is alike and is hydrogen or alkoxy.

Formula III: R is COR* wherein R* is hydroxy or alkoxy; $R_2$ is hydrogen; and each of $R_3$ and $R_4$ is alike and is hydrogen or alkoxy.

Special interest exists in the following compounds of formula I:

| R | $R_1$ | $R_2$ | $R_3$ | $R_4$ | $R_5$ |
|---|---|---|---|---|---|
| COR°; | H | H | $OCH_3$ | $OCH_3$ | H |
| R° = OH, | H | H | OH | $OCH_3$ | H |
| alkoxy | H | H | $OCH_3$ | OH | H |

Compounds of formulae I, II, and III wherein R is carbalkoxy are also valuable intermediates for production of compounds wherein R is carboxy or carbamyl. This is especially true of formula II compounds since those wherein R is carbalkoxy appear of marginal interest as antiallergy agents.

Compounds wherein any of $R_2-R_5$ is benzyloxy, benzylthio or methylthio, serve as intermediates for compounds wherein the R group is hydroxy, alkanoyloxy thiol, methylsulfinyl, or benzylsulfinyl.

The antiallergy property of the compounds of this invention is evaluated by the passive cutaneous anaphylaxis (PCA) test (Ovary, J. Immun. 81, 355, 1958). In the PCA test, normal animals are injected intradermally (i.d.) with antibodies contained in serum obtained from actively sensitized animals. The animals are then challenged intravenously with antigen mixed with a dye such as Evans' Blue. The increased capillary-permeability caused by the antigen-antibody reaction causes the dye to leak from the site of the antibody injection. The test animals are then asphyxiated and the intensity of the reaction determined by measuring the diameter and intensity of the blue coloration on the inner surface of the animals skin.

DETAILED DESCRIPTION OF THE INVENTION

The compounds of this invention can be prepared by a variety of methods. Since structures I, II and III have in common the fused pyrimidine ring, the same reactions can be used to complete this portion of each structure. Similarly, the fused pyridine rings of structures I and III can be obtained by the same type of reaction using, of course, the appropriate precursor in each instance.

Compounds of formula I (R = COR*) can be prepared by methods in which use is made of the intact carbocyclic ring and the quinoline and pyrimidine systems built up in many ways. These methods have, as a common ground, the construction of the 2-aminoquinoline-3-carboxamide, or 3-carboxy acid or ester thereof, from the intact carbocyclic ring and subsequent use of the quinoline system as a basis for building up the pyrimidine ring. The general scope of these methods is summarized in the sequence below wherein R' represents hydroxy, alkoxy and amino:

(Route A)

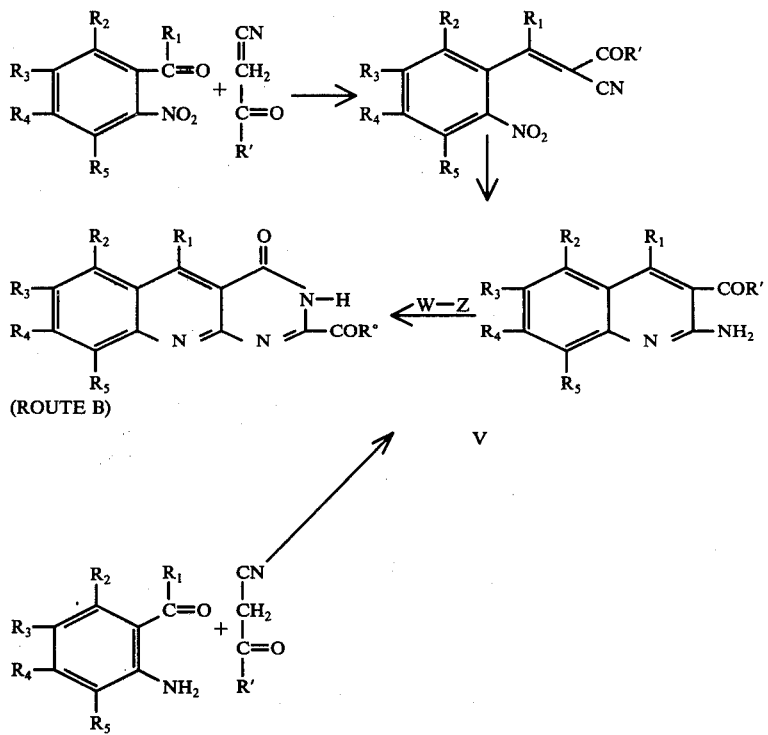

(ROUTE B)

The preferred process on the basis of yield and quality of the final product of formula I is illustrated by Route A. Alternate methods, e.g., Route B, can also be used as is discussed below.

In each of Routes A and B, the condensation involves the carbocyclic aldehyde or ketone with an active methylene nucleophile. The requisite carbocyclic aldehydes or ketone reactants are known materials or are prepared by methods described in the art. By "active methylene" nucelophile is meant a compound having a relatively acidic methylene group; that is, a methylene group linked to one, and preferably two, electron-withdrawing groups such as —CN, —COCl, —C(NH)NH$_2$, COR', —C(NH)—O—alkyl and —CO—alkyl.

The condensation is conducted in the presence of a reaction-inert solvent; that is, a solvent which is not changed as a result of the reaction even though it may participate in the reaction in the role of a catalyst or in salt formation with a reactant or product.

Suitable solvents are alkanols, such as methanol, ethanol, isopropanol, n-butanol and n-hexanol; chlorinated solvents such as methylene chloride, ethylene chloride, chloroform and carbon tetrachloride; pyridine; aromatic hydrocarbons such as benzene, toluene, xylene; hexane; and N,N'-dimethylformamide. Other solvents are found by simple experimentation. Methanol is a preferred solvent, especially when using piperidine as catalyst, because, of the satisfactory yields, ease of separation and purity of products. A solvent system of piperidine and pyridine is frequently a useful system.

A catalyst is often used to facilitate the condensation even when the nucleophiles possess two activating groups as to derivatives of cyanoacetic acid. Suitable catalysts are ammonia, primary, secondary, and tertiary amines, such as n-butylamine, diethylamine, triethylamine, pyridine, piperidine, pyrrolidine, alkali metal alkoxides and fluorides, stannous fluoride, and basic ion-exchange resins of the amine type, e.g., Amberlite IR-45 (a weakly basic polystyrene with polyamine groups, available from Rohm & Haas Co.) and De-Acidite G (polystyrene resin with diethylamino groups; available from the Permutit Co., Ltd., London).

The amount of catalyst used is not critical but can vary over a wide range, i.e., from about 0.1% to about 100% by weight based upon the carbocyclic aldehyde reactant. The favored range of catalyst is from about 10% to about 30% by weight of the carbocyclic aldehyde reactant.

The reaction is conducted at a temperature of from about 0° C. to about 50° C. and generally at about ambient temperature for periods of from about one-fourth to five hours. The products generally separate from the reaction mixtures as solids and are recovered by filtration. Those which do not separate as solids are recovered by evaporation of the solvent or by pouring into a large volume of a non-solvent for the product.

The use of an o-nitrobenzaldehyde or an $R_1$-(2-nitrophenyl) ketone as the reactant (Route A) produces an α-cyano-β-(2-nitrophenyl)acrylamide derivative, e.g., an amide when R' of the active methylene reactant is $NH_2$, which must subsequently be reduced and cyclized to provide the desired 2-aminoquinoline-3-carboxylic acid derivative. Reduction (of the nitro group to an amino group) is accomplished by a variety of reagents. In brief, any reagent which will selectively or preferentially reduce the nitro group to an amino group can be used. Representative of such reagents re metalacid combinations such as iron-acetic acid, iron-hydrochloric acid, tin or stannous chloride-hydrochloric acid, zinc-hydrochloric acid, zinc dust-alkali; and catalytic hydrogenation using catalysts such as platinum, palladium and Raney nickel.

The reduced product appears to cyclize immediately, or almost immediately, to provide the 2-aminoquinoline-3-carboxylic acid derivative.

When using an o-aminobenzaldehyde as reactant (Route B) the condensation product with the cyanoacetic acid derivative cyclizes at a very rapid rate to the 2-aminoquinoline-3-carboxylic acid derivative as noted above for the reaction product of Route A.

Formation of the fused pyrimidine ring with its 2-carboxylic acid derivative (ester or amide) substituent can be accomplished by a number of methods. For convenience, these methods are considered on the basis of the structure of reactant W-Z which contributes the one-carbon fragment to complete the pyrimidine ring system upon the appropriate 2-aminoquinoline-3-carboxylic acid derivative:

1. Reaction of a 2-aminoquinoline-3-carboxamide (formula V, $R=NH_2$) with:
   a. a dialkyl oxalate;
   b. a monoacid halide (chloride, bromide) of a half-alkyl oxalic acid ester;
   c. an alkyl cyanoformate;
   d. a dialkyl ester of monoiminooxalic acid (a carbalkoxy formimidate);
   e. an alkyl ester of oxamidic acid;
   f. 1-cyanoformamide;
   g. cyanogen; and
   h. 1-carbalkoxyformamidine; or
2. Reaction of an alkyl 2-aminoquinoline-3-carboxylate with:
   a. a 1-carbalkoxyformamidine.

Reactant W—Z (an oxalic acid derivative) of the step common to Routes A and B provides the one-carbon fragment needed to complete the fused pyrimidine ring. It may, depending upon choice of reactants, also provide the —NH group. It represents cyanogen and W—COR° wherein W is —COCl, —CN, —COR°, —CO—alkyl, —C(NH)$NH_2$ and —C(NH)O—alkyl. When W—Z is an alkyl ester of oxamidic acid, e.g., $H_5C_2OOC$—$CONH_2$, the cyclization reaction occurs so as to produce the amide ($R=CONH_2$) of formula I.

It is evident that one of the two reactants in the final step of Routes A and B above must provide the —NH moiety. When the reactant upon which the fused pyrimidine ring is to be formed contains a carboxamide group (e.g., formula V wherein —COR' is —$CONH_2$), reactant W—Z can be any of the substances enumerated above; i.e., cyanogen or W—COR°. However, when the reactant upon which the fused pyrimidine ring is to be formed does not contain a carboxamide group; that is, when —COR' is carboxy or carbalkoxy, or haloformyl, reactant W—Z must provide the —NH group.

The favored process comprising using the appropriate 2-amino-3-carboxamide (formula V wherein $R'=NH_2$) as reactant which is condensed with the W-Z reactant to provide only the one-carbon fragment to complete the pyrimidine ring.

Reaction of the 2-aminoquinoline-3-carboxylic acid derivative with reactant W-Z is carried out in a reaction-inert solvent and desirably, when W is —COR° or C(NH)—O—alkyl, one which will permit removal of by-product alcohol and water by distillation. Repesentative solvents for this cyclization are aromatic hydrocarbons such as xylene, toluene, benzene; an excess of the chosen dialkyloxalate reactant; tetralin and decalin.

Suitable solvents are readily determined by experimentation. A favored solvent when W—Z is a dialkyl oxalate is an excess of the dialkyl oxalate because of its ability to solubilize the reactants and to permit simple removal of by-product alcohol and water. Although the reaction temperature is not critical, the reaction is generally run at an elevated temperature to facilitate removal of alcohol and water. Temperatures of from about 150° to about 185° C. are useful when a dialkyl oxalate is used as solvent. Lower temperatures can be employed with the more reactive oxalic acid derivatives (W—Z) such as ethyl oxalylchloride. A final fusion or heating periodis sometimes beneficial to achieving maximum cyclization and yield of the desired pyrimido[4,5-b]quinolin-4(3H)-one-2-carboxylic acid derivative. The addition of a small amount of a base, such as sodium hydride and alkali metal alkoxides, is frequently useful in promoting cyclization, expecially in making compounds of formula II.

When reactant W—Z results in production of the 2-cyano derivative rather than a 2—COR° derivative, the cyano group is converted to the corresponding 2-carboxamide by acid hydrolysis. When W—Z is a monoacid halide of a half-alkyl oxalic acid ester, an acid acceptor; i.e., an inorganic base, such as triethylamine, pyridine, sodium methoxide, sodium hydroxide, is used to neutralize the by-product acid formed.

When reactant W—Z represents an alkyl ester of glycolic acid, the fused pyrimidines of formulae I–III produced bear the hydroxymethyl group at the 2-position. Such compounds serve as precursors for corresponding aldehydes. The conversion is accomplished by oxidation using chromic anhydride in pyridine (Sarett reagent) or chromic anhydride-pyridine-water (Cornforth reagent). The latter reagent is preferred because of its ease of preparation and handling relative to the Sarett reagent. Further oxidation of the 2-carboxaldehyde by, for example, chromic anhydride-sulfuric acid at about 30°–50° C. produces the 2-carboxylic acid.

Alternatively, the appropriate alkyl benzyloxy acetate; e.g., ethyl benzyloxyacetate, is used as reagent W—Z to produce compounds of formulae I–III wherein the substituent is a 2-benzyloxymethyl group. The benzyl groups of the 2-benzyloxymethyl derivatives thus-produced are removed by reacton with strong acids such as trifluoroacetic acid in the manner described below.

The 5-substituted compounds of formula I are also prepared from the appropriate 4-substituted 2-aminoquinoline-3-carboxamide which, in turn, is prepared by the reaction of malononitrile with the appropriate $R_1$-(2-aminophenyl) ketone, e.g., 2-aminobenzophenone ($R_1$-phenyl) and aminoacetophenone ($R_1$=$CH_3$). The 2-amino-3-cyano-4-substituted quinoline thus produced is hydrolyzed to the corresponding 4-substituted-2-aminoquinoline-3-carboxamide by heating with 95% sulfuric acid, followed by aqueous workup. The process is that described by Campaigne et al., J. Hetero. Chem. 8, 11–120 (1971).

A further method comprises condensation of an appropriate o-nitrobenzaldehyde with a dialkylmalonate to produce an alkyl α-carbalkoxy-β-(2-nitrophenyl)acrylate which is subsequently reduced to the corresponding alkyl α-carbalkoxy-β-(2-aminopheny)acrylate according to procedures described above. The reduced product spontaneously cyclizes to an alkyl 2-oxo-quinoline-3-carboxylate. The 2-oxo derivative is heated directly with 1-carbalkoxy formamidine in ethanol using sodium ethoxide to give compounds of formula I. Or, the 2-oxo derivative is chlorinated with a suitable chlorinating agent such as phosphorous trichloride, phosphorous pentachloride, phosphorous oxychloride in a reaction-inert solvent such as an aromatic hydrocarbon or a halogenated aliphatic or aromatic hydrocarbon (benzene, toluene, xylene, methylene chloride, ethylene chloride, chloroform chlorobenzene) at a temperature of from about 50° to 100° C.

The alkyl-2-chloroquinoline-3-carboxylate thus produced is reacted with an alkyl 1-guanylformate to provide the corresponding alkyl pyrimido-[4,5-b]quinolin-4(3H)-one-2-carboxylate. This cyclization is carried out according to known methods.

Still a further method comprises construction of the central pyridine ring. It involve condensation of the appropriate o-nitrobenzaldehyde with an ester, e.g., an alkyl ester of 4,6-dioxo(3H,5H)-tetrahydropyrimidine-2-carboxylic acid, in the presence of base to produce the corresponding 4,6-dioxo(3H,5H)-5-(2-nitrobenzylidene)tetrahydropyrimidine-2-carboxylic acid ester which, upon subsequent reduction in the manner described above, spontaneously cyclizes to a compound of formula I. A variation on this method involves condensation of the o-nitrobenzaldehyde malondiamide, followed by reaction of the product with a dialkyl oxalate to form the above nitrobenzylidene compound.

Compounds of formula II (R = COR°) are prepared by methods similar to those described above for compounds of formula I but using, of course, in place of a 2-aminoquinoline-3-carboxamide, a 2-aminonaphthalene-3-carboxamide. The reaction conditions for achieving construction of the pyrimidine ring are substantially the same as those described for compounds of formula I.

The compounds of formula III (R = COR°) are similarly prepared from appropriate 2-aminonicotinamide or precursors thereto, e.g., 2-aminonicotinic acid, 2-nitropyridine-3-carboxamides or 3-carboxylic acids, 2-nitro or 2-aminopyridine-3-carboxaldehydes. In preparing compounds of formulae II and III, the favored comprise reacting W—Z with the appropriate 2-amino-3-carboxamide reactant.

The amide and hydroxamic acid derivatives of formula I, II, and III (R° =$NH_2$, NHOH) are prepared by methods described above from W—$CONH_2$, W—CONHOH or by reaction of the precursor alkyl ester o formulae I, II, and III with ammonia or hydroxylamine. The usual procedure when comprises reacting the appropriate ester with ammonia or with hydroxylamine hydrochloride, usually in excess, in the presence of an acid acceptor such as triethylamine. The reaction is facilitated by heating under pressure, i.e., the reaction is carried out in a bomb, in a solvent such as ethanol for from about 4 to about 20 hours and the product then recovered by suitable means.

The 2-methyl and 2-ethyl analogs of formulae I and III are prepared by cyclization of the appropriate 2-amino-quinoline-3-carboxamide or 2-aminonicotinamide with the appropriate alkanoic acid anhydride e.g., acetic or propionic anhydride; or with triethyl orthoacetate or triethyl orthopropionate in the presence of sulfuric acid. Treatment of the product with dilute alkali followed by reacidification provides the 2-methyl or ethyl analogs. The preparation of 2-methyl-pyrimido[4,5-b]quinolin-4(3H)-one by this procedure is reported by Taylor et al., J. Am. Chem. Soc. 78, 5108–15 (1956) as previously noted. The 2-ethyl analogs, new compounds, are primarily of valve as intermediates for preparation of the corresponding 2-acetyl derivatives of formulae I and III.

The 2-acetyl derivatives of formulae I and III are prepared by oxidation of the corresponding 2-ethyl derivatives with selenium dioxide and water in a suitable solvent medium, for example, dioxane. In the usual procedure the 2-ethyl derivative and selenium dioxide are used in about a 2:1 molar ratio at an elevated temperature, e.g. from about 50° to about 100° C. Additional selenium dioxide beyond the 2:1 molar ratio can be used to expedite the oxidation.

The 2-methyl analogs of formulae I and III are useful intermediates for preparation of corresponding 2-carboxaldehydes and 2-carboxylic acids, and from them, of corresponding esters of the acids.

A useful procedure for preparing 2-carboxylic acids comprises refluxing the appropriate 2-methyl derivative in a solvent such as ethanol with a slight excess of benzaldehyde in the presence of sodium ethoxide or piperidine, or other base, to form the benzylidene adduct. The amount of base used is not critical but can vary from a catalytic amount (<1%) up to an equivalent amount. The benzylidene adduct is isolated by removal of the solvent and is then oxidized to the acid by excess cold potassium permanganate in aqueous acetone, or by ozonolysis. Alternatively, the methyl group is converted to the corresponding 2-bromomethyl compound by reaction with N-bromosuccinimide in chloroform. The succinimide by-product is removed by concentration of the reaction mixture and filtration. The filtrate is taken to dryness and the residue dissolved in aqueous sulfuric acid and treated with chromium trioxide to provide the acid.

Conversion on the 2-methyl groups to 2-carboxaldehyde groups is achieved by oxidation with selenium dioxide and water in the manner described above for conversion of 2-ethyl to 2acetyl groups. Alternatively, the 2-methyl group is transformed to the 2-bromomethyl group according to the procedure mentioned above which is then hydrolyzed to the corresponding 2-hydroxymethyl group.

The alkylene glycol esters of formula I-III (R=COR° wherein R° is hydroxyalkoxy) are conveniently prepared by a base catalyzed transesterification process. The process comprises treating a compound of formulae I-III wherein R° is alkoxy iwth an alkylene glycol, preferably in the presence of a catalytic amount of a base (i.e., from about 20% by weight based upon the alkylene glycol used), such as triethylamine or calcium hydroxide, in air at a temperature of from abut 20° C. to about 50° C. higher temperatures can be used but appear to offer no advantages.

Compounds of formula I wherein Y is other than hydrogen are prepared by alkylation of formula I compounds wherein Y is hydrogen. The procedure comprises formation of the sodium salt by reaction of the appropriate formula I compound with sodium hydride in a suitable solvent, e.g., N,N-dimethylformamide. Reacton of the sodium salt with I—Y, Br—Y (or Cl—Y) affords the alkylated derivative. When using Cl—Y as alkylating agent, the presence of a small amount of sodium or potassium iodide (from about 10 to 20% by weight of Cl—Y) serves to accelerate the reaction.

Compounds of formulae I-III wherein any of $R_2$, $R_3$, $R_4$, or $R_5$ is benzyl methylsulfinyl are readily prepared from the corresponding thioether compounds by oxidation with an appropriate oxidizing agent such as hydrogen peroxide or a per acid such as m-chlorperbenzoic acid accord to methods known to those skilled in the art.

The methylthio compounds are, in turn, readily prepared by the reaction of the corresponding chloro compound of formula IV; i.e., an $\alpha$-cyano-$\beta$-(2-nitro-chlorophenyl)acrylamide, with sodium methyl mercaptide. Modifications of this method are obvious to those skilled in the art. For example, the methylthio ether of formula IV can be made by in situ formation of the methyl mercaptide salt. Similarly, benzyloxy, benzylthio, and alkoxy compounds are prepared by reacting the corresponding chloro compound of formula IV with sodium benzyloxide, sodium benzylmercaptide, or a sodium alkoxide.

Compounds of formulae I-III wherein any of $R_2$-$R_5$ is benzyloxy or benzylthio serve as intermediates for the corresponding hydroxy and thiol compounds and acyl derivatives thereof. Debenzylation is conveniently accomplished by treating the benzyl ether or benzylthio ether with trifluoroacetic acid. The debenzylated products are obtained as their trifluoroacetate salts. The hydroxy and thiol compounds, in turn, are intermediates for preparation of corresponding alkanoyloxy, and benzoyloxy derivatives by acylation using the appropriate acid anhydride e.g. acetic anhydride. A catalytic amount of p-toluenesulfonic acid is generally used to expedite the reaction.

The products of this invention and the pharmaceutically-acceptable cationic salts thereof, are useful for the control (prophylactic and therapeutic treatment) of allergic symptoms and reactions in mammals, and can be administered either as individual therapeutic agents or as mixtures of therapeutic agents, for example, with theophylline or sympathomimetic amines. They can be administered alone, but are generally administered with a pharmaceutical carrier selected on the basis of the chosen route of administration and standard pharmaceutical practice. For example, they can be combined with various pharmaceutically-acceptable inert carriers in the form of tablets, capsules, lozenges, troches, hard candies, powders, aerosol sprays, aqueous suspensions or solutions, injectable solutions, elixirs, syrups and the like. Such carriers include solid diluents or fillers, sterile aqueous media and various non-toxic organic solvents. Moreover, the oral pharmaceutical compositions of this invention can be suitably sweetened and flavored by means of various agents of the type commonly used for this purpose.

The particular carrier selected and the proportion of active ingredient to carrier are influenced by the solubility and chemical nature of the therapeutic compounds, the chosen route of administration and the needs of standard pharmaceutical practice. For example, when the compounds of this invention are administered orally in tablet form, excipients such as lactose, sodium citrate, calcium carbonate and dicalcium phosphate can be used. Various disintegrants such as starch, alginic acids and certain complex silicates, together with lubricating agents such as magnesium stearate, sodium lauryl sulphate and talc, can also be used in producing tablets for the oral administration of these compounds. For oral administration in capsule form, lactose and high molecular weight polyethylene glycols are among the preferred materials for use as pharmaceutically-acceptable carriers. Where aqueous suspensions are to be used for oral administration, the compounds of this invention can be combined with emulsifying or suspending agents. Diluents such as ethanol, propylene glycol, glycerine and chloroform and their combinations can be employed as well as other materials.

For the purpose of parenteral administration and inhalation, solutions or suspensions of these compounds in sesame or peanut oil or in aqueous propylene glycol solutions can be employed, as well as sterile aqueous solutions of the soluble pharmaceutically-acceptable salts described herein. These particular solutions are especially suited for intramuscular and subcutaneous injection purposes should such method of administration be desired. The aqueous solutions, including those of the salts dissolved in pure distilled water, are also useful for intravenous injection purposes provided that their pH is properly adjusted beforehand. Such solutions should also be suitably buffered, if necessary, and the liquid diluent first rendered isotonic with sufficient saline or glucose.

The compounds can be administered to asthmatic subjects suffering from bronchoconstriction by means of inhalators or other devices which permit the active compounds to come into direct contact with the constricted areas of the tissues of the subject.

When administered by inhalation, the compositions can comprise (1) a solution or suspension of the active ingredient in a liquid medium of the type mentioned above for administration via a nebulizer; (2) a suspension or solution of the active ingredient in a liquid propellant such as dichlorodifluoromethane or chlorotrifluoroethane for administration from a pressurized container; or (3) a mixture of the active ingredient and a solid diluent (e.g., lactose) for administration from a powder inhalation device. Compositions suitable for inhalation by means of a conventional nebulizer will comprise about 0.1 to about 1% of active ingredient; and those for use in pressurized containers will comprise from about 0.5 to about 2% of active ingredient. Compositions for use as powder inhalants can comprise ratios of active ingredient to diluent of from about 1:0.5 to about 1:1.5.

It is necessary that the active ingredient form a proportion of the composition such that a suitable dosage form will be obtained. Obviously, several dosage unit forms can be administered about the same time. Although compositions with less than 0.005% by weight of active ingredient might be used in certain instances, it is preferred to use compositions containing not less than 0.005% of the active ingredient; otherwise, the amount of carrier becomes excessively large. Activity increases with the concentration of the active ingredient. The composition may contain 10, 50, 75, 95 or an even higher percentage by weight of the active ingredient.

The PCA reaction test procedure employed to evaluate the compounds of the present invention demonstrates an excellent correlation between activity for compounds in this test and their utility in the treatment of allergic asthma. The ability of agents to interfere with PCA reactions is measured in male Charles River Wistar rats, 170–210 g. Reaginic antisera is prepared according to Mota, Immunology, 7, 681 (1964) using hen egg albumin and *B. pertussis.* Hyperimmune antisera to hen egg albumin is prepared according to Orange, et al., J. Exptl. Med., 127, 767 (1968). Forty-eight hours prior to antigen challenge the reaginic antisera is injected intradermally (i.d.) into the shaved skin of a normal rat's back; 5 hours before challenge the hyperimmune antisera is similarly injected; 5 hours later, at a third site, 60 mcg. histamine dihydrochloride is injected i.d. as a check for antihistaminic and unspecific types of blockage; the compounds of the instant invention or saline are then administered i.v. and immediately followed by 2.5 mg. Evan's blue dye and 5 mg. egg albumin in saline. In the case of oral administration Evan's blue dye and egg albumen are given five minutes after administration of the drug. Thirty minutes later the animals are asphyxiated using chloroform and the skin of the back removed and reversed for observation. A score is assigned each injection site equal to the product of the diameter of the site in mm. and a grade of 0.1, 0.5, 1, 2, 3 or 4 proportional to intensity of dye coloration. The scores for a given injection site are summed for each group of 8 animals and compared to the saline treated controls. The difference is expressed as percent blockade due to the compound employed.

Compounds representative of those in the present invention are tested by the aforementioned procedure, and the resulting activities are reported as the degree (%) of protection. Disodium cromoglycate, a commerial antiallergy agent, is included for comparison.

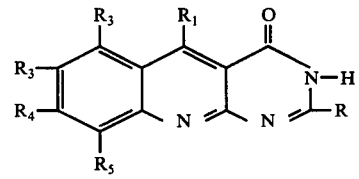

I

TABLE I

Antiallergy Activity of Pyrimido[4,5-b] Quinolin-4(3H)-One-2-Carboxylic Acid Derivatives (Formula I)

| R | $R_1$ | $R_2$ | $R_3$ | $R_4$ | $R_5$ | I.V.* mg/kgg | % | Oral mg/kg | % |
|---|---|---|---|---|---|---|---|---|---|
| $COOC_2H_5$ | H | H | H | H | H | 10 | 100 | 100 | 80 |
| | | | | | | 3 | 99 | 60 | 100[3] |
| | | | | | | 1 | 100[4] | 30 | 72[3] |
| | | | | | | 0.3 | 82[6] | 10 | 775[3] |
| | | | | | | 0.1 | 45[6] | 3 | 69[2] |
| | | | | | | 0.03 | 30[6] | 1 | 12[2] |
| COONa | H | H | H | H | H | 1 | 92 | 100 | 96 |
| | | | | | | 0.3 | 68 | 330 | 557 |
| | | | | | | | | 10 | 0 |
| $COO(n-C_4H_9)$ | H | H | H | H | H | 1 | 90 | 30 | 50 |
| | | | | | | 0.03 | 6 | | |
| $CONH_2$ | H | H | H | H | H | 3 | 98 | 60 | 23 |
| $COOC_2H_5$ | H | H | $OCH_3$ | $OCH_3$ | H | 1 | 100 | 10 | 80[17] |
| | | | | | | 0.3 | 90[3] | 3 | 75[22] |
| | | | | | | 0.1 | 90[12] | 1 | 51[26] |
| | | | | | | 0.03 | 75[14] | 0.03 | 30[20] |
| | | | | | | 0.01 | 70[17] | | |
| | | | | | | 0.003 | 36[14] | | |
| $COO(n-C_4H_9)$ | H | H | $OCH_3$ | $OCH_3$ | H | 3 | 90 | 30 | 81 |
| | | | | | | 0.3 | 94 | | |
| | | | | | | 0.03 | 100 | | |
| | | | | | | 0.003 | 64 | | |
| $COOCH_2CH_2OH$ | H | H | $OCH_3$ | $OCH_3$ | H | 3 | 97 | 10 | 65 |
| | | | | | | 0.3 | 94 | | |
| | | | | | | 0.03 | 92 | | |
| $CONH_2$ | H | H | $OCH_3$ | $OCH_3$ | H | 3 | 87 | 30 | 4 |
| CONHOH | H | H | $OCH_3$ | $OCH_3$ | H | 3 | 92 | 60 | 3 |
| COONa | H | H | $OCH_3$ | $OCH_3$ | H | 0.1 | 100 | 10 | 17[2] |
| | | | | | | 0.03 | 96 | | |
| | | | | | | 0.01 | 71 | | |
| $CH_3$ | H | H | $OCH_3$ | $OCH_3$ | H | 3 | 77[4] | 3 | 67[6] |
| | | | | | | 0.3 | 45[4] | 1 | 43[6] |
| | | | | | | 0.03 | 11[4] | | |
| $C_2H_5$ | H | H | $OCH_3$ | $OCH_3$ | H | 3 | 56 | 60 | 0 |
| $COCH_3$ | H | H | $OCH_3$ | $OCH_3$ | H | 3 | 100 | 10 | 15 |
| | | | | | | 1 | 21 | | |
| | | | | | | 0.1 | 19[2] | | |
| $COOC_2H_5$ | H | H | $OCH_3$ | $OC_2H_5$ | H | 3 | 97 | 30 | 80[4] |
| | | | | | | 0.3 | 94[2] | 10 | 73[7] |
| | | | | | | 0.1 | 94[2] | 3 | 52[6] |
| | | | | | | 0.03 | 85[4] | 1 | 44[7] |
| | | | | | | 0.01 | 57[3] | 0.3 | 31[2] |
| | | | | | | 0.003 | 66[3] | | |
| $COOC_2H_5$ | H | H | —O—$CH_2$—O— | | H | 1 | 70 | 30 | 0 |
| | | | | | | 0.1 | 0 | | |
| $COOC_2H_5$ | H | H | —O—$CH_2CH_2$—O— | | H | 3 | 72 | | |
| | | | | | | 1 | 64 | | |
| $COOC_2H_5$ | H | H | $OC_2H_5$ | $OC_2H_5$ | H | 3 | 100 | 10 | 81[3] |
| | | | | | | 0.1 | 90[2] | 3 | 64[6] |
| | | | | | | 0.03 | 60[3] | 1 | 40[6] |
| | | | | | | 0.01 | 43[3] | 0.3 | 42[4] |
| | | | | | | 0.003 | 21[3] | | |
| $COOC_2H_5$ | H | H | $OC_2H_5$ | $OCH_3$ | H | 3 | 100 | 10 | 92[4] |

TABLE I-continued
Antiallergy Activity of Pyrimido[4,5-b] Quinolin-4(3H)-One-2-Carboxylic Acid Derivatives (Formula I)

| R | $R_1$ | $R_2$ | $R_3$ | $R_4$ | $R_5$ | I.V.* mg/kgg | % | Oral mg/kg | % |
|---|---|---|---|---|---|---|---|---|---|
| | | | | | | 0.1 | 99[2] | 3 | 83[6] |
| | | | | | | 0.03 | 85[4] | 1 | 76[7] |
| | | | | | | 0.01 | 72[4] | 0.3 | 56[5] |
| | | | | | | 0.003 | 50[4] | | |
| $COOC_2H_5$ | H | H | $OC_2H_5$ | $O-(n-C_4H_9)$ | H | 3 | 90 | 10 | 67[3] |
| | | | | | | 1 | 95 | 3 | 43[2] |
| | | | | | | 0.3 | 44[3] | 1 | 3[2] |
| | | | | | | 0.1 | 28 | | |
| | | | | | | 0.03 | 0 | | |
| $COOC_2H_5$ | H | H | $OC_2H_5$ | $OC_7H_7$ | H | 3 | 71[4] | 30 | 0 |
| | | | | | | 0.3 | 30[2] | 10 | 0 |
| | | | | | | 0.1 | 3[2] | | |
| $COOC_2H_5$ | H | H | H | $OCH_3$ | $OCH_3$ | 3 | 100 | 60 | 26 |
| | | | | | | 0.3 | 39 | 10 | 0 |
| $COOC_2H_5$ | H | H | $OCH_3$ | H | H | 3 | 100 | 10 | 43 |
| | | | | | | 0.3 | 87 | 3 | 32 |
| | | | | | | 0.1 | 68[2] | | |
| $COOC_2H_5$ | H | H | H | $OCH_3$ | H | 3 | 90 | 10 | 43 |
| | | | | | | 0.3 | 20 | | |
| | | | | | | 0.03 | 0 | | |
| $COOC_2H_5$ | H | $OCH_3$ | H | H | $OCH_3$ | 3 | 100 | 30 | 23 |
| | | | | | | 0.3 | 25 | | |
| | | | | | | 0.03 | 0 | | |
| $COOC_2H_5$ | H | H | $OCH_3$ | H | $OCH_3$ | 3 | 97 | 30 | 41 |
| | | | | | | 0.3 | 38 | | |
| | | | | | | 0.03 | 14 | | |
| $COOC_2H_5$ | H | H | $SCH_3$ | H | H | 3 | 88 | 30 | 100 |
| | | | | | | 0.3 | 91 | 10 | 66 |
| | | | | | | 0.03 | 8 | 3 | 21 |
| | | | | | | | | 1 | 0 |
| $COOC_2H_5$ | H | H | $SOCH_3$ | H | H | 3 | 100 | 30 | 12 |
| | | | | | | 0.3 | 58 | | |
| | | | | | | 0.03 | 0 | | |
| $COOC_2H_5$ | H | H | $OCH_3$ | $OCH_3$ | $OCH_3$ | 3 | 88 | 10 | 0 |
| | | | | | | 0.3 | 23 | | |
| | | | | | | 0.03 | 33 | | |
| $COOC_2H_5$ | H | H | H | F | H | 0.1 | 2 | | |
| $COOC_2H_5$ | H | H | F | H | H | 3 | 82 | 30 | 17 |
| | | | | | | 1 | 90 | | |
| | | | | | | 0.03 | 0 | | |
| $COOC_2H_5$ | H | H | Cl | H | H | 1 | 70 | | |
| | | | | | | 0.03 | 0 | | |
| $COOC_2H_5$ | H | Cl | H | H | H | 1 | 96 | 30 | 57 |
| | | | | | | 0.03 | 11 | | |
| $COOC_2H_5$ | $C_6H_5$ | H | H | H | H | 3 | 100 | 10 | 0 |
| | | | | | | 1 | 95 | 1 | 0 |
| | | | | | | 0.3 | 51 | | |
| | | | | | | 0.1 | 9 | | |
| $COOC_2H_5$ | H | H | $CH_3COO$ | $OCH_3$ | H | 3 | 100 | 10 | 40 |
| | | | | | | .003 | 53 | | |
| $COOC_2H_5$ | H | H | OH | $OCH_3$ | H | 0.03 | 97 | 30 | 6 |
| | | | | | | 0.01 | 98 | | |
| | | | | | | 0.003 | 94 | | |
| | | | | | | 0.0003 | 38 | | |
| COOH | H | H | OH | $OCH_3$ | H | 3 | 100 | | |
| | | | | | | 0.01 | 86 | | |
| | | | | | | .003 | 90 | | |
| $COO-(n-C_4H_9)$ | H | H | OH | $OCH_3$ | H | 3 | 100 | 10 | 67[2] |
| | | | | | | .003 | 52 | | |
| $COO-(n-C_4H_9)$ | H | H | $OC_7H_7$ | $OCH_3$ | H | 3 | 100 | 10 | 12 |
| | | | | | | .03 | 57 | | |
| $COO-(n-C_4H_9)$ | H | H | $CH_3COO$ | $OCH_3$ | H | 3 | 100 | 10 | 36 |
| $COOC_2H_5$ | H | H | $OCH_3$ | $OC_7H_7$ | H | 3 | 94 | | |
| | | | | | | 0.3 | 23 | | |
| $COOC_2H_5$ | H | H | $OC_7H_7$ | H | H | 3 | 85 | 10 | 60 |
| | | | | | | 0.3 | 23 | 3 | 3 |
| $COOC_2H_5$ | H | H | OH | H | H | 0.3 | 92 | 10 | 13 |
| | | | | | | 0.03 | 21 | 3 | 4 |
| COOH | H | H | OH | H | H | 3 | 100 | | |
| | | | | | | 0.03 | 91 | | |
| | | | | | | .003 | 4 | | |
| $COOC_2H_5$ | H | H | $OCH_3$ | OH | H | 0.003 | 0 | | |
| | | | | | | 0.3 | 100 | | |
| | | | | | | 3.0 | 100 | | |
| Disodium chromoglycate | | | | | | 100 | 100 | 100 | 0 |
| | | | | | | 30 | 99[2] | | |
| | | | | | | 10 | 89[3] | | |
| | | | | | | 3 | 78 | | |
| | | | | | | 1 | 56[8] | | |
| | | | | | | 0.3 | 29[5] | | |
| | | | | | | 0.1 | 19[3] | | |

*The superscripts indicate a particular value is an average of two or more determinations.

TABLE II
Antiallergy Activity of Benzo[g]Quinazolin-4(3H)-One-2-Carboxylic Acid Derivatives (Formula II)

| R° | $R_2$ | $R_3$ | $R_4$ | $R_5$ | I.V. mg./kg. | % | Oral mg./kg. | % |
|---|---|---|---|---|---|---|---|---|
| $COOC_2H_5$ | H | H | H | H | 10 | 27 | 100 | 38 |
| COOH* | H | H | H | H | 10 | 100 | 100 | 9 |
|  |  |  |  |  | 3 | 36 | 30 | 0 |
|  |  |  |  |  | 1 | 14 | 10 | 33 |

*Tested as disodium salt.

TABLE III
Antiallergy Activity of Pyrido[2,3-d]-Pyrimidin-4(3H)-One-2-Carboxylic Acid Derivatives (Formula III)

| R° | $R_2$ | $R_3$ | $R_4$ | I.V. mg./kg. | % | Oral mg./kg. | % |
|---|---|---|---|---|---|---|---|
| $OC_2H_5$ | H | H | H | 10 | 95 | 100 | 0 |

As regards the dosage regimen of the compounds of this invention, the physician will ultimately determine the dosage which will be most suitable for a particular individual, and it will vary with age, weight and response of the particular patient as well as with the nature and extent of the symptoms, the pharmacodynamic characteristics of the particular agent to be administered, and the route of administration chosen. Generally, small doses will be administered initially, with a gradual increase in the dosage until the optimum level is determined. It will often be found that when the composition is administered orally, larger quantities of the active ingredient will be required to produce the same level as produced by a small quantity administered parenterally.

Having full regard for the foregoing factors, it is considered that an effective daily oral dosage of the compounds of the present invention in humans of from about 10 to about 1500 mg. per day, with a preferred range of about 10 to about 600 mg. per day in single or divided doses, or at about 0.2 to about 12 mg./kg. of body weight will effectively alleviate bronchoconstriction in human subjects. These values are illustrative and there may, of course, be individual cases where higher or lower dose ranges are merited.

When administered intravenously or by inhalation, the effective daily dose is from about 0.5 to about 400 mg. per day, and preferably from about 0.25 to 200 mg. per day, or at about 0.005 to 4 mg./kg. of body weight in single or divided doses.

Ethyl 7,8-dimethoxypyrimido[4,5-b]quinolin-4(3H)-one-2-carboxylate is active via the oral, intravenous, intraperitoneal and inhalation routes of administration. It is active intraperitoneally at 0.3-1 mg./kg; and orally in the range of 0.3-30 mg./kg. When administered by aerosol, concentration related responses are observed using 0.3-30 mg./ml. solutions. Intravenously, it is active at a level as low as 0.003 mg./kg.

It has been observed that ethyl 7,8-dimethoxypyrimido[4,5-b]quinolin-4(3H)-one-2-carboxylate causes a marked but transient hypotension and bradycardia in dogs. The effect appears to be species specific. It appears to be relatively free of toxicity since intravenous doses of 1000 mg./kg. did not cause death in mice.

In addition to compounds of formula I above, analogs thereof wherein $R_1$ is substituted phenyl wherein the substituent is at least one of alkyl, alkoxy, alkylenedioxy and halo, and compounds of formulae I, II and III described herein, and analogs thereof wherein COR° is an amide derived from an amino acid, e.g., ethyl glycine, and those wherein COR° is replaced by a methyl or a 5-tetrazolyl group are useful antiallergy agents in the same manner as are compounds of formulae I-III. So also are analogs of formulae I, II and III, and the just described analogs thereof wherein -COR° is replaced by methyl or a 5-tetrazolyl group, but in which the 4-keto group is replaced by thiono (=S).

Compounds wherein the substituent at the 4-position is thiono (=S) rather than keto (=O) are prepared in the same manner as are the keto compounds but using the appropriate cyanothionacetic acid reactant CN—$CH_2$—CSR' in place of the cyanoacetic acid reactant in either of routes A and B above. Alternatively, the appropriate 2-aminonicotinonitrile, 2-aminoquinolino-3-carbonitrile or 2-aminonaphthalene-3-carbonitrile is reacted with concentrated ammonium hydroxide at about 40°-80° C. while bubbling hydrogen sulfide through the solution for several hours, e.g., 3-5 hours; or by reacting the appropriate nitrile in pyridine containing triethylamine while bubbling hydrogen sulfide through the solution at ambient temperature. Such procedures are described by Mautner, J. Org. Chem. 23, 1450 (1958) and BercatVatterone, Annales de Chimie 7, 312 (1962), respectively. The thioamides thus obtained are reacted with various oxalate derivatives Y—Z as described above for Routes A and B.

The tetrazolyl substituent (T) at the 2-position is prepared from the corresponding compound wherein the 2-substituent is cyano. The reaction comprises treating the 2-cyano compound with hydrazoic acid or, preferably, a mixture of sodium azide and ammonium chloride in N,N-dimethylformamide or dimethylsulfoxide at from about 100° C. to the reflux temperature of the mixture for from about 5 to about 24 hours. The addition of a small excess (1-5%) of ammonium azide or of a Lewis acid serves to expedite the reaction. Alternatively, a mixture of sodium azide and acetic acid can be used to generate the hydrazoic acid in situ. With this system as source of hydrazoic acid, refluxing n-butanol serves as a useful solvent and the reaction mixture is heated to reflux for about 3 to 5 days.

The required 2-cyano derivatives are obtained by reacting the appropriate 3-amino-2-naphthoic acid, 2-aminonicotinic acid or 2-aminoquinolin-3-carboxylic acid with cyanogen, as described by Griess, Ber. 2, 415 (1869) and Ber. 11, 1985 (1878). Alternatively, and preferably, the 2-cyano compounds are prepared by dehydration of the corresponding 2-carboxamides with, for example, phosphoryl chloride according to the procedure set forth in Org. Syn. Coll. Vol. 3, 535 (1955), or with phosphorous pentoxide as described by Hayoshi et al., Chem. Pharm. Bull. (Japan) 12, 43 (1964). Still further, the dehydration can be accomplished by means of p-toluenesulfonyl chloride (tosyl chloride) and pyridine according to the procedure of Stephans et al., J. Am. Chem. Soc. 77, 1701 (1955).

Additionally, 2-tetrazole derivatives of formulae I, II and III are prepared by converting the 2-carboxamide derivatives thereof to the corresponding-2-(N-p-methoxybenzyl)carboxamide according to known methods. The N-substituted amide is reacted with phosgene in pyridine for from about 2 to 5 hours to give an iminochloride. The iminochloride is treated with sodium azide in dry N,N-dimethylformamide at ambient temperature for from 2 to 4 hours to provide the 1,5-disubstituted tetrazole. The p-methoxybenzyl group is then removed by treating the substituted tetrazole with trifluoroacetic acid at about 40° C. and an equivalent of anisole. (The 4-oxo group, if converted to a 4-chloro group by phosgene, is regenerated by alkaline hydrolysis according to standard procedures.)

In still a further method, the 2-(5-tetrazolyl) derivatives are prepared by heating 5-carbethoxytetrazole (Oliveri-Mandola, Gazz. Chim. Ital. 41, I, 59 (1911)) with the appropriate 2-aminoquinolin-3-carboxamide, the 3-aminonaphthalene-2-carboxamide or the 2-aminonicotinamide reactant in an inert solvent. This procedure corresponds to the common step of Routes A and B above but wherein the Y-Z reactant is 5-carbethoxytetrazole.

The amino acid derived amides are conveniently obtained from the corresponding lower alkyl ester, e.g., ethyl ester, by reaction with the appropriate amino acid or derivative thereof in the manner described in Examples VII and IX below. The compound of formula I, N-carbethoxymethyl 7,8-dimethoxypyrimido-[4,5-b]quinolin-4(3H)-one-2-carboxamide ($R_1$, $R_2$, $R_5$ = H; $R_3$, $R_4$ = OCH$_3$; R° = NHCH$_2$COOC$_2$H$_5$), when administered intravenously at 30 and 3 mg./kg. of body weight to rats affords 96 and 32% protection, respectively in the PCA test.

EXAMPLE I

Ethyl Pyrimido[4,5-b]Quinolin-4-(3H)-One-2-Carboxylate

A. 2-Aminoquinoline-3-Carboxamide

Cyanoacetamide (19.4 g., 0.23 mole) is added to a solution of sodium ethoxide (6.65 g., 0.29 mole) in absolute ethanol (460 ml.) maintained at 50° C. The mixture is stirred and o-aminobenzaldehyde (28.0 g., 0.23 mole) in absolute ethanol (100 ml.) added. After fifteen minutes stirring at 50° C., the reaction mixture is cooled in an ice bath, filtered and dried to give 34.5 g (84% yield) of product; m.p. 240°-242° C.

B. Ethyl Pyrimido[4,5-b]quinoline-4(3H)-one-2-carboxylate

A mixture of 2-aminoquinoline-3-carboxamide (25.0 g., 0.134 mole) and diethyl oxalate (500 ml.) is heated to reflux for 4 hours while distilling off the ethanol-water formed. The reaction mixture is then cooled to room temperature, the solid product filtered off, washed with diethyl oxalate and air dried to give 22.6 g. of brownish-green solid; m.p. 245°-246° C. It is purified by recrystallization, with decolorization, from hot chloroform. The off-white solid thus obtained (16.2 g., 45% yield) melts at 247°-248° C.

Analysis: Calcd. for $C_{14}H_{11}N_3O_3$: C, 62.51; H, 4.24; N, 15.67% Found: C, 62.44; H, 4.24; N, 15.67%

The same compound is obtained by: (a) refluxing equimolar amounts of 1-carbethoxyformimidate and ethyl 2-aminoquinoline-3-carboxylate in ethanol for 3 hours. The reaction mixture is concentrated, the product collected by filtration and recrystallized from hot chloroform; or (b) refluxing equimolar amounts of 1-carbethoxyformamidine and 2-aminoquinoline-3-carboxamide in ethanol for 3-4 hours in the presence of an equimolar amount of sodium ethoxide. The reaction mixture is worked up as described in (a) above.

EXAMPLE II

Ethyl 7,8-Dimethoxy pyrimido[4,5-b]Quinolin-4(3H)-One-2-Carboxylate

A. α-Cyano -β-(2-Nitro-4,5-Dimethoxyphenyl)Acrylamide

Piperidine (2.1 g., 0.0237 mole) and 2-cyanoacetamide (22.0 g., 0.263 mole) are added to a slurry of 6-nitroveratraldehyde (50.0 g., 0.237 mole) in methanol (500 ml.). The mixture is heated to reflux for 2 hours, and then cooled in an ice bath and filtered. The bright yellow filter cake is washed with cold isopropanol (300 ml.) and then air dried. Yield = 60.1 g. (93%); m.p. 265°-266° C.

Analysis: Calcd. for $C_{12}H_{11}N_3O_3$: C, 51.99; H, 4.00, N, 15.16%: C, 51.96; H, 4.20; N, 15.23%.

Following the procedure of preparations above, but using the appropriate alkoxy substituted nitrobenzaldehyde reactant, the compounds listed below are prepared:

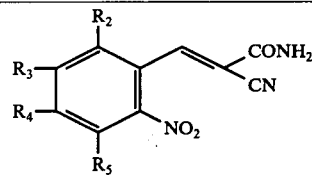

| $R_2$ | $R_3$ | $R_4$ | $R_5$ | m.p. (° C) | % Yield |
|---|---|---|---|---|---|
| H | OCH$_3$ | H | OCH$_3$ | 231-2 (dec.) | 20[a] |
| OCH$_3$ | H | H | OCH$_3$ | 247-8 (dec.) | 82.5 |
| H | H | OCH$_3$ | H | 157-2 (dec.) | 42 |
| H | OCH$_3$ | OCH$_3$ | OCH$_3$ | 244.5 (dec.) | 73.5 |
| H | OC$_2$H$_5$ | O-m-C$_4$H$_9$ | H | | 54 |
| H | OC$_2$H$_5$ | OC$_7$H$_7$ | H | 167-167.5 (dec.) | 73 |
| H | OC$_2$H$_5$ | OCH$_3$ | H | 243-4 (dec.) | 62 |
| H | OC$_2$H$_5$ | OC$_2$H$_5$ | H | 191-3 (dec.) | 79 |
| H | —OCH$_2$—CH$_2$O— | | H | 301.5 (dec.) | 98.2 |
| H | OC$_7$H$_7$ | OCH$_3$ | H | 157-8 | 45 |
| H | OCH$_3$ | OC$_7$H$_7$ | H | 182-3 | 52 |
| H | OC$_7$H$_7$ | H | H | 125-6 | 47 |

[a] refluxed for 18 hours.

B. 6,7-Dimethoxy-2-Aminoquinoline-3-Carboxamide

Iron powder (65.2 g., 1.22 moles) is added over a period of one-half hour to a slurry of α-cyano-β-(2-nitro-4,5-dimethoxyphenyl)acrylamide (75.0g., 0.271 mole) in a 50% solution of acetic acid-N,N-dimethylformamide (750 ml.) at 75° C. When addition of the iron powder is complete, the mixture is heated to 90° C. for four hours and then filtered while hot. The filter cake is washed with hot acetic acid (150 ml.). The dark red filtrate is gradually added to IN hydrochloric acid (1500 ml.) and the pink precipitate recovered by filtration and recrystallized from an excess (10%) of aqueous sodium hydroxide. The solid is filtered, washed with cold isopropanol and dried to give the title product as yellow crystals: Yield = 57.1 g. (83.5%), mpp. 274°-275° C.

Analysis: Calcd. for $C_{12}H_{15}N_3O_3$: C, 58.30; H, 5.29; N, 16.99%. Found: C, 58.06; H, 5.29; N, 17.25%

Upon repetition of procedure B above but using the appropriate α-cyano-β-(2-nitro-alkoxyphenyl)acrylamide from procedure A, the following compounds are prepared:

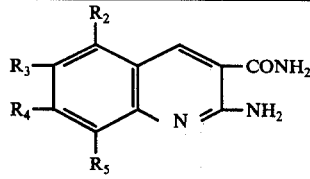

| $R_2$ | $R_3$ | $R_4$ | $R_5$ | m.p. (° C.) | % Yield |
|---|---|---|---|---|---|
| H | OCH$_3$ | H | OCH$_3$ | 284–286 | 52 |
| OCH$_3$ | H | H | OCH$_3$ | 263–4(dec) | 78.5 |
| H | H | OCH$_3$ | H | 281–2(dec) | 82 |
| H | OCH$_3$ | OCH$_3$ | OCH$_3$ | 240–1.5(dec) | 83.2 |
| H | OC$_2$H$_5$ | O-n-C$_4$H$_9$ | H | 252 | 85 |
| H | OC$_2$H$_5$ | OC$_7$H$_7$ | H | 279–80(dec) | 73 |
| H | OC$_2$H$_5$ | OCH$_3$ | H | 234–5(dec) | 83.7 |
| H | OC$_2$H$_5$ | OC$_2$H$_5$ | H | 243–4(dec) | 90.8 |
| H | —OCH$_2$CH$_2$O— | | H | 269.5(dec) | 26.5 |
| H | OC$_7$H$_7$ | OCH$_3$ | H | 264–6 | 80 |
| H | OCH$_3$ | OC$_7$H$_7$ | H | 282–3(dec) | 95 |
| H | OC$_7$H$_7$ | H | H | 238–9 | 94 |

C. Ethyl 7,8-dimethoxypyrimido[4,5-b]quinolin-4(3H)-one-2-carboxylate

To a round-bottomed flask equipped with stirrer, reflux condenser and Dean-Stark apparatus and containing a mixture of diethyl oxalate (50 ml.) and xylene (80 ml.) at reflux is added 6,7-dimethoxy-2-aminoquinoline-3-carboxamide (3.0 g., 0.012 mole). The xylene, water and ethanol are distilled off and collected over a 4 hour period. When all the xylene is removed, the reaction mixture is brought to 185° C., cooled to about 100° C. and then slowly poured into chloroform (300 ml.). The chloroform solution is cooled and the brown precipitate which forms removed by filtration. The filtrate is decolorized with charcoal, concentrated and chilled to give a crystalline mass. The crystals are taken up in hot chloroform, the solution charcoalled filtered and concentrated to give pale yellow crystals; 0.59 g. (15%); m.p. 273°–273° C. (dec.)

Analysis: Calcd. for C$_{16}$H$_{15}$N$_3$O C, 58.41; H, 4.60; N, 12.77%. Found: C, 57.91; H, 4.53; N, 12.37%.

An alternative route to this product comprises heating a mixture of ethyl 6,7-dimethoxy-2-aminoquinoline-3-carboxylate (1.38 g., 5.0 mM), ethyl 1-carbethoxyformimidate hydrochloride (1.82 g., 10 mM), triethylamine (5.1 g., 5.0 mM), ethanol (50 ml.) and N,N-dimethylformamide (20 ml.) on a steam bath for 17 hours. The reaction mixture is cooled and the solid which separates filtered off, triturated with hot chloroform and then recrystallized from chloroform to give 0.170 g. of product. M.P. 273°–274° C. (dec.).

A further alternative route is as follows:

To ethyl oxalyl chloride (80.0 ml.) is added 6,7-dimethoxy-2-aminoquinoline-3-carboxamide (2.0 g., 0.81 mM) and the mixture heated at 95° C. for 2 days. The reaction mixture is then cooled and filtered. The solid product is triturated with and recrystallized from hot chloroform.

Still further, a mixture of 6,7-dimethoxy-2-aminoquinoline-3-carboxamide (0.5 g., 2 millimoles), ethyl cyanoformate (0.43 g., 44 millimiles) and benzene (30 ml.) is refluxed for three days. The mixture is then cooled, filtered and the solid extracted with chloroform. Concentration of the chloroform extract affords the product which is recrystallized from chloroform.

Following the first procedure of C above, but using the appropriate alkoxy substituted 2-aminoquinoline-3-carboxamide reactant from B above and the appropriate ester of oxalic acid, the compounds listed below are prepared:

| R° | $R_2$ | $R_3$ | $R_4$ | $R_5$ | m.p. (° C) | % Yield |
|---|---|---|---|---|---|---|
| O-n-C$_4$H$_9$ | H | OCH$_3$ | OCH$_3$ | H | 263–4(dec) | 14.5 |
| OC$_2$H$_5$ | H | OCH$_3$ | H | OCH$_3$ | 256–7(dec) | 35 |
| OC$_2$H$_5$ | OCH$_3$ | H | H | OCH$_3$ | 254–5(dec) | 24 |
| OC$_2$H$_5$ | H | H | OCH$_3$ | H | 263–4(dec) | 9 |
| OC$_2$H$_5$ | H | OCH$_3$ | OCH$_3$ | OCH$_3$ | 250(dec) | 31.4 |
| OC$_2$H$_5$ | H | OC$_2$H$_5$ | O-n-C$_4$H$_9$ | H | 201–3(dec) | 16 |
| OC$_2$H$_5$ | H | OC$_2$H$_5$ | OC$_7$H$_7$ | H | 241–2(dec) | 41 |
| OC$_2$H$_5$ | H | OC$_2$H$_5$ | OCH$_3$ | H | 264–5(dec) | 16 |
| OC$_2$H$_5$ | H | OC$_2$H$_5$ | OC$_2$H$_5$ | H | 243–4(dec) | 19.1 |
| OC$_2$H$_5$ | H | —OCH$_2$CH$_2$O— | | H | 252.5(dec) | 11.2 |
| OC$_2$H$_5$ | H | OC$_7$H$_7$ | OCH$_3$ | H | 274–5 | 25 |
| OC$_2$H$_5$ | H | OCH$_3$ | OC$_7$H$_7$ | H | 254–5(dec) | 8 |
| O-n-C$_4$H$_9$ | H | OC$_7$H$_7$ | OCH$_3$ | H | 261–2(dec) | 13 |
| OC$_2$H$_5$ | H | OC$_7$H$_7$ | H | H | 256–7(dec) | 32 |

D. 7,8-Dimethoxypyrimido[4,5-b]Quinolin-4(3H)-One-2-Carboxylic Acid

Ethyl 7,8-dimethoxypyrimido[4,5-b]quinolin-4(3H)-one-2-carboxylate (250 mg., 7.4 mM) in 5% aqueous sodium hydroxide (37.5 ml.) is stirred at room temperature for twenty hours. The ester dissolves within 10 minutes and is followed by the gradual appearance of a light colored precipitate. The reaction mixture is acidified by the slow addition of 10% aqueous hydrochloric acid (13 ml.). The light colored precipitate dissolves and a yellow precipitate forms. The acid mixture is stirred for 45 minutes and then filtered. The filter cake is washed with water and then dried in vacuo.

Yield = 140 mg. (63%) of yellow solid. M.P. 277°–280° C. (dec.).

Analysis shows it to be 86% pure. The remainder is sodium chloride plus a small amount of water. It is purified by recrystallization from trifluoroacetic acid. The trifluoroacetate salt monohydrate thus obtained melts at 281°–283° C. (dec.).

Analysis: Calcd. for C$_{14}$H$_{11}$O$_5$N$_3$. CF$_3$COOH—H$_2$O: Calcd. C; 44.34; H, 3.25; N, 9.69; F, 13.15%; Found: C, 43.95; H, 3.17; N, 9.99; F, 13.75%.

Ethyl 7-methoxy-8-ethoxypyrimido[4,5-b]quinoline-4(3H)-one-2-carboxylate is similarly prepared according to procedures A-C, beginning with 3-methoxy-4-ethoxy-6-nitrobenzaldehyde. It melts at 264°-265° C. (dec.)

It and the remaining products of Example II-C are hydrolyzed according to procedure D to afford the corresponding acids.

EXAMPLE III

Ethyl 7-Fluoropyrimido[4,5-b]-Quinolin-4(3H)-One-2-Carboxylate

A. α-Cyano-β-(2-Nitro-5-Fluorophenyl)Acrylamide

A mixture of 3-fluoro-6-nitrobenzaldehyde (10.0 g., 0.0592 mole), 2-cyanoacetamide (5.24 g., 0.0622 mole), piperidine (0.37 g., 4.36 millimole) and ethanol (92 ml.) is heated to reflux on a steam bath for two hours. It is then cooled in an ice-bath whereupon the product precipitates and is recovered by filtration, washed with cold ethanol and dried. Yield = 9.1 g. (65%) of crude product. M.P. 162°-166° C.

It is of sufficient purity for use in the succeeding step.

B. 6-Fluoro-2-Aminoquinoline-3-Carboxamide

Iron powder (8.52 g., 0.152 mole) is gradually added over a forty-minute period to a slurry of α-cyano-β-(2-nitro-6-fluorophenyl)acrylamide (7.97 g., 0.034 mole) in acetic acid (100 ml.) at 85° C. When addition of the iron powder is complete, the mixture is heated to 95°-100° C. for 1.5 hours and then filtered hot through diatomaceous earth. The filtrate is cooled in an ice bath and then filtered to give a tan crystalline solid. The solid is partitioned between ethyl acetate and water, the organic phase separated, dried over anhydrous sodium sulfate and concentrated to yield 6.34 g. (90%) of the title amide as yellow crystals. M.P. 232°-236° C.

C. Ethyl 7-fluoropyrimido[4,5-b]quinolin-4(3H)-one-2-carboxylate

A mixture of diethyl oxalate (57.2 g., 0.392 mole) and 6-fluoro-2-aminoquinoline-3-carboxamide (5.34 g., 0.0261 mole) is heated for 18 hours at 160° C. under a nitrogen atmosphere and then allowed to cool to room temperature. Hexane (300 ml.) is added, the mixture stirred and filtered to provide the desired product. It is washed with hexane and dried. Yield = 4.9 g (71%); m.p. 272° C. (dec.).

Analysis: Calcd. for $C_{19}H_{10}FN_3O_3$: C, 58.54; H, 3.51; N, 14.65; F, 6.61%. Found: C, 58.29; H, 3.47; N, 14.69; F. 6.70%.

EXAMPLE IV

Ethyl 8-Fluoropyrimido&4,5-b]Quinolin-4(3H)-One-2-Carboxylate

A. α-Cyano-β-(2-Nitro-4-Fluorophenyl)Acrylamide

A mixture of 4-fluoro-2-nitrobenzaldehyde (8.70 g., 51.5 millimoles), 2-cyanoacetamide (4.7 g., 54.4 millimoles), piperidine (0.032 g., 0.37 millimole) and ethanol (80 ml.) is stirred at room temperature for 28 hours. The solid which formed is separated by filtration, washed with ethanol (45 ml.) and dried. Yield = 10 g. (83.5%) of the title acrylamide as light tan crystals. M.P. 278°-279° C.

B. 7-Fluoro-2-Aminoquinoline-3-Carboxamide

To a solution of the product of Preparation A above (10.0 g., 0.042 mole) in acetic acid (192 ml.) at 110° C. is gradually added, over a 40 minute period, iron powder (10.3 g., 0.192 mole). The mixture is stirred for 1 hour and then concentrated under reduced pressure to a thick paste. The paste is partitioned between ethyl acetate (100 ml.) and water (100 ml.) and the phases separated. This partition step is repeated three more times. The combined ethyl acetate layers are dried ($Na_2SO_4$), filtered and concentrated to small volume. The solid is filtered off and dried. Yield = 4.72 g. (57.3%) of crude product; m.p. 259°-262° C. It is used directly in the succeeding step.

C. Ethyl 8-fluoropyrimido[4,5-b]quinolin-4(3H)-one-2-carboxylate

Diethyl oxalate (47.5 g., 0.326 mole) and 7-fluoro-2-aminoquinoline-3-carboxamide (3.7 g., 0.015 mole) are mixed together and heated at 160° C. for 7 hours. The reaction mixture is cooled to room temperature, hexane (300 ml.) added, and the brown solid which precipitates filtered off, and washed with hexane (60 ml.). It is then slurried in hot chloroform (250 ml.) and the insoluble material removed by filtration. The hot filtrate is decolorized with charcoal, filtered and dried ($Na_2SO_4$). The light brown solid which precipitates upon cooling is filtered off and recrystallized from isopropyl alcohol. Yield = 1.04 g. (29.2%) of the title ethyl ester. M.P. 248°-251° C.

Analysis: Calcd. for $C_{14}H_{10}FN_3O_3$: C, 58.54; H, 3.51; N, 14.63; F, 6.61%. Found: C, 58.52; H, 3.61; N, 14.76; F. 6.56%.

EXAMPLE V

Ethyl 7-Chloropyrimido[4,5-b]Quinolin-4(3H)-One-2-Carboxylate

A. α-Cyano-β-(2-Nitro-5-Chlorophenyl)Acrylamide

A mixture of 5-chloro-2-nitrobenzaldehyde (47.0 g., 0.25 mole), 2-cyanoacetamide (21.0 g., 0.25 mole), diethylamine (0.5 ml.) and ethanol (500 ml is heated at reflux for 1 hour. Sodium ethoxide (10 mg.) is added to the clear mixture and refluxing continued for an additional 2.5 hours. It is then cooled and the crystalline product which precipitates recovered by filtration. Yield = 52.3 g. (88%); m.p. of crude = 183°-185° C. It is used without purification in step B.

B. 6-Chloro-2-Aminoquinoline-3-Carboxamide

Following the procedure of Example IV-B, α-cyano-β-(2-nitro-5-chlorophenyl)acrylamide (51.0 g., 0.2 mole) is treated with iron powder (56 g., 1.0 mole) to provide 19 g. (43%) of the title carboxamide derivative. M.P. 250°-251° C. when recrystallized from ethanol.

C. Ethyl 7-Chloropyrimido[4,5-b]quinolin-4(3H)-one-2-carboxylate

A mixture of 6-chloro-2-aminoquinoline-3-carboxamide (2.2 g., 0.01 mole), sodium hydride (0.52 g., 0.012 mole as 56% dispersion in oil) and N,N-dimethylformamide (20 ml.) is added to a solution of diethyl oxalate (5 ml.) and N,N-dimethylformamide (5 ml.). The reaction mixture is stirred for 15 minutes, a second portion of sodium hydride (0.52 g., 0.012 mole) added and stirring continued for an additional 15 minutes. Acetic acid (25.0 ml.) is cautiously added to the mixture followed by water (50 ml.). The tan precipitate is removed by filtration and dried (2.0 g. of crude ester). It is purified by chromatography on silica gel using chloroform: 2B ethanol (99:1) as eluant. The product, recovered by concentration of the eluate, is recrystallized from acetic acid. Yield = 1.3 g. (37.3%). M.P. 260.5° C. (dec.). Mass spectra gave m/e = 303.

EXAMPLE VI

Ethyl 7,8-Methylenedioxypyrimido[4,5-b]Quinolin-4(3H)-One-2-Carboxylate

A. 6,7-Methylenedioxy-2-Aminoquinoline-3-Carboxamide

To sodium methoxide (1.90 g., 0.03 mole) in methanol (50 ml.) is added 4,5-methylenedioxy-2-aminobenzaldehyde (5.0 g., 0.03 mole) and 2-cyanoacetamide (2.50 g., 0.03 mole). The mixture is heated to reflux for 15 minutes and then cooled in an ice bath. The bright yellow solid is filtered off and recrystallized from acetic acid to give 6.18 g. (89.3%) of the desired product. M.P. 308° C. (dec.). (m/e = 231)

B. Cyclization of 6,7-methylenedioxy-2-aminoquinoline-3-carboxamide

A mixture of 6,7-methylenedioxy-2-aminoquinoline-3-carboxamide (1.50 g., 6.5 millimoles), sodium methoxide (0.05 g., 1.25 millimoles) and diethyl oxalate (150 ml.) is heated to 150° C. for 3.5 hours. The mixture is then cooled to room temperature to precipitate the product which is recovered by filtration (1.0 g.). It is purified by chromatography on silica gel using chloroform:methanol (99:1) as eluant. The product is recovered by evaporation of the eluate and recrystallization of the residue from ethanol. Yield = 0.414 g. (20.4%) of the cyclized product. M.P. 267° C. (dec.).

Analysis: Calcd. for $C_{15}H_{11}N_3O_5$: C, 57.51; H, 3.54; N, 13.41%. Found : C, 57.19; H, 3.67; N, 13.33%.

EXAMPLE VII 7,8-Dimethoxypyrimido[4,5-b]Quinolin-4(3H)-One-2-Carboxamide

Anhydrous ammonia is bubbled into a mixture of ethyl 7,8-dimethoxypyrimido[4,5-b]quinolin-4(3H)-one-2-carboxylate (300 mg. 9.00 millimoles) in absolute ethanol (75 ml.) for 15 minutes. A clear solution formed followed after a few minutes by formation of a precipitate. The reaction mixture is transferred to a pressure bomb (Monel) and heated in a 95° C. oil bath overnight. The bomb is then cooled to room temperature and the contents removed. The bomb is washed with ethanol and the combined reaction mixture plus wash filtered to recover the product. The filter cake is washed with ethanol and then dried in air. Yield = 260 mg. (95%). M.P. 310° C. (dec.).

EXAMPLE VIII n-Butylpyrimido[4,5-b]Quinolin-4(3H)-One-2-carboxylate (3.0 g., 1.12 millimoles) is added to n-butanol (350 ml.) containing ten drops of hydrochloric acid. The mixture is refluxed for 36 hours, and then cooled and filtered. The solid is dissolved in hot chloroform, the insoluble matter removed by filtration and the filtrate concentrated to provide 1.19 g. of the n-butyl ester (36% yield). M.P. 218°-219.5° C.

Analysis: Calcd. for $C_{16}H_{15}N_3O_3$: C, 64.71; H, 5.09%. Found : C, 64.12; H, 5.20%.

EXAMPLE IX

Pyrimido[4,5-b]Quinolin-4(3H)-One-2-Carboxamide

A mixture of 2-aminoquinoline-3-carboxamide (2.0 g., 1.15 millimoles) ethyl oxamate (2.71 g., 23.1 millimoles), ethylene glycol (10 ml.) and sodium methoxide (10 mg.) is heated at 170° C. for 1 hour. The product is precipitated by slow addition of ice cold methanol (50 ml.) to the hot reaction mixture followed by chilling in an ice bath. It is filtered off, washed with cold methanol and dried in vacuo. Yield = 0.768 g. (28%). M.P. 320° C.

Analysis: Calcd. for $C_{12}H_8O_2N_4$: C, 59.96; N, 3.35; N, 23.32%. Found: C, 50.90; H, 3.43; N, 22.10%.

EXAMPLE X

Ethyl 6-Chloropyrimido[4,5-b]Quinolin-4(3H)-One-2-Carboxylate

A. 5-Chloro-2-Aminoquinoline-3-Carboxamide

Following the procedure of Example I-A, 2-amino-6-chlorobenzaldehyde (5.4 g., 0.035 mole), 2-cyanoacetamide (2.94 g., 0.035 mole), sodium ethoxide (3.0 g., 0.044 mole) in ethanol (50 ml.), the title carboxamide is prepared in 77% yield (5.92 g.). M.P. 270°-273° C. (dec.).

B. Ethyl 6-Chloropyrimido[4,5-b]quinolin-4(3H)-One-2-Carboxylate

Diethyl oxalate (350 ml.) and 5-chloro-2-aminoquinoline-3carboxamide (5.9 g., 0.0267 mole) are heated together at 170° C. for four hours. By-product water and ethanol are distilled from the reaction mixture. The dark reaction mixture is cooled, treated with hexane (300 ml.) and filtered. The brown solid is dissolved in methylene chloride:ethanol (1:1), decolorized with charcoal and concentrated to give a tan solid. The solid is recrystallized from methylene chloride-hexane. It is purified further by chromatography on silica gel using methylene chloride:ethanol (9:1) as eluant. The product, recovered by evaporation of the eluate, is recrystallized from methylene chloride-ethanol. Yield = 0.756 g. (9.3%). M.P. 278°-279° C. (dec.).

Analysis: Calcd. for $C_{14}H_{10}ClN_3O_3$: C, 55.50; H, 3.33; N, 13.87%. Found: C, 55.03; H, 3.21; N, 13.85%.

EXAMPLE XI

Pyrimido[4,5-b]Quinolin-4(3H)-One-2-Carboxylic Acid Disodium Salt

Ethyl pyrimido[4,5-b]quinolin-4(3H)-one-2-carboxylate (5.0 g., 0.0185 mole) is added to 15% aqueous sodium hydroxide (200 ml.) and the mixture stirred for 20 hours at room temperature. The yellow solid which formed is filtered from the reaction mixture, dissolved in water, and the solution adjusted to pH 7 by slow addition of 10% hydrochloric acid. The precipitate is filtered and triturated with methanol. The slurry is filtered, the filter cake washed with methanol and dried. Yield = 4.0 g. (73.4%) of the disodium hemi-hydrate salt. M.P. 345°-347° C. (dec.).

EXAMPLE XII

Ethyl 7-Methoxypyrimido[4,5-b]Quinolin-4[3H)-One-2-Carboxylate

A. α-Cyano-β-(5-Methoxy-2-Nitrophenyl)Acrylamide

Following the procedure of Example II-A, 5-methoxy-2-nitrobenzaldehyde is converted to the title acrylamide derivative in 86% yield. M.P. 207°-208° C. (dec.)

B. 6-Methoxy-2-Aminoquinoline-3-Carboxamide

α-Cyano-β-(5-methoxy-2-nitrophenyl)acrylamide is reacted according to the procedure of Example II-B to give the corresponding quinoline derivative in 79.5% yield. M.P. 231°-232° C. (dec.).

C. Ethyl 7-Methoxypyrimido[4,5-b]-Quinolin-4(3H)-One-2-Carboxylate

6-Methoxy-2-aminoquinoline-3-carboxamide is converted to the title compound by the procedure of Example II-C in 10% yield. M.P. 263°-264° C. (dec.).

Analysis: Calcd. for $C_{15}H_{13}N_3O_4$: C, 60.19; N, 4.38; N, 14.04%. Found: C, 60.28; N, 4.34; N, 14.26%.

EXAMPLE XIII

Ethyl 8,9-Dimethoxypyrimido[4,5-b]-Quinolin-4(3H)-One-2-Carboxylate

The procedures of Example II-A-C are repeated but using 2-nitroveratraldehyde (2.08 g.) in place of 6-nitroveratraldehyde. The yields of melting points of the intermediates and final product are listed below:

A. α-Cyano-β-(2-nitro-3,4-dimethoxyphenyl)acrylamide: Yield = 64%; M.P. 194°-195° C.

B. 7,8-Dimethoxy-2-aminoquinoline-3-carboxamide: Yield = 50%; M.P. 218°-Yield = C.

C. Ethyl 8,9-dimethoxypyrimido[4,5-b]-quinolin-4(3H)-one-2-carboxylate; Yield = 30%; M.P. 233°-234° C. (dec.).

Analysis: Calcd. for $C_{16}H_{15}N_3O_3$: C, 58.35; H, 4.60; N. 12.76%. Found : C, 58.52; H, 4.47; N, 12.68%.

EXAMPLE XIV

7,8-Dimethoxypyrimido-[4,5-b]-Quinolin-4(3H)-One-2-Hydroxamic Acid

Ethyl 7,8-dimethoxypyrimido-[4,5-b]quinolin-4-(3H)-one-2-carboxylate (200 mg., 6.08 millimole) is added to a solution of hydroxylamine hydrochloride (69 mg., 100 millimoles) and triethylamine (100 mg., 100 millimiles) in absolute ethanol (50 ml.). The mixture is heated at 95° C. overnight in a bomb and then cooled. The insoluble yellow solid is filtered off, washed with hot ethanol and dried to provide 143 mg. (74%) of the title product. M.P. 337° C. (dec.).

EXAMPLE XV

Ethyl 7-Hydroxy-8-Methoxypyrimido[4,5-b]Quinolin-4(3H)One-2-Carboxylate Trifluoroacetate A solution of ethyl 7-benzyloxy-8-methoxypyrimido[4,5-b]quinolin-4(3H) one-2-carboxylate (250 mg., 0.618 mmole) in trifluoroacetic acid (5 ml.) is refluxed for 2.5 hours. (Alternatively the mixture is stirred at room temperature for 3 days). The reaction mixture is then poured into ether (25 ml.) and the resulting bright yellow precipitate of the trifluoroacetate salt recovered by filtration, washed with ether and dried.

Yield = 194 mg., 72%; m.p. 279° C.
Analysis:
Calcd. for $C_{15}H_{13}N_3O_5CF_3COOH \frac{1}{2} H_2O$: C, 46.58; H, 3.42; N, 9.58%; Found: C, 46.81; H, 3.41; N, 9.21%.

Repetition of the above procedure but using the corresponding n-butyl ester (862 mg., 0.199 mmole) in place of the ethyl ester, 8 ml. trifluoroacetic acid and a reflux period of 3.5 hours affords n-butyl 7-hydroxy-8-methoxypyrimido[4,5-b]quinolin-4(3H)one-2-carboxylate trifluoroacetate (0.67 g., 74%); m.p. 240°-241° C. (dec.)

Analysis: Calcd. for $C_{17}H_{17}O_5N_3CF_3COOH$: C, 49.89; H, 3.96; N, 9.18; F. 12.46%; C, 49.93; H, 3.97; N, 8.79; F. 11.17%;

Similarly, ethyl 7-benzyloxypyrimido-[4,5-b]quinolin-4(3H) one-2-carboxylate is debenzylated to give a 74% yield of ethyl 7-hydroxypyrimido [4,5-b]quinolin-4(3H)one-2-carboxylate hemitrifluoroacetate; m.p. 274°-275° C. (dec.)

Analysis: Calcd. for $C_{14}H_{11}O_4N_3 \frac{1}{2} CF_3COOH$: C, 57.43; H, 3.66; N. 13.39%. C, 57.75; H, 4.05; N, 13.65%.

EXAMPLE XVI

7-Hydroxy-8-Methoxypyrimido[4,5-b]Quinolin-4(3H)One-2-Carboxylic Acid

The trifluoroacetate-hemihydrate salt of ethyl 7-hydroxy-8-methoxypyrimido[4,5-b]quinolin-4(3H)one-2-carboxylate (200 mg., 0.456 mmole) is slurried in 0.1N sodium hydroxide (5 ml.) and 15% sodium hydroxide added dropwise with stirring until solution is complete. The mixture is stirred at room temperature for 18 hours and is then made strongly acid by addition of trifluoroacetic acid. The precipitate which forms is separated by filtration, washed with water and then with isopropyl alcohol and air-dried. Yield = 114 mg.; m.p. 281° C. (dec).

Analysis: Calcd. for $C_{13}H_9O_5N_3 2H_2O$: C, 48.29; H, 4.02; N, 13.00%. Found C, 47.3; H, 3.32; N, 12.73%.

In like manner, ethyl 7-hydroxypyrimido[4,5-b]quinolin-4(3H)one-2-carboxylate hemitrifluoroacetate (210 mg.) is converted to 7-hydroxypyrimido[4,5-b]quinolin-4(3H)one-2-carboxylic acid. Yield - 191 mg., 91%; m.p. 340° C (dec.)

EXAMPLE XVII

Ethyl 7-Methoxy-8-Hydroxypyrimido[4,5-b]Quinolin-4(3H)One-2-Carboxylate

A solution of ethyl 7-methoxy-8-benzyloxypyrimido[4,5-b]quinolin-4(3H)one-2-carboxylate (198 mg., 0.488 mmole) in trifluoroacetic acid (4 ml.) is stirred at room temperature for 8 days. Ether (15 ml.) is added and the yellow precipitate which forms separated by filtration. It is taken up in chloroform and the solution filtered through diatomaceous earth to remove a small amount of insoluble material. The filtrate is decolorized with charcoal and concentrated under reduced pressure to small volume. The solid which forms is filtered and dried; 9 mg., 6% yield; m.p. 265°-266° C. (dec.).

EXAMPLE XVIII

The compounds below are prepared from appropriate reactants by the procedures of the preceding examples.

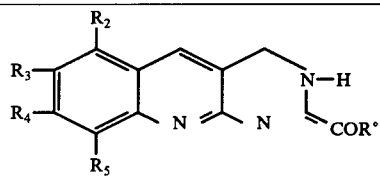

| R° | $R_2$ | $R_3$ | $R_4$ | $R_5$ | Method of Ex. |
|---|---|---|---|---|---|
| $OCH_3$ | H | H | H | H | I |
| NHOH | H | H | H | H | XIV |
| $OCH_3$ | H | F | H | H | III |
| $NH_2$ | H | F | H | H | VII |
| $O-n-C_4H_9$ | H | H | F | H | VIII |
| $NH_2$ | H | H | F | H | VII |
| $NH_2$ | Cl | H | H | H | VII |
| NHOH | Cl | H | H | H | XIV |
| $O-i-C_3H_7$ | H | Cl | H | H | V |
| $NH_2$ | H | Cl | H | H | IX |

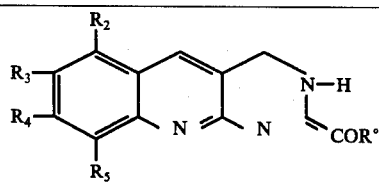

| R° | R$_2$ | R$_3$ | R$_4$ | R$_5$ | Method of Ex. |
|---|---|---|---|---|---|
| OCH$_3$ | H | —O—CH$_2$—O— | | H | VI |
| NH$_2$ | H | —O—CH$_2$—O— | | H | IX |
| NHOH | H | —O—CH$_2$—O— | | H | XIV |
| OCH$_3$ | H | OCH$_3$ | OCH$_3$ | H | II |
| O-n-C$_3$H$_7$ | H | OCH$_3$ | OCH$_3$ | H | II |
| NH$_2$ | H | OCH$_3$ | OCH$_3$ | H | IX |
| NH$_2$ | H | OCH$_3$ | H | H | VII |
| NH$_2$ | H | H | OCH$_3$ | OCH$_3$ | VII |
| OC$_2$H$_5$ | H | OC$_2$H$_5$ | H | H | II |
| OC$_2$H$_5$ | H | H | OC$_2$H$_5$ | H | II |
| NH$_2$ | H | OC$_2$H$_5$ | OC$_2$H$_5$ | H | VII |
| NHOH | H | OC$_2$H$_5$ | OC$_2$H$_5$ | H | XIV |
| OC$_2$H$_5$ | H | Br | H | Br | I |
| OC$_2$H$_5$ | H | Cl | H | Cl | I |
| OCH$_3$ | Cl | H | H | Cl | I |
| OC$_2$H$_5$ | H | H | H | OCH$_3$ | II |
| NH$_2$ | H | H | H | OCH$_3$ | VII |
| NH$_2$ | H | H | OC$_2$H$_5$ | H | VII |
| OCH$_3$ | H | H | Cl | H | V |
| O-n-C$_3$H$_7$ | OCH$_3$ | H | H | OCH$_3$ | II |
| OC$_2$H$_5$ | H | H | I | H | II |
| OC$_2$H$_5$ | Br | H | H | H | V |
| NH$_2$ | Br | H | H | H | VII |
| OC$_2$H$_5$ | OCH$_3$ | —O—CH$_2$—O— | | H | I |
| NH$_2$ | OCH$_3$ | —O—CH$_2$—O— | | H | VII |
| O-i-C$_3$H$_7$ | H | CH$_3$ | H | H | VIII |
| NH$_2$ | H | CH$_3$ | H | H | VII |
| OC$_2$H$_5$ | H | H | CH$_3$ | H | I |
| OC$_2$H$_5$ | H | CH$_3$ | H | H | I |
| NH$_2$ | CH$_3$ | H | H | H | IX |
| NHOH | CH$_3$ | H | H | H | XIV |
| OC$_2$H$_5$ | H | t-C$_4$H$_9$ | H | H | I |
| NH$_2$ | H | t-C$_4$H$_9$ | H | H | VII |
| OCH$_3$ | CH$_3$ | H | CH$_3$ | H | I |
| OC$_2$H$_5$ | CH$_3$ | CH$_3$ | H | H | I |
| NH$_2$ | CH$_3$ | CH$_3$ | H | H | VII |
| OC$_2$H$_5$ | H | C$_2$H$_5$ | H | H | I |
| NH$_2$ | H | C$_2$H$_5$ | H | H | IX |
| NHOH | H | n-C$_3$H$_7$ | H | H | XIV |
| OC$_2$H$_5$ | H | n-C$_3$H$_7$ | n-C$_3$H$_7$ | H | VII |
| NH$_2$ | H | n-C$_3$H$_7$ | n-C$_3$H$_7$ | H | IX |
| OC$_2$H$_5$ | H | H | C$_2$H$_5$ | H | I |
| OC$_2$H$_5$ | H | H | i-C$_3$H$_7$ | H | I |
| OC$_2$H$_5$ | —O—CH$_2$—O— | | OCH$_3$ | H | I |
| O-n-C$_4$H$_9$ | —O—CH$_2$—O— | | OCH$_3$ | H | VIII |
| NH$_2$ | —O—CH$_2$—O— | | OCH$_3$ | H | VII |
| NH$_2$ | —O—CH$_2$—O— | | H | H | VII |
| NH$_2$ | H | —O—CH$_2$—CH$_2$—O— | | H | II |
| OCH$_3$ | OCH$_3$ | OCH$_3$ | OCH$_3$ | H | I |
| NH$_2$ | OCH$_3$ | OCH$_3$ | OCH$_3$ | H | VII |
| O-n-C$_3$H$_7$ | H | CH$_3$ | CH$_3$ | H | I |
| OC$_2$H$_5$ | Br | H | H | H | I |
| OC$_2$H$_5$ | H | Br | H | H | I |
| NH$_2$ | H | Br | H | H | VII |
| OC$_2$H$_5$ | H | H | Br | H | I |
| NHOH | H | H | Br | H | XIV |
| OCH$_3$ | H | H | t-C$_4$H$_9$ | H | II |
| OC$_2$H$_5$ | H | OCH$_3$ | OC$_2$H$_5$ | H | II |
| OCH$_3$ | H | Cl | Br | Cl | II |
| OCH$_3$ | H | H | O-i-C$_3$H$_7$ | OCH$_3$ | II |
| OC$_2$H$_5$ | OCH$_3$ | —O—CH$_2$—O— | | OCH$_3$ | II |
| OC$_2$H$_5$ | H | O-n-C$_4$H$_9$ | O-n-C$_4$H$_9$ | H | II |
| OC$_2$H$_5$ | H | H | Cl | Cl | II |
| OC$_2$H$_5$ | H | H | Cl | Cl | II |
| O-n-C$_4$H$_9$ | H | SCH$_3$ | H | H | II |
| NH$_2$ | H | SCH$_3$ | H | H | VII |
| OCH$_3$ | H | SCH$_3$ | SCH$_3$ | H | II |
| NHOH | H | SCH$_3$ | SCH$_3$ | H | XIV |
| OC$_2$H$_5$ | H | H | H | SCH$_3$ | II |
| OC$_2$H$_5$ | H | H | OC$_7$H$_7$ | OCH$_3$ | II |
| O-n-C$_3$H$_7$ | H | H | OC$_7$H$_7$ | H | II |
| O-n-C$_4$H$_9$ | F | H | OC$_7$H$_7$ | H | II |
| OCH$_3$ | OC$_7$H$_7$ | OCH$_3$ | H | H | II |
| OC$_2$H$_5$ | H | OC$_7$H$_7$ | OC$_7$H$_7$ | H | II |
| OC$_2$H$_5$ | OC$_7$H$_7$ | H | H | H | II |
| OC$_2$H$_5$ | OC$_7$H$_7$ | Br | H | Br | II |
| OCH$_3$ | H | OCH$_3$ | OC$_7$H$_7$ | Br | II |
| OCH$_3$ | H | OC$_7$H$_7$ | OC$_7$H$_7$ | H | II |
| OC$_2$H$_5$ | OC$_7$H$_7$ | OCH$_3$ | OCH$_3$ | H | II |
| OC$_2$H$_5$ | H | Br | H | OC$_7$H$_7$ | I |

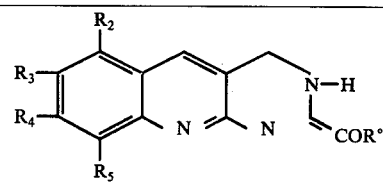

| R° | R$_2$ | R$_3$ | R$_4$ | R$_5$ | Method of Ex. |
|---|---|---|---|---|---|
| O-n-C$_4$H$_9$ | H | H | H | OC$_7$H$_7$ | I |
| O-n-C$_3$H$_7$ | C$_2$H$_5$ | H | OC$_7$H$_7$ | H | III |
| O-n-C$_3$H$_7$ | C$_2$H$_5$ | OC$_7$H$_7$ | H | H | III |
| OC$_2$H$_5$ | H | OC$_7$H$_7$ | OC$_2$H$_5$ | H | II |
| OC$_2$H$_5$ | H | OC$_2$H$_5$ | OC$_7$H$_7$ | H | II |
| OC$_2$H$_5$ | H | F | OC$_7$H$_7$ | H | II |
| OC$_2$H$_5$ | H | Br | OC$_7$H$_7$ | H | II |
| OCH$_3$ | H | Cl | OC$_7$H$_7$ | H | VII |
| NH$_2$ | H | OC$_7$H$_7$ | OC$_7$H$_7$ | OCH$_3$ | VII |
| NH$_2$ | H | OCH$_3$ | OC$_7$H$_7$ | H | IX |
| NHOH | H | OC$_7$H$_7$ | OCH$_3$ | H | XIV |
| NHOH | OC$_7$H$_7$ | OCH$_3$ | OCH$_3$ | H | XIV |
| NHOH | H | OC$_2$H$_5$ | OC$_7$H$_7$ | H | XIV |
| NH$_2$ | H | OC$_7$H$_7$ | OC$_2$H$_5$ | H | VII |
| NH$_2$ | H | F | OC$_7$H$_7$ | H | VII |
| NHOH | H | Cl | OC$_7$H$_7$ | H | XIV |
| NH$_2$ | H | OC$_7$H$_7$ | OCH$_3$ | H | VII |
| NH$_2$ | H | Cl | OCH$_3$ | H | VII |
| OC$_2$H$_5$ | H | SC$_7$H$_7$ | H | H | II |
| NH$_2$ | H | H | H | SC$_7$H$_7$ | VII |
| OC$_2$H$_5$ | H | SC$_7$H$_7$ | C$_2$H$_5$ | H | II |
| OC$_2$H$_5$ | H | H | SC$_7$H$_7$ | H | II |
| NHOH | H | H | SC$_7$H$_7$ | H | XIV |
| OC$_2$H$_5$ | SC$_7$H$_7$ | H | H | SC$_7$H$_7$ | II |
| NH$_2$ | SC$_7$H$_7$ | H | H | SC$_7$H$_7$ | XIV |

The benzyl ethers and benzylthio ethers tabulated above are converted to the corresponding hydroxy and thiol compounds by the procedure of Example XV.

The thus-produced hydroxy and thiol substituted 2-carboxylic acid esters are hydrolyzed to the corresponding 2-carboxylic acid derivatives by the procedure of Example XVI.

EXAMPLE XIX

Ethyl 7-Acetoxy-8-Methoxypyrimido[4,5-b]Quinolin-4(3H)One-2-Carboxylate p-Toluenesulfonate A mixture of acetic anhydride (4 ml.), ethyl 7-hydroxy-8-methoxypyrimido[4,5-b]quinolin-4(3H)one-2-carboxylate trifluoroacetate hemihydrate (250 mg. 0.572 mmole) and p-toluenesulfonic acid monohydrate (100 mg., 0.572 mmole) is heated at 100° C. for 24 hours. The acetic anhydrite is then stripped from the reaction mixture in vacuo. The solid residue is dissolved in hot chloroform and the solution decolorized with activated charcoal. Benzene (4 volumes) is added to the decolorized solution which is then chilled in ice. The crystals which separate are recovered by filtration and air dried. Yield = 174 mg., 58%; m.p. 215°–217° C.

Analysis: Calcd. for C$_{17}$H$_{15}$O$_6$N$_3$ C$_7$H$_8$O$_3$S: C, 54.43; H, 4.37; N, 7.98%. Found C, 53.74; H, 4.28; N, 7.24%.

The above procedure is repeated but using the corresponding n-butyl ester trifluoroacetate salt (200 mg., 0.437 mmole) in place of the ethyl ester trifluoroacetate salt. The product is recovered by concentration of the chloroform solution to 1/3 volume and filtration and the solid which precipitates rather than by precipitation with benzene. Yield - 30 mg., 18%; m.p. 260°–261° C. (dec.)

The above procedure is repeated but using the appropriate acid anhydride and in place of acetic anhydride and the appropriate hydroxy or thiol formula I compound as reactant to give the following compounds:

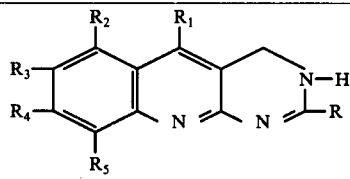

| $R_1$ | $R_2$ | $R_3$ | $R_4$ | $R_5$ | R |
|---|---|---|---|---|---|
| H | H | $C_2H_5COO$ | $OCH_3$ | H | $COOC_2H_5$ |
| H | H | $C_3H_7COO$ | $OCH_3$ | H | $COOC_2H_5$ |
| H | H | HCOO | $OCH_3$ | H | $COOC_2H_5$ |
| H | H | $OCH_3$ | $CH_3COO$ | H | $COOC_2H_5$ |
| H | H | $OCH_3$ | $C_2H_5COO$ | H | $COOC_2H_5$ |
| H | H | $OCH_3$ | HCOO | H | $COOC_2H_5$ |
| H | H | HCOO | $OCH_3$ | H | $COO$-n-$C_4H_9$ |
| H | H | $CH_3COO$ | $OCH_3$ | H | $COO$-n-$C_4H_9$ |
| $C_6H_5$ | H | HCOO | H | H | $CH_3$ |
| $C_6H_5$ | H | $C_3H_7COO$ | $OCH_3$ | H | $CH_3$ |
| H | H | H | HCOO | H | $COO$-n-$C_3H_7$ |
| H | H | H | $CH_3COO$ | H | $COO$-n-$C_3H_7$ |
| $C_6H_5$ | H | H | $CH_3COO$ | $OCH_3$ | $CH_3$ |
| H | H | $CH_3COO$ | $CH_3COO$ | H | $COOC_2H_5$ |
| H | H | HCOO | HCOO | H | $COOC_2H_5$ |
| H | H | $OCH_3$ | $CH_3COO$ | Br | $COOCH_3$ |
| H | $CH_3COO$ | $OCH_3$ | H | H | $C_2H_5$ |
| $CH_3$ | H | $C_6H_5COO$ | $OCH_3$ | H | $C_2H_5$ |
| n-$C_4H_9$ | H | $C_6H_5COO$ | $OCH_3$ | H | $C_2H_5$ |
| $C_6H_5$ | H | $CH_3COO$ | H | H | $C_2H_5$ |
| H | $C_3H_7COO$ | $OCH_3$ | H | H | $COOCH_3$ |
| H | $CH_3COO$ | $OCH_3$ | $OCH_3$ | H | $COOC_2H_5$ |
| H | H | Br | H | $CH_3COO$ | $COOC_2H_5$ |
| H | H | H | H | HCOO | $COO$-n-$C_4H_9$ |
| H | H | H | H | $C_3H_7COO$ | $COO$-n-$C_4H_9$ |
| H | $C_2H_5$ | H | $CH_3COO$ | H | $COOC_2H_5$ |
| $CH_3$ | H | $CH_3COO$ | $OC_2H_5$ | H | $CH_3$ |
| $C_2H_5$ | H | F | $CH_3COO$ | H | $C_2H_5$ |
| n-$C_4H_9$ | $C_2H_5$ | $CH_3COO$ | H | H | $C_2H_5$ |
| H | H | Cl | $CH_3COO$ | H | $COOCH_3$ |
| $C_2H_5$ | H | F | $C_3H_7COO$ | H | $COOC_2H_5$ |
| H | $C_2H_5$ | HCOO | H | H | $COO$-n-$C_3H_7$ |
| H | H | $CH_3COO$ | H | H | $COO$-n-$C_3H_7$ |
| H | H | $C_3H_7COO$ | H | H | $COO$-n-$C_3H_7$ |
| H | H | $CH_3COO$ | H | H | $COOCH_3$ |
| H | H | $C_3H_7COO$ | H | H | $COOCH_3$ |
| H | H | $CH_3COO$ | $CH_3COO$ | H | $COOCH_3$ |
| H | H | H | $C_2H_5COO$ | H | $COOC_2H_5$ |
| $CH_3$ | H | $C_6H_5COO$ | $OCH_3$ | H | $COOC_2H_5$ |
| H | H | $OCH_3$ | $C_6H_5COO$ | H | $COOC_2H_5$ |
| H | H | Cl | $C_6H_5COO$ | H | $COOC_2H_5$ |

EXAMPLE XX

2-Hydroxyethyl 7,8-Dimethoxy-pyrimidin[4,5-b]quinolin-4-(3H)-One-2-Carboxylate Triethylamine (1 ml.) is added to a slurry of ethyl 7,8-dimethoxypyrimidin ]4,5-b]quinoline-4(3H)-One-2-carboxylate (500 mg.) in ethylene glycol (5 ml.). The mixture is stirred for 6 hours and is then diluted with water (30 ml.). The resulting clear yellow solution is acidified with acetic acid and the precipitate which forms filtered off. It is recrystallized while still damp from N,N-dimethylformamide (20 ml.). Yield = 285 mg. (53.5%). m.p. 252° C.

Analysis: Calcd. for $C_{16}H_{15}N_3O_6$: C, 55.65; H, 4,48; N, 12.17%. Found: C, 55.35; H, 4.51; N, 12.39%.

In like manner, the alkyl esters of Example II-XIX, XXI-XXIII and XXVII-XXXII are transesterified to the corresponding 2-hydroxyethyl esters. Replacement of ethylene glycol by propylene glycol, butylene glycol or 1,4-dihydroxybutane affords the corresponding hydroxyalkyl esters.

EXAMPLE XXI

Ethyl 7-Methylthiopyrimido[4,5-b]quinolin-4(3H)-One-2-Carboxylate

A. α-Cyano-β-(2-Nitro-5-Methylthiophenyl)acrylamide

A solution of the sodium salt of methylmercaptan (2.78g., 0.0398 Mole) in N,N-dimethylformamide (50 ml.) is prepared by bubbling methylmercaptan into a mixture of sodium hydride (1.67 g. of 57% NaH) in N,N-dimethylformamide (50 ml.). The reaction mixture is cooled by means of an ice-bath until the reaction is complete.

The sodium methylmercaptide solution is then added dropwise to a mixture of α-cyano-β-(2-nitro-5-chlorophenyl)acrylamide (10 g., 0.0398 mole) in N,N-dimethylformamide (35 ml.) cooled in an ice-bath. The mixture is stirred for one hour and then removed from the ice-bath and stirred for an additional 2 hours. The reaction mixture is poured into water (600 ml.) and the resulting mixture thoroughly stirred. Ether (30 ml.) is added and the precipitate filtered off, washed with ether and dried. Yield = 8.4 g.; M.P. = 227°-229° C.

B. 6-Methylthio-2-Aminoquinoline-3-Carboxamide

A mixture of α-cyano-β-(2-nitro-5-methylthiophenyl)acrylamide (8,4 g., 0.032 mole) in acetic acid - N,N- dimethylformamide (110 ml. of 1:1) is heated in a 75° C. bath. Iron powder (2.0g.) is added and the mixture stirred until the internal temperature rose to 95° C. Additional iron powder (6.16 g. total iron added=0.146 mole) is added in small portions over a 15 minute period. The reaction mixture is stirred for one hour following completion of addition and then filtered hot. The iron residue is washed with hot acetic acid and the combined filtrate and wash solution poured into 1N hydrochloric acid (200 ml.) The hydrochloride salt which separates is filtered off and dissolved in hot dilute aqueous sodium hydroxide. The yellow solid which separates on cooling is filtered off, washed with isopropyl alcohol and air-dried. Yield = 3.26 g. (44%), M.P. 229°–242° C.

It is used in Step C without further purification.

C. Ethyl 7-methylthiopyrimido[4,5-b]quinoline-4(3H)-one-2-carboxylate

A round-bottom flask equipped with stirrer, condenser, thermometer and Dean-Stark trap and containing a mixture of 6-methylthio-2-aminoquinoline-3-carboxamide (1.0 g., 4.3 millimoles), diethyl oxalate (20 ml.) and xylene (15 ml.) is immersed in an oil-bath heated to 200° C. Xylene, water and ethanol are distilled from the reaction mixture until the internal temperature of the mixture reaches 165° C. The mixture is stirred at 165° C. for 3 hours and is then poured into chloroform (40 ml.) After cooling to room temperature the mixture is filtered. The brown filter cake is air-dried and then slurried in hot chloroform (100 ml.) to which activated charcoal is added. The slurry is filtered hot and the filtrate evaporated to half-volume and chilled in ice. The yellow solid which precipitates is filtered and dried in air; 142 mg. (11%) M.P. 240°–242° C.

Analysis: Calcd. for $C_{15}H_{13}N_3O_3S$: C, 57.2; H, 4.16; N, 13.33%. Found: C, 56.72; H, 4.13; N, 13.22%.

EXAMPLE XXII

Ethyl 7-Methylsulfinylpyrimido[4,5-b]quinoline-4(3H)-One-2-Carboxylate

A solution of ethyl 7-methylthiopyrimido[4,5-b]quinoline-4-(3H)-one-2-carboxylate (315 mg., 1 millimole) in trifluoroacetic acid (2 ml.) is heated in an oil bath to 55° C. Hydrogen peroxide (113 mg. of 30% $H_2O_2$, 1 millimole) is added and the solution stirred for 10 minutes. After cooling to room temperature, absolute ethanol (6 ml.) is added. The resulting yellow precipitate is filtered off, washed with ether and air-dried. Recrystallization from absolute ethanol gives 185 mg. (56%) of product; m.p. 257°–259° C.

Analysis: Calcd. for $C_{15}H_{13}N_3O_4S$; C, 54.4; H, 3.97; N, 12.7%. Found: C, 54.23; H, 3.97; N, 12.69%.

The thiomethyl compounds of Example XVIII are oxidized to the corresponding sulfinylmethyl compounds by this procedure.

EXAMPLE XXIII

Repetition of the procedures of Examples V-A, XXI-A-C and XXII, but using the appropriate chloro substituted 2-nitrobenzaldehydes as reactants, affords the following compounds:

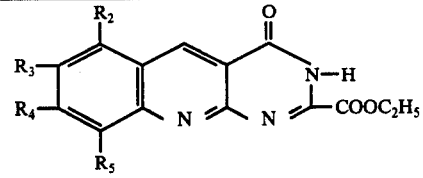

| $R_2$ | $R_3$ | $R_4$ | $R_5$ |
|---|---|---|---|
| H | H | SOCH$_3$ | H |
| SOCH$_3$ | H | H | H |
| H | H | H | SOCH$_3$ |
| H | SOCH$_3$ | SOCH$_3$ | H |
| SOCH$_3$ | H | H | SOCH$_3$ |
| H | SOC$_7$H$_7$ | H | H |
| H | SOC$_7$H$_7$ | C$_2$H$_5$ | H |
| H | H | SOC$_7$H$_7$ | H |
| SOC$_7$H$_7$ | H | H | SOC$_7$H$_7$ |

EXAMPLE XXIV

2-Methyl-7-Hydroxy-8-Methoxypyrimido[4,5-b]Quinoline-4(3H)One

A. 7-Benzyl ether of title compound:

A mixture of 6-benzyloxy-7-methoxy-2-amino-quinoline-3-carboxamide (1.50 g.), concentrated sulfuric acid (0.05 ml.) and acetic anhydride (20 ml.) is heated at 85° C. for 15 minutes. The mixture is then cooled and ice chips added to the reaction mixture. The yellow solid which precipitates is filtered, washed with water, and then with isopropyl alcohol-ether (1:1) and air-dried. Yield = 1.60 g. (99%); m.p. 202°–203° C. (dec.).

B. Debenzylation of 7-benzyl ether.

The 7-benzyl ether from preparation A above is treated with trifluoroacetic acid according to the procedure of Example XV to give the title compound in 95% yield; m.p. 135° C. (dec.).

EXAMPLE XXV

2-Methyl-7,8-Dimethoxypyrimido[4,5-b]Quinolin-4(3H)-One

Concentrated sulfuric acid (1.5 ml.) is added to a slurry of 6,7-dimethoxy-2-aminoquinoline-3-carboxamide (5.0 g., 0.02 mole) and acetic anhydride (40 ml.) The slurry dissolves to give a dark orange solution from which a heavy yellow precipitate separates. Acetic anhydride (10 ml.) is added to facilitate stirring and heating continued for an additional 75 minutes. The mixture is cooled, water (50 ml.) added and the resulting solution made alkaline with 5N sodium hydroxide (225 ml.). It is chilled, the precipitate collected by filtration and air-dried. The yellow solid is recrystallized from ethanol. Yield = 2.37 g., M.P. 300°–302° (dec.).

In like manner, the following compounds are prepared from appropriate reactants:

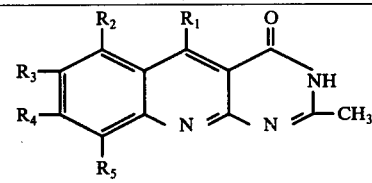

| $R_1$ | $R_2$ | $R_3$ | $R_4$ | $R_5$ |
|---|---|---|---|---|
| H | H | OCH$_3$ | OC$_2$H$_5$ | H |
| H | H | F | H | H |
| H | H | H | F | H |
| H | H | Cl | H | H |

-continued

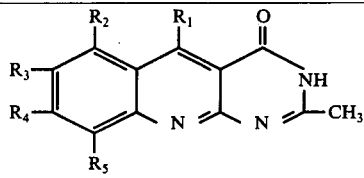

| R₁ | R₂ | R₃ | R₄ | R₅ |
|---|---|---|---|---|
| H | H | H | OCH₃ | H |
| H | H | H | H | OCH₃ |
| H | Cl | H | H | H |
| H | OCH₃ | H | H | OCH₃ |
| H | H | —O—CH₂—O— | | H |
| H | OCH₃ | —O—CH₂—O— | | H |
| H | H | t-C₄H₉ | H | H |
| H | H | —O—CH₂—CH₂—O— | | H |
| H | OCH₃ | OCH₃ | OCH₃ | H |
| H | H | OC₂H₅ | OC₂H₅ | H |
| H | H | CH₃ | CH₃ | H |
| H | Br | H | H | H |
| C₆H₅ | H | H | H | H |
| C₆H₅ | H | OCH₃ | OCH₃ | H |
| C₆H₅ | H | CH₃ | CH₃ | H |
| C₆H₅ | Cl | H | H | H |
| C₆H₅ | H | —O—CH₂—O— | | H |
| C₆H₅ | H | Cl | Br | Cl |
| C₆H₅ | H | t-C₄H₉ | H | H |
| CH₃ | H | H | H | H |
| CH₃ | H | H | OCH₃ | H |
| CH₃ | H | OCH₃ | OC₂H₅ | H |
| CH₃ | OCH₃ | H | H | OCH₃ |
| CH₃ | H | H | CH₃ | H |
| CH₃ | H | H | Cl | H |
| C₂H₅ | H | H | H | H |
| C₂H₅ | H | OCH₃ | OCH₃ | H |
| C₂H₅ | H | C₂H₅ | H | H |
| C₂H₅ | Cl | H | H | H |
| n-C₃H₇ | H | H | H | H |
| n-C₃H₇ | H | OCH₃ | OCH₃ | H |
| n-C₄H₉ | H | H | H | H |
| n-C₄H₉ | H | OCH₃ | OCH₃ | H |
| n-C₄H₉ | OCH₃ | H | H | OCH₃ |
| n-C₄H₉ | H | Cl | H | H |
| n-C₄H₉ | H | n-C₃H₇ | n-C₃H₇ | H |
| n-C₄H₉ | OCH₃ | —O—CH₂—O— | | H |
| n-C₄H₉ | H | SCH₃ | H | H |
| n-C₄H₉ | H | SOCH₃ | H | H |
| CH₃ | H | SCH₃ | H | H |
| CH₃ | H | SOCH₃ | H | H |
| H | H | SCH₃ | H | H |
| H | H | SOCH₃ | H | H |
| H | H | SCH₃ | SCH₃ | H |
| H | H | SOCH₃ | SOCH₃ | H |
| C₆H₅ | H | SCH₃ | H | H |
| C₆H₅ | H | SOCH₃ | H | H |
| C₆H₅ | H | OCH₃ | OC₇H₇ | H |
| CH₃ | CH₃ | CH₃ | CH₃ | OCH₃ |
| CH₃ | H | OCH₃ | H | H |
| H | H | OCH₃ | OC₇H₇ | H |
| H | H | OC₇H₇ | OCH₃ | H |
| H | H | SC₇H₇ | H | H |
| H | H | H | OC₇H₇ | OCH₃ |
| H | H | H | OC₇H₇ | H |
| H | OC₇H₇ | OCH₃ | H | H |
| H | OC₇H₇ | H | H | H |
| H | OC₇H₇ | Br | H | Br |
| H | H | OCH₃ | OC₇H₇ | Br |
| H | C₂H₅ | H | OC₇H₇ | H |
| H | C₂H₅ | OC₇H₇ | H | H |
| H | H | SC₇H₇ | OC₇H₇ | H |
| H | H | OC₇H₅ | SC₇H₇ | H |
| H | H | Br | SC₇H₇ | H |
| H | H | Cl | OC₇H₇ | H |
| H | H | F | OC₇H₇ | H |
| C₆H₅ | OC₇H₇ | OCH₃ | OCH₃ | H |
| C₆H₅ | H | OCH₃ | OC₇H₇ | H |
| C₆H₅ | H | OC₇H₇ | OCH₃ | H |
| C₆H₅ | H | SC₇H₇ | H | H |
| C₆H₅ | H | H | OC₇H₇ | OCH₃ |
| C₆H₅ | H | Cl | OC₇H₇ | H |
| CH₃ | H | OC₇H₇ | OCH₃ | H |
| CH₃ | H | SC₇H₇ | OC₂H₅ | H |
| CH₃ | H | F | OC₇H₇ | H |
| C₂H₅ | H | OC₇H₇ | H | H |
| n-C₃H₇ | H | OC₇H₇ | OCH₃ | H |
| n-C₄H₉ | H | OC₇H₇ | OCH₃ | H |
| n-C₄H₇ | C₂H₅ | SC₇H₇ | H | H |
| n-C₄H₉ | OC₇H₇ | OCH₃ | OCH₃ | H |

The benzyl ethers and benzylthio ethers enumerated above are debenzylated by treatment with trifluoroacetic acid as is described in Example XV.

EXAMPLE XXVI

2-Ethyl-7,8-Dimethoxypyrimidin[4,5-b]quinolin-4(5H)-One

To a stirred mixture of 6,7-dimethoxy-2-aminoquinoline-3-carboxamide (500 mg., 0.002 mole) in propionic anhydride (10 ml.) at 60° C is added concentrated sulfuric acid (0.05 ml). The reaction mixture is stirred for one hour and is then cooled to room temperature and added to water (25 ml). The aqueous mixture is stirred and made basic with 6N sodium hydroxide. It is stirred overnight and then acidified to pH 5.0 with 10% hydrochloric acid. The yellow precipitate which forms is filtered off and recrystallized from ethanol. Yield = 283 mg., M.P. 290°–291° C. (dec.). A second crop of product separates on standing. The two crops are combined and recrystallized from chloroform: ethanol (1:1). Yield = 225 mg (39%), M.P. 293° C.

The following compounds are prepared in like manner from appropriate reactants:

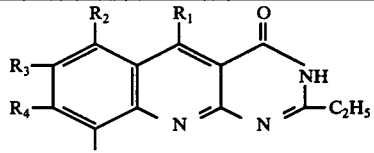

| R₁ | R₂ | R₃ | R₄ | R₅ |
|---|---|---|---|---|
| H | H | H | H | H |
| H | OCH₃ | H | H | H |
| H | H | OCH₃ | H | H |
| H | H | H | OC₂H₅ | H |
| H | H | OCH₃ | OC₂H₅ | H |
| H | H | OC₂H₅ | OC₂H₅ | H |
| H | H | OC₂H₅ | OCH₃ | H |
| H | H | OC₂H₅ | O-(n-C₄H₉) | H |
| H | H | OC₂H₅ | OC₇H₇ | H |
| H | H | H | OCH₃ | OCH₃ |
| H | H | H | OCH₃ | H |
| H | OCH₃ | H | H | OCH₃ |
| H | H | OCH₃ | H | OCH₃ |
| H | H | SCH₃ | H | H |
| H | H | SOCH₃ | H | H |
| H | H | OCH₃ | OCH₃ | OCH₃ |
| H | H | H | F | H |
| H | H | F | H | H |
| H | H | Cl | H | H |
| H | Cl | H | H | H |
| H | H | —O—CH₂—O— | | H |
| H | H | —O—CH₂CH₂—O— | | H |
| H | OCH₃ | —O—CH₂—O— | | H |
| H | H | CH₃ | CH₃ | H |
| H | H | C₂H₅ | H | H |
| H | H | t-C₄H₉ | H | H |
| H | H | CH₃ | H | H |
| H | H | n-C₃H₇ | n-C₃H₇ | H |
| H | Br | H | H | H |
| H | H | Cl | Br | Cl |
| H | H | H | I | H |
| C₆H₅ | H | H | H | H |
| C₆H₅ | H | OCH₃ | OCH₃ | H |
| C₆H₅ | H | CH₃ | CH₃ | H |
| C₆H₅ | Cl | H | H | H |
| C₆H₅ | H | —O—CH₂—O— | | H |
| C₆H₅ | H | t-C₄H₉ | H | H |
| CH₃ | H | OCH₃ | OC₂H₅ | H |
| CH₃ | H | CH₃ | H | H |
| CH₃ | H | H | Cl | H |
| C₂H₅ | H | H | H | H |
| C₂H₅ | H | OCH₃ | OCH₃ | H |
| C₂H₅ | H | n-C₃H₇ | H | H |
| C₂H₅ | H | —O—CH₂—O— | | OCH₃ |
| C₂H₅ | Br | H | H | H |
| n-C₃H₇ | H | —OZ—CH₂CH₂—O— | | H |
| n-C₃H₇ | H | H | OC₂H₅ | H |
| n-C₄H₉ | H | OCH₃ | OCH₃ | H |
| n-C₄H₉ | H | H | i-C₃H₇ | H |

-continued

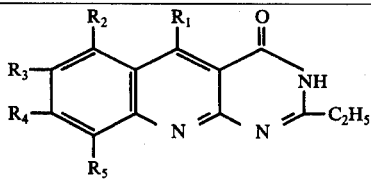

| $R_1$ | $R_2$ | $R_3$ | $R_4$ | $R_5$ |
|---|---|---|---|---|
| n-$C_4H_9$ | H | $SCH_3$ | H | H |
| n-$C_4H_9$ | H | $SOCH_3$ | H | H |
| $CH_3$ | H | —O—(n-$C_4H_9$) | —O—(n-$C_4H_9$) | H |
| $C_6H_5$ | H | $SCH_3$ | $SCH_3$ | H |
| $C_6H_5$ | H | $SOCH_3$ | $SOCH_3$ | H |
| H | H | $OCH_3$ | $OC_7H_7$ | H |
| H | H | $OC_7H_7$ | $OCH_3$ | H |
| H | H | $OC_7H_7$ | H | H |
| H | H | F | $OC_7H_7$ | H |
| H | H | Cl | $OC_7H_7$ | H |
| H | $C_2H_5$ | H | $OC_7H_7$ | H |
| H | $OC_7H_7$ | $OCH_3$ | $OCH_3$ | H |
| $C_6H_5$ | H | $OC_7H_7$ | $OCH_3$ | H |
| $C_6H_5$ | H | $OC_7H_7$ | H | H |
| $C_6H_5$ | $OC_7H_7$ | Br | H | Br |
| $CH_3$ | H | $OC_7H_7$ | $OCH_3$ | H |
| $CH_3$ | H | $OCH_3$ | $OC_7H_7$ | H |
| $CH_3$ | H | $OC_7H_7$ | $OC_2H_5$ | H |
| $CH_3$ | H | $OCH_3$ | $OC_7H_7$ | Br |
| $C_2H_5$ | H | F | $OC_7H_7$ | H |
| $C_2H_5$ | H | $OC_7H_7$ | $OCH_3$ | H |
| $C_2H_5$ | $OC_2H_7$ | $OCH_3$ | H | H |
| n-$C_3H_7$ | H | $OC_7H_7$ | $OC_2H_5$ | H |
| i-$C_3H_7$ | H | $OC_7H_7$ | $OC_2H_5$ | H |
| n-$C_4H_9$ | H | $OC_7H_7$ | H | H |
| n-$C_4H_9$ | $C_2H_5$ | $OC_7H_7$ | H | H |
| n-$C_4H_9$ | H | $OC_7H_7$ | $OCH_3$ | H |

Debenzylation of the benzyl ethers cited above by reaction with trifluoroacetic acid according to the procedure of Example XV affords the corresponding hydroxy compounds.

EXAMPLE XXVII

2-Acetyl-7,8-Dimethoxypyrimido[4,5-b]quinoline-4(3H)-One

To a solution of selenium dioxide-(24.5 mg., 2.2 millimoles) in dioxane water (11 ml. of 10:1) is added 2-ethyl-7-S-dimethoxypyrimido) [4,5-b] quinolin-4(3H)-one (125 mg., 4.4millimoles). The mixture is heated to reflux for 48 hours after which more selenium dioxide (24.5 mg.) is added and refluxing continued for an additional 24 hours. The mixture is cooled, the selenium filtered off and the filtrate concentrated to dryness. The residue is taken up in ethanol/chloroform (1:99) and chromatographedonea column of silica using the same solvent as eluant (250 ml.) followed by ethanol/chloroform (2:98). Concentration of the second eluate (625 ml.) gives a yellow solid (23 mg.); M.P. 300° C. [dec.].

Similarly, the remaining 2-ethyl derivatives of Example XXVI are oxidized to their corresponding 2-acetyl derivatives.

EXAMPLE XXVIII

Ethyl 5-Phenylpyrimido[4,5-b]Quinolin-4(3H)-One-2-Carboxylate

A mixture of 2-amino-4-phenylquinoline-3-carboxamide (263 mg., 1.0 millimole), diethyl oxalate (5 ml.) acetic acid (5 ml.) is heated to reflux overnight. It is then cooled, diluted with ether (50 ml.) and the brown solid which forms filtered off. The filtrate is evaporated in vacuo and the oily residue triturated with saturated aqueous sodium bicarbonate solution. The resulting solid (110 mg.) is recovered by filtration and recrystal-lized from hot ethyl acetate (8 ml.). A small amount of insoluble material is filtered off from the hot solution. Upon cooling, the title product separates as crystals (25 mg.). M.P. = 255° C. (dec.).

Analysis: Calcd. for $C_{20}H_{15}N_3O_3$: C, 69.55; H, 4.38; N, 12.17%. Found*: C, 69.94; H, 4.31; N, 12.17%. (* - average of 2 analyses.)

In like manner, the 2-amino-4-substituted-quinoline-3-carboxamides of Preparation D are converted to ethyl 5-substituted-pyrimido[4,5-b]-quinolin-4-(3H)-one-2-carboxylates of the formula

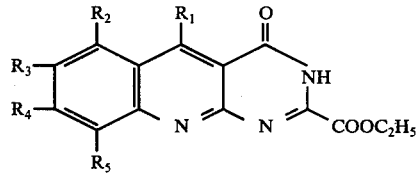

wherein the R variables have the values given in Preparation D.

The esters thus obtained are transformed to the corresponding amide and hydroxamic acid derivatives by the procedures of Examples VII and XIV, respectively.

EXAMPLE XXIX

Ethyl 3-Methyl-7,8-Dimethoxypyrimido[4,5-b]quinolin-4-(3H)-One-2-Carboxylate

Sodium hydride (470 mg. of 50% in oil, 0.011 mole) is added to a slurry of ethyl 7,8-dimethoxypyrimido [4,5-b]quinolin-4(3H)-one-2-carboxylate (3.3 g., 0.01 mole) in N,N-dimethylformamide (75 ml.). The mixture is stirred and heated on a steambath for ten minutes and then at room temperature for a half hour. It is cooled in an ice-bath and iodomethane (2.1 g., 0.015 mole) added dropwise over a 30 minute period. Following completion of addition, the mixture is stirred for an additional 15 minutes in an ice-bath and then for a half-hour at room temperature. The reaction mixture is poured into ice-water (200 ml.) and the resulting solid filtered off, air-dried and recrystallized from ethanol to give 2.1 g. of yellow crystals (61.2%); m.p. 211.5° C. (dec.)

Analysis: Calcd. for $C_{17}H_{17}N_3O_5$: C, 59.47; H, 4.99, N, 12.24%. Found: C, 59.55; H, 5.02; N, 12.45%.

In like manner, but using the appropriate compound of formula I (Y=H) and the appropriate alkyl iodide, the products of Examples I and II–XXVIII are converted to their corresponding 3-methyl, 3-ethyl, 3-n-propyl, 3-isopropyl and 3-n-butyl derivatives.

Compounds wherein one of $R_2$, $R_3$, $R_4$, or $R_5$ is thiol or hydroxy are obtained by debenzylation of the corresponding benzylthio ethers or benzylethers by reaction with trifluoroacetic acid according to the procedure of Example XV.

EXAMPLE XXX

Ethyl 3-Carbethoxymethyl-7,8-Dimethoxypyrimido[4,5-b]quinolin-4(3H)-One-2-Carboxylate To a slurry of ethyl 7,8-dimethoxypyrimido[4,5-b]quinolin-4-(3H)-one-2-carboxylate (1.6g., 5.0 millimoles) in N,N-dimethylformamide(30ml.) is added sodium hydride (235 mg., 5.5 millimoles of 56% in oil). The slurry is heated on a steambath for 10 minutes and then cooled to room temperature. Ethyl bromoacetate (968 mg., 5.8 millimoles) is added and the reaction mixture heated on a streambath for one hour. After standing overnight at room temperature the mixture is diluted with water (75 ml.) and the resulting yellow solid filtered off (1.4g.). It is purified by chromatography on a column of silica gel using chloroform as solvent and eluant. The eluate (300 ml.) is evaporated to give 1.2g. of yellow solid. It is recrystallized from hot ethanol (50 ml.) containing sufficient chloroform to achieve solution. Yield = 900 mg. of fluffy yellow crystals (43.4%); m.p. 198°–199° C. (dec.)

Analysis: Calcd. for $C_{20}H_{21}N_3O_7$: C, 57.83; H, 5.10; N, 10.12% , Found: c, 59.67; H, 4.99; N, 9.90%,

EXAMPLE XXXI

Ethyl 3-(3-Carbethoxypropyl)-7,8-Dimethoxypyrimido[4,5-b]quinolin-4-(3H)-One 2-Carboxylate The procedure of Example XXX is repeated but using ethyl four-bromobutyrate (1.1 g., 5.8 millimole) in place of ethyl bromoacetate. The solid obtained upon diluting the reaction mixture with water is filtered off, dried and recrystallized from benzene: hexane (40 ml. of 1:1) to give 615 mg. (29.1%) of the title compound as fluffy yellow crystals; M.P. 144°–146° C Analysis: Calcd. for $C_{22}H_{25}N_3O_7$: C, 59.58; H, 5.68; N, 9.48%. Found: C, 59.84; H, 5.98, H, 9.61%.

EXAMPLE XXXII

Pyrimido [4,5-b]quinolin-4(3H)-one compounds of Examples I-XXVIII are alkylated substantially according to the procedure of Example XXXI but using the appropriate alkyl bromoalkanoate in place of ethyl 4-bromo butyrate. The products are recrystallized from suitable solvents such as ethanol or benzene: hexane (1:1).

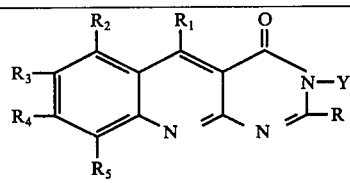

| Y | R | $R_1$ | $R_2$ | $R_3$ | $R_4$ | $R_5$ |
|---|---|---|---|---|---|---|
| $CH_2COOCH_3$ | $COOC_2H_5$ | H | H | H | H | H |
| $CH_2COO$-n-$C_4H_9$ | $COOC_2H_5$ | H | H | H | H | H |
| $CH_2COOC_2H_5$ | COO-n-$C_4H_9$ | H | H | $OCH_3$ | $OCH_3$ | H |
| $CH_2COO$-n-$C_3H_7$ | $COOC_2H_5$ | H | H | OCH | H | $OCH_3$ |
| $CH_2CH_2COOCH_3$ | $COOC_2H_5$ | H | $OCH_3$ | H | H | $OCH_3$ |
| $CH_2CH_2COO$-n-$C_3H_7$ | $COOC_2H_5$ | H | H | $OCH_3$ | $OCH_3$ | H |
| $(CH_2)_4COOC_2H_5$ | $COOC_2H_5$ | H | H | $OCH_3$ | $OCH_3$ | $OCH_3$ |
| $(CH_2)_4COO$-n-$C_4H_9$ | $COOC_2H_5$ | H | H | $OC_2H_5$ | O-n-$C_4H_9$ | H |
| $CH_2COOC_2H_5$ | $COOC_2H_5$ | H | H | $OC_2H_5$ | $OC_7H_7$ | H |
| $(CH_2)_3COOCH_3$ | $COOC_2H_5$ | H | $OC_2H_5$ | H | H | H |
| $CH_2COOC_2H_5$ | $COOC_2H_5$ | H | H | —$OCH_2CH_2O$— | | H |
| $CH_2COOCH_3$ | $COOC_2H_5$ | H | H | F | H | H |
| $CH_2CH_2COOC_2H_5$ | $COOC_2H_5$ | H | H | H | F | H |
| $CH_2COO$-i-$C_3H_7$ | $COOC_2H_5$ | H | H | Cl | H | H |
| $CH_2CH_2COOCH_3$ | $COOC_2H_5$ | H | H | —$OCH_2O$— | | H |
| $CH_2COOCH_3$ | Coo-n-$C_4H_9$ | H | H | H | H | H |
| $CH_2CH_2COOCH_3$ | $COOC_2H_5$ | H | Cl | H | H | H |
| $CH_2COO$-i-$C_3H_7$ | $COOC_2H_5$ | H | H | H | $OCH_3$ | $OCH_3$ |
| $CH_2COOC_2H_5$ | $COOCH_2CH_2OH$ | H | H | $OCH_3$ | $OCH_3$ | H |
| $(CH_2)_3COOCH_3$ | $COOC_2H_5$ | H | H | O-n-$C_4H_9$ | O-n-$C_4H_9$ | H |
| $CH_2CH_2COOCH_3$ | $COOC_2H_5$ | H | $OCH_3$ | —$O$—$CH_2$—$O$— | | H |
| $CH_2COOC_2H_5$ | $COOC_2H_5$ | H | H | Br | H | Br |
| $(CH_2)_4COOC_2H_5$ | $COOC_2H_5$ | H | Cl | H | H | Cl |
| $(CH_2)_3COO$-n-$C_3H_7$ | COO-i-$C_3H_7$ | H | H | $CH_3$ | H | H |
| $CH_2CH_2COOC_2H_5$ | $COOC_2H_5$ | H | H | H | $CH_3$ | H |
| $CH_2COOC_2H_5$ | $COOC_2H_5$ | H | H | t-$C_4H_9$- | H | H |
| $CH_2COOCH_3$ | $COOCH_3$ | H | $CH_3$ | H | $CH_3$ | H |
| $CH_2COOC_2H_5$ | $COOC_2H_5$ | H | H | n-$C_3H_7$ | H | H |
| $CH_2COOC_2H_5$ | $COOC_2H_5$ | H | H | $SCH_3$ | H | H |
| $CH_2COOC_2H_5$ | $COOC_2H_5$ | $C_6H_5$ | H | H | H | H |
| $CH_2COOC_2H_5$ | $COOC_2H_5$ | $C_6H_5$ | H | $OCH_3$ | $OCH_3$ | H |
| $(CH_2)_3COOCH_3$ | $COOC_2H_5$ | $CH_3$ | H | $OCH_3$ | $OCH_3$ | H |
| $(CH_2)_4COOC_2H_5$ | $COOC_2H_5$ | $CH_3$ | H | H | $OC_2H_5$ | $OC_2H_5$ |
| $CH_2COO$-n-$C_4H_9$ | $COOC_2H_5$ | $CH_3$ | H | $CH_3$ | $CH_3$ | H |
| $CH_2CH_2COOC_2H_5$ | $COOC_2H_5$ | n-$C_3H_7$ | H | Cl | H | H |
| $CH_2COO$-n-$C_3H_7$ | $COOC_2H_5$ | $CH_3$ | H | Cl | $CH_3$ | H |
| $CH_2COOn$-$C_4H_9$ | $COOC_2H_5$ | n-$C_4H_9$ | H | H | H | H |
| $(CH_2)_3COOC_2H_5$ | $COOC_2H_5$ | $C_2H_5$ | H | Br | H | H |
| $CH_2COOCH_3$ | $COOC_2H_5$ | $C_6H_5$ | H | F | H | H |
| $CH_2COOC_2H_5$ | $COOC_2H_5$ | $CH_3$ | H | —$OCH_2CH_2$—$O$— | | H |
| $CH_2COOC_2H_5$ | $COOC_2H_5$ | $C_6H_5$ | H | —$O$—$CH_2$—$O$— | | H |
| $CH_2COOC_2H_5$ | $COOCH_2CH_2OH$ | H | H | $OCH_3$ | $OCH_3$ | H |
| $CH_2COOC_2H_5$ | $COO(CH_2)_3OH$ | H | H | $OC_2H_5$ | $OCH_3$ | H |
| $CH_2COOCH_3$ | $COO(CH_2)_4OH$ | H | H | H | H | H |
| $CH_2COOCH_2CH_2OH$ | $COOCH_2CH_2OH$ | H | H | $OCH_3$ | $OCH_3$ | H |
| $CH_2COOC_2H_5$ | $CH_3$ | H | H | $OCH_3$ | $OCH_3$ | H |
| $(CH_2)_3COOC_2H_5$ | $CH_3$ | H | Cl | H | H | H |
| $CH_2COOCH_3$ | $CH_3$ | H | H | F | H | H |
| $(CH_2)_2COOC_2H_5$ | $CH_3$ | H | H | —$O$—$CH_2$—$O$— | | H |
| $CH_2COOC_2H_5$ | $CH_3$ | H | H | t-$C_4H_9$ | H | H |
| $CH_2COOC_2H_5$ | $CH_3$ | $C_6H_5$ | H | $SCH_3$ | H | H |
| $CH_2CH_2COOCH_3$ | $C_2H_5$ | H | H | $OCH_3$ | $OCH_3$ | H |
| $CH_2COOC_2H_5$ | $C_2H_5$ | H | Cl | Br | Cl | H |

-continued

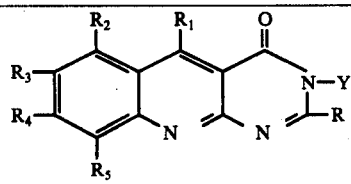

| Y | R | R₁ | R₂ | R₃ | R₄ | R₅ |
|---|---|----|----|----|----|-----|
| CH₂COOC₂H₅ | C₂H₅ | n-C₄H₉ | H | SOCH₃ | H | H |
| CH₂COOCH₃ | COCH₃ | H | H | OCH₃ | OCH₃ | H |
| (CH₂)₂COOCH₃ | COCH₃ | H | Cl | H | H | H |
| (CH₂)₂COOCH₃ | COCH₃ | H | C₆H₅ | H | CH₃ | H |
| (CH₂)₃COOC₂H₅ | COCH₃ | C₂H₅ | H | H | H | H |
| CH₂COOCH₃ | COOC₂H₅ | H | H | OC₇H₇ | OCH₃ | H |
| (CH₂)₂COOC₂H₅ | COO-n-C₄H₉ | H | H | OC₇H₇ | OCH₃ | H |
| CH₂COO-n-C₄H₉ | COOC₂H₅ | H | H | OC₇H₇ | H | H |
| (CH₂)₃COOC₂H₅ | COOC₂H₅ | H | H | OCH₃ | OC₇H₇ | H |
| CH₂COOC₂H₅ | COOCH₃ | H | H | OC₇H₇ | OC₇H₇ | H |
| (CH₂)₄COOCH₃ | COOC₂H₅ | H | OC₇H₇ | OCH₃ | OCH₃ | H |
| (CH₂)₂COO-n-C₄H₉ | COO-n-C₄H₉ | H | H | H | H | OC₇H₇ |
| CH₂COO-n-C₃H₇ | COO-n-C₃H₇ | H | C₂H₅ | OC₇H₇ | H | H |
| CH₂COOC₂H₅ | COOC₂H₅ | H | H | Br | OC₇H₇ | H |
| CH₂COOC₂H₅ | COOCH₃ | H | H | Cl | OC₇H₇ | H |
| CH₂COOCH₃ | COOCH₂CH₂OH | H | H | OC₇H₇ | OCH₃ | H |
| CH₂COOCH₃ | COOCH₂CH₂OH | H | H | OCH₃ | OC₇H₇ | H |
| (CH₂)₂COOC₂H₅ | COO(CH₂)₄OH | H | H | OC₇H₇ | H | H |
| CH₂COO-n-C₄H₉ | COO(CH₂)₃OH | H | H | F | OC₇H₇ | H |
| CH₂COOC₂H₅ | CH₃ | H | H | OC₇H₇ | OCH₃ | H |
| CH₂COOC₂H₅ | CH₃ | H | H | OC₂H₅ | OC₇H₇ | H |
| CH₂COOC₂H₅ | CH₃ | H | OC₇H₇ | OCH₃ | H | H |
| CH₂COOC₂H₅ | C₂H₅ | H | H | OC₇H₇ | H | H |
| CH₂COOC₂H₅ | C₂H₅ | H | H | OCH₃ | OC₇H₇ | Br |
| CH₂COOC₂H₅ | C₂H₅ | H | H | Br | OC₇H₇ | H |
| CH₂COOC₂H₅ | COCH₃ | H | H | OC₇H₇ | OCH₃ | H |
| CH₂COOC₂H₅ | COCH₃ | H | C₂H₅ | H | OC₇H₇ | H |
| CH₂COOCH₃ | CH₃ | C₆H₅ | H | OC₇H₇ | OCH₃ | H |
| (CH₂)₃COOC₂H₅ | C₂H₅ | C₂H₅ | OC₇H₇ | OCH₃ | H | H |
| (CH₂)₂COO-n-C₄H₉ | CH₃ | n-C₄H₉ | C₂H₅ | OC₇H₇ | H | H |
| CH₂COOC₂H₅ | CH₃ | CH₃ | H | OC₇H₇ | OCH₃ | H |
| CH₂COOCH₃ | COOC₂H₅ | H | H | SC₇H₇ | H | H |
| (CH₂)₄COOC₂H₅ | COOC₂H₅ | H | H | H | H | SC₇H₇ |
| CH₂COOC₂H₅ | COOC₂H₅ | H | H | SC₇H₇ | C₂H₅ | H |
| (CH₂)₂COO-n-C₄H₉ | COOC₂H₅ | H | H | H | SC₇H₇ | H |
| CH₂COOCH₃ | COOC₂H₅ | H | SC₇H₇ | H | H | SC₇H₇ |
| CH₂COOCH₃ | COOC₂H₅ | H | SOC₇H₇ | H | H | H |
| (CH₂)₃COO-i-C₃H₇ | COOC₂H₅ | H | H | SOC₇H₇ | C₂H₅ | H |
| CH₂CH₂COOC₂H₅ | COOC₂H₅ | H | H | SOC₇H₇ | H | H |
| CH₂COOCH₃ | COOC₂H₅ | H | H | CH₃COO | OCH₃ | H |
| (CH₂)₄COOC₂H₅ | COOC₂H₅ | H | H | OCH₃ | C₆H₅COO | H |

The benzyl ethers and benzylthio ethers tabulated above are converted to the corresponding hydroxy and thiol compounds by reaction with trifluoroacetic acid according to the procedure of Example XV.

EXAMPLE XXXIII

Ethyl 3-Acetoxyethyl-7,8-Dimethoxypyrimidin [4,5-b]quinolin-4(3H)-One-2-Carboxylate The procedure of Example XXX is repeated by using bromoethyl acetate, (969mg., 5.8 millimoles) as alkylating agent in place of ethyl bromoacetate. The solid product which separates upon dilution of the reaction mixture with water is filtered off, dried and recrystallized from ethanol (20 ml.) containing sufficient acetonitrile to achieve solution. Yield = 550 mg. (26.5%); M.P. 195°–196°C. (dec.)

Analysis: Calcd. $C_{20}H_{21}N_3O_7$: C, 57.83; H, 5.10; N, 10.12% Found C, 57-95; H, 5.14; N, 10.31%

In like manner, the following compounds are prepared from the appropriate pyrimidin[]4,5-b]quinolin-4(3H)-one compounds of Example I-XXVIII and the appropriate bromoalkanoate or bromoalkyl benzoate:

| Y | R | R₁ | R₂ | R₃ | R₄ | R₅ |
|---|---|----|----|----|----|-----|
| CH₂CH₂OCOCH₃ | COOC₂H₅ | H | H | OC₂H₅ | H | H |
| CH₂CH₂OCOC₂H₅ | COOC₂H₅ | H | H | H | OCH₃ | H |
| CH₂CH₂OCOCH₃ | COOC₂H₅ | H | H | —O—CH₂—O— | | H |
| (CH₂)₃OCOCH₃ | COOC₂H₅ | H | H | OC₂H₅ | OC₇H₇ | H |
| (CH₂)₄OCOC₂H₅ | COOC₂H₅ | H | OCH₃ | H | H | OCH₃ |
| CH₂CH₂OCOC₆H₅ | COOC₂H₅ | H | H | OCH₃ | OCH₃ | H |
| CH₂CH₂OCOC₃H₇ | COOC₂H₅ | H | H | F | H | H |
| (CH₂)₃OCOC₂H₅ | COOC₂H₅ | C₂H₅ | H | H | Cl | H |
| CH₂CH₂OCOCH₃ | COOCH₂CH₂OH | H | H | OCH₃ | OCH₃ | H |
| CH₂CH₂OCOC₂H₅ | COOC₂H₅ | H | H | SCH₃ | H | H |

-continued

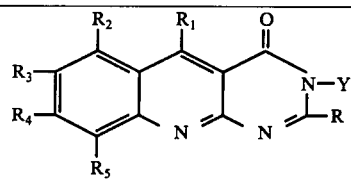

| Y | R | R₁ | R₂ | R₃ | R₄ | R₅ |
|---|---|---|---|---|---|---|
| CH₂CH₂OCOC₂H₅ | COOC₁H₅ | H | H | SOCH₃ | H | H |
| (CH₂)₄OCOC₄H₉ | COOC₂H₅ | C₆H₅ | H | H | H | H |
| CH₂CH₂OCOCH₃ | COO-n-C₄H₉ | H | H | OCH₃ | OCH₃ | H |
| CH₂CH₂OCOC₂H₅ | COOC₂H₅ | H | H | OCH₃ | H | OCH₃ |
| (CH₂)₃OCOCH₃ | COOC₂H₅ | H | H | OC₂H₅ | O-n-C₄H₉ | H |
| CH₂CH₂OCOC₃H₇ | COOC₂H₅ | H | H | —OCH₂CH₂O— | | H |
| (CH₂)₄OCOCH₃ | COOC₂H₅ | H | H | H | F | H |
| CH₂CH₂OCOC₂H₅ | COOC₂H₅ | H | Cl | H | H | H |
| CH₂CH₂OCOC₄H₉ | COO-n-C₄H₉ | H | H | H | H | H |
| CH₂CH₂OCOCH₃ | COOC₂H₅ | H | H | OCH₃ | OCH₃ | OCH₃ |
| (CH₂)₃OCOC₂H₅ | COOC₂H₅ | H | Br | H | H | H |
| CH₂CH₂OCOCH₃ | COOCH₃ | H | CH₃ | H | CH₃ | H |
| CH₂CH₂OCOC₃H₇ | COOC₂H₅ | H | H | t-C₄H₉ | H | H |
| (CH₂)₄OCOCH₃ | COOC₂H₅ | H | H | n-C₃H₇ | n-C₃H₇ | H |
| CH₂CH₂OCOC₂H₅ | CH₃ | H | H | OCH₃ | OCH₃ | H |
| CH₂CH₂OCOCH₃ | CH₃ | CH₃ | H | OCH₃ | OC₂H₅ | H |
| (CH₂)₃OCOCH₃ | CH₃ | n-C₄H₉ | H | H | H | H |
| CH₂CH₂OCOC₂H₅ | CH₃ | H | H | SCH₃ | SCH₃ | H |
| CH₂CH₂OCOC₂H₅ | CH₃ | H | H | SOCH₃ | SOCH₃ | H |
| CH₂CH₂OCOC₂H₅ | CH₃ | C₂H₅ | Cl | H | H | H |
| CH₂CH₂OCOCH₃ | CH₃ | C₆H₅ | H | OCH₃ | OCH₃ | H |
| (CH₂)₄OCOCH₃ | CH₃ | C₆H₅ | H | SCH₃ | H | H |
| (CH₂)₃OCOC₂H₅ | C₂H₅ | H | H | H | H | H |
| (CH₂)₃OCOC₄H₉ | C₂H₅ | H | H | OCH₃ | OCH₃ | H |
| CH₂CH₂OCOCH₃ | C₂H₅ | H | H | Cl | H | H |
| CH₂CH₂OCOC₂H₅ | C₂H₅ | H | H | OC₂H₅ | OC₇H₇ | H |
| (CH₂)₃OCOC₂H₅ | C₂H₅ | H | H | OC₂H₅ | o-n-C₄H₉ | H |
| (CH₂)₃OCOC₂H₅ | C₂H₅ | H | OCH₃ | —O—CH₂—O— | | H |
| CH₂CH₂OCOC₂H₅ | C₂H₅ | C₂H₅ | H | SCH₃ | SCH₃ | H |
| CH₂CH₂OCOCH₃ | C₂H₅ | n-C₄H₉ | H | H | i-C₃H₇ | H |
| CH₂CH₂OCOC₂H₅ | C₂H₅ | CH₃ | H | O-n-C₄H₉ | O-n-C₄H₉ | H |
| CH₂CH₂OCOCH₃ | C₂H₅ | C₆H₅ | H | SOCH₃ | SOCH₃ | H |
| (CH₂)₃OCOCH₃ | COCH₃ | H | H | OCH₃ | OCH₃ | H |
| (CH₂)₃OCOCH₃ | COCH₃ | H | H | —OCH₂CH₂O— | | H |
| CH₂CH₂OCOCH₃ | COCH₃ | H | H | CH₃ | CH₃ | H |
| CH₂CH₂OCOCH₃ | COCH₃ | CH₃ | H | H | Cl | H |
| CH₂CH₂OCOCH₃ | COCH₃ | C₂H₅ | Br | H | H | H |
| CH₂CH₂OCOCH₃ | COCH₃ | n-C₄H₉ | H | H | i-C₃H₇ | H |
| CH₂CH₂OCOCH₃ | COCH₃ | C₆H₅ | H | SOCH₃ | SOCH₃ | H |
| CH₂CH₂OCOC₆H₅ | COOC₂H₅ | H | H | OCH₃ | OCH₃ | H |
| (CH₂)₄OCOC₆H₅ | COOC₂H₅ | H | H | —O—CH₂—O— | | H |
| CH₂CH₂OCOC₆H₅ | H | H | H | OC₂H₅ | OC₇H₇ | H |
| (CH₂)₃OCOC₆H₅ | COOC₂H₅ | CH₃ | H | SCH₃ | H | H |
| CH₂CH₂OCOC₆H₅ | CH₃ | C₆H₅ | CH₃ | CH₃ | CH₃ | OCH₃ |
| (CH₂)₄OCOC₆H₅ | CH₃ | CH₃ | H | SOCH₃ | H | H |
| CH₂CH₂OCOC₆H₅ | C₂H₅ | H | H | OC₂H₅ | O-(n-C₄H₉)H | H |
| CH₂CH₂OCOC₆H₅ | COOC₂H₅ | H | H | OC₇H₇ | OCH₃ | H |
| CH₂CH₂OCOC₆H₅ | COO-n-C₄H₉ | H | H | OC₇H₇ | OCH₃ | H |
| CH₂CH₂OCOCH₃ | COOC₂H₅ | H | H | OCH₃ | OC₇H₇ | H |
| (CH₂)₄OCOC₂H₇ | COOC₂H₅ | H | H | OC₇H₇ | H | H |
| (CH₂)₃OCOC₆H₅ | COOC₂H₅ | H | OC₇H₇ | OCH₃ | H | H |
| CH₂CH₂OCOC₂H₅ | COOC₂H₅ | H | H | F | OC₇H₇ | H |
| CH₂CH₂OCOCH₃ | CH₃ | H | H | OC₇H₇ | OCH₃ | H |
| (CH₂)₃OCOC₆H₅ | CH₃ | C₆H₅ | H | OCH₃ | OCH₃ | H |
| CH₂CH₂OCOCH₃ | CH₃ | n-C₄H₉ | C₂H₅ | OC₇H₇ | H | H |
| CH₂CH₂OCOC₃H₇ | C₂H₅ | H | H | OC₇H₇ | OC₇H₇ | H |
| CH₂CH₂OCOCH₃ | C₂H₅ | CH₃ | H | OCH₃ | OC₇H₇ | Br |
| CH₂CH₂OCOCH₃ | COCH₃ | H | H | OC₇H₇ | OCH₃ | H |
| CH₂CH₂OCOC₆H₅ | COOCH₂CH₂OH | H | H | OC₇H₇ | OCH₃ | H |
| CH₂CH₂OCOCH₃ | COOC₂H₅ | H | H | SC₇H₇ | H | H |
| (CH₂)₄OCOC₂H₅ | COOC₂H₅ | H | H | SC₇H₇ | C₂H₅ | H |
| CH₂CH₂OCOC₆H₅ | COOC₂H₅ | H | H | H | SC₇H₇ | H |
| CH₂CH₂OCOC₃H₇ | COOC₂H₅ | H | H | SOC₇H₇ | H | H |
| CH₂CH₂OCOC₆H₅ | COOC₂H₅ | H | H | H | SOC₇H₇ | H |
| CH₂CH₂OCOCH₃ | COO-n-C₄H₉ | H | H | CH₃COO | OCH₃ | H |
| (CH₂)₄OCOC₂H₅ | COOC₂H₅ | H | H | C₃H₇COO | OCH₃ | H |
| CH₂CH₂OCOC₆H₅ | COOCH₃ | H | HCOO | OCH₃ | H | H |
| (CH₂)₃OCOCH₃ | COOC₂H₅ | H | H | H | C₂H₅COS | H |
| CH₂CH₂OCOC₃H₇ | COOC₂H₅ | H | H | C₆H₅COO | OCH₃ | H |
| CH₂CH₂OCOCH₃ | COOC₂H₅ | H | H | CH₃COO | H | H |
| (CH₂)₄OCOC₂H₅ | COOC₂H₅ | H | H | C₆H₅COO | H | H |

EXAMPLE XXXIV

Ethyl Benzo[g]Quinazolin-4(3H)-One-2-Carboxylate

A. Benzo-isatoic Anhydride

Anthranilic acid (25.0 g., 0.135 mole) is dissolved, warming if necessary, in a mixture of water (50 ml.), concentrated hydrochloric acid (50 ml.) and dioxane (100 ml.). Phosgene is passed into the solution with good stirring at such a rate that bubbles of the gas escape slowly into an ammonia scrubber attached to the reaction flask. The temperature is held below 50° C. by regulating the rate of introduction of the phosgene. After passing phosgene into the mixture for four hours, the residual phosgene is blown out by passing air through the mixture. The mixture is cooled and the product filtered off, washed with cold water and dried to give 26.46 g. (93.5%) of the anhydride. M.P. 390° C. (dec.).

B. 2-Aminonaphthalene-3-Carboxamide

Ammonia is intermittently bubbled into a suspension of benzoisatoi anhydride (5.0 g., 2.25 millimoles) and ethanol (80 ml.) for a period of two days. The bright green solid which formed is filtered from the reaction mixture, dried and then recrystallized from ethanol. Yield = 1.95 g. (46%) of the title amide. M.P. 234°–235° C. (m/e - 186).

C. Ethyl benzo[g]quinazolin-4(3H)-one-2carboxylate

Diethyl oxalate (2.35 g., 16.1 millimoles), sodium methoxide (10 mg) and 2-aminonaphthalene-3-carboxamide (1.50 g., 8.05 millimoles) are mixed together and heated at reflux for two days. The mixture is then cooled in an ice bath and the brown precipitate recovered by filtration. It is recrystallized from ethanol to give 1.76 g. (79% yield) of the desired ester. M.P. 240°–242° C.

Analysis: Calcd. for $C_{15}H_{12}N_2O_3$: C, 67.5; H, 4.51; N, 10.44%. Found: C, 65.44; H, 4.50; N, 10.17%.

D. The ester is hydrolyzed to the disodium salt as follows:

The ester (1.05 g., 3.92 millimoles) is added to 15% aqueous sodium hydroxide (20 ml.) and the mixture stirred for 2 days. It is then acidified at room temperature with 10% hydrochloric acid to pH 2. and evaporated to dryness under reduced pressure. The residue is treated with methanol-water (1:1, 50 ml.) and the suspension filtered to give 0.70 g. of yellow crystals. The crystals are added to a saturated solution of aqueous sodium bicarbonate (35 ml.) and water (20 ml.). The mixture is stirred for a half-hour and the yellow solid filtered of and dried. Yield = 0.641 g. (54.7%). M.P. 340° C. (dec.).

Analysis: Calcd. for $C_{13}H_6N_2O_3 \cdot 2Na \cdot H_2O$: C, 51.31; H, 3.28; N, 9.06; Na, 14.10% Found: C, 51.34; H, 3.05; N, 9.24; Na, 11.13%

E. Repetition of this hydrolysis procedure but using potassium bicarbonate or ammonium bicarbonate in place of sodium bicarbonate affords the dipotassium salt and the diammonium salt.

EXAMPLE XXXV

Alkyl Benzo[g]Quinazolin-4(3H)-One-2-Carboxylates

The following alkyl benzo[g]quinazolin-4(3H)one-2-carboxylates are prepared from the appropriate reactants by the procedure of Example XXXIV.

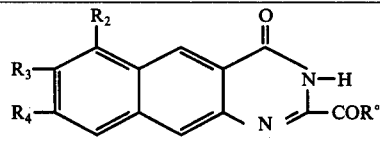

| R° | $R_2$ | $R_3$ | $R_4$ |
|---|---|---|---|
| $OC_2H_5$ | H | H | $OC_2H_5$ |
| $OCH_3$ | H | $OCH_3$ | $OCH_3$ |
| $O-n-C_4H_9$ | H | $OCH_3$ | $OCH_3$ |
| $OC_2H_5$ | H | —O—$CH_2$—O— | |
| $OC_2H_5$ | H | H | $O-n-C_4H_9$ |
| $OC_2H_5$ | H | $O-n-C_3H_7$ | $O-n-C_3H_7$ |
| $OCH_3$ | H | $CH_3$ | H |
| $O-i-C_3H_7$ | H | H | $CH_3$ |
| $OC_2H_5$ | $CH_3$ | H | H |
| $OC_2H_5$ | $CH_3$ | $CH_3$ | H |
| $OC_2H_5$ | H | $CH_3$ | $CH_3$ |

-continued

| R° | $R_2$ | $R_3$ | $R_4$ |
|---|---|---|---|
| $O-n-C_3H_7$ | H | H | $C_2H_5$ |
| $O-n-C_3H_7$ | H | H | $n-C_3H_7$ |
| $O-n-C_4H_9$ | H | H | $i-C_3H_7$ |
| $OCH_3$ | H | $n-C_3H_7$ | H |
| $OCH_3$ | H | $n-C_3H_7$ | $n-C_3H_7$ |
| $OC_2H_5$ | H | $t-C_4H_9$ | H |
| $OC_2H_5$ | $CH_3$ | H | $CH_3$ |
| $OCH_3$ | H | H | Br |
| $OCH_3$ | H | Br | H |
| $OCH_3$ | Br | H | H |
| $OC_2H_5$ | Cl | H | H |
| $OC_2H_5$ | H | Cl | H |
| $OC_2H_5$ | H | H | Cl |
| $O-n-C_4H_9$ | H | I | H |
| $O-n-C_4H_9$ | I | H | H |
| $O-n-C_2H_5$ | H | F | H |
| $OC_2H_5$ | H | H | F |
| $OC_2H_5$ | $SCH_3$ | H | H |
| $OCH_3$ | H | $SCH_3$ | H |
| $O-n-C_4H_9$ | H | H | $SCH_3$ |
| $OCH_3$ | H | $SC_7H_7$ | H |
| $O-n-C_3H_7$ | $SC_7H_7$ | H | H |
| $OC_2H_5$ | H | H | $SC_7H_7$ |
| $OCH_3$ | H | $OC_2H_5$ | H |
| $OC_2H_5$ | H | $O-n-C_4H_9$ | H |
| $OC_2H_5$ | H | $OC_7H_7$ | H |
| $OC_2H_5$ | $OC_7H_7$ | H | H |

The methyl and ethyl esters in the above tabulation are converted to the corresponding n-butyl esters by the transesterification procedure of Example VIII, and to the acids, the disodium, diammonium and dipotassium salts according to the hydrolysis precedure of Example XXXIV-D.

The thioethers are converted to the corresponding sulfinyl derivatives by oxidation with hydrogen peroxide according to the precedure of Example XXII.

Benzyl ethers and benzylthio ethers are debenzylated by reaction with trifluoroacetic acid as described in Example XV to the corresponding hydroxy and thiol compounds.

EXAMPLE XXXVI

The hydroxy compounds of Example XXXV are converted to corresponding acyl derivatives by the procedure of Example XIX. The following are thus prepared:

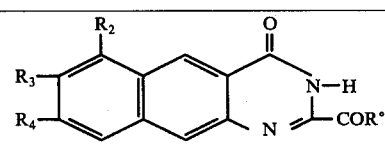

| R° | $R_2$ | $R_3$ | $R_4$ |
|---|---|---|---|
| $OCH_3$ | H | $CH_3COO$ | H |
| $O-n-C_3H_7$ | $CH_3COO$ | H | H |
| $OCH_3$ | H | $C_6H_5COO$ | H |
| $OC_2H_5$ | H | $C_6H_5COO$ | H |
| $OC_2H_5$ | HCOO | H | H |
| $O-n-C_4H_9$ | $CH_3COO$ | H | H |
| $OCH_3$ | $C_3H_7COO$ | H | H |

EXAMPLE XXXVII

Benzo[g]Quinazolin-4(3)-One-2-Carboxamides

Following the procedure of Example IX but using the appropriate 2-aminonaphthalene-3-carboxamide in place of 2-aminoquinolin-3-carboxamide, the amides corresponding to the ester products of Examples XXXIV and XXXV are prepared. The compounds have the formula:

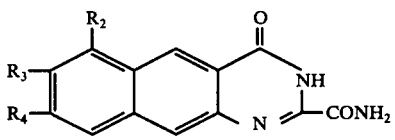

EXAMPLE XXXVIII

Benzo[g]Quinazolin-4(3H)-One-2-Hydroxamic Acids

The ester products of Example XXXIV-XXXVI are converted to the corresponding hydroxamic acids by the procedure of Example XIV. The compounds have the formula:

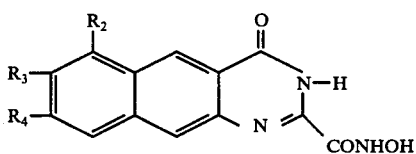

EXAMPLE XXXIX

Ethyl Pyrido[2,3-d]Pyrimidin-4(3H)-One-2-Carboxylate

A mixture of diethyl oxalate (530 mg., 3.65 millimoles) and 2-aminonicotinamide (50 mg., 3.65 millimoles) is heated to reflux overnight. The mixture is then cooled in an ice bath and the yellow solid which precipitated filtered off and recrystallized from benzene/hexane (1:1). Yield = 196 mg. (30%). M.P. 190°–192° C.

Analysis: Calcd. for $C_{10}H_9N_3O_3$: C, 54.79; H, 4.13; N, 19.17%. Found: C, 54.88; H, 4.11; N, 19.33%

Hydrolysis of the ester according to the procedure of Example XXXIV-D1 affords the acid and the disodium salt.

EXAMPLE XL

Repetition of the precedure of Example XXV but using the appropriate 2-aminonicotinamide in place of 6.7-dimethoxy-2-aminoquinoline-3-carboxamide produces the following compounds:

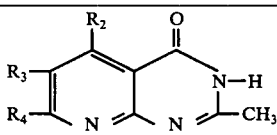

| $R_2$ | $R_3$ | $R_4$ |
|---|---|---|
| H | H | H |
| $CH_3$ | H | $CH_3$ |
| H | $OCH_3$ | $CH_3$ |
| H | $OCH_3$ | H |
| H | $t-C_4H_9$ | H |
| Cl | H | H |
| $CH_3$ | Br | $CH_3$ |
| H | $SCH_3$ | H |
| $CH_3$ | $SCH_3$ | H |
| H | $SOCH_3$* | H |
| $CH_3$ | $SOCH_3$* | H |
| $CH_3$ | $SC_7H_7$ | H |
| $CH_3$ | $SC_7H_7$ | $CH_3$ |
| $CH_3$ | $SOC_7H_7$* | H |
| $CH_3$ | $SOC_7H_7$* | $CH_3$ |
| $CH_3$ | $C_2H_5$ | $CH_3$ |

-continued

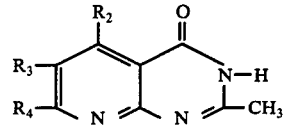

| $R_2$ | $R_3$ | $R_4$ |
|---|---|---|
| $CH_3$ | $n-C_3H_7$ | $CH_3$ |
| $CH_3$ | $n-C_4H_9$ | H |
| $CH_3$ | Cl | $CH_3$ |
| H | Cl | H |
| $CH_3$ | $C_2H_5$ | H |
| H | Cl | $CH_3$ |
| $CH_3$ | $OC_2H_5$ | H |
| $CH_3$ | $O-n-C_4H_9$ | $CH_3$ |
| $CH_3$ | $OC_7H_7$ | H |
| $OC_7H_7$ | H | H |

*Produced by oxidation of the corresponding thioethers according to the procedure of Example XXII.

The benzyl ethers and benzylthio ethers listed above are debenzylated by treatment with trifluoroacetic acid to afford the corresponding hydroxy and thiol compounds according to the procedure of Example XV.

EXAMPLE XLI

2-Ethylpyrido[2,3-d]Pyrimidin-4(3H)-Ones

Concentrated sulfuric acid (0.5 ml.) is added to a mixture of 2-aminonicotinamide (0.24 g., 0.002 mole) in propionic anhydride (10 ml.) at 60° C. and the resulting mixture stirred for one hour. It is then cooled to room temperature and poured into water (25 ml.). The aqueous mixture is stirred, made basic with 6N sodium hydroxide and stirred overnight. Upon acidification to pH 5.0 with 10% hydrochloric acid the desired product precipitates. It is filtered off and dried.

The following compounds are prepared in like manner from appropriate reactants:

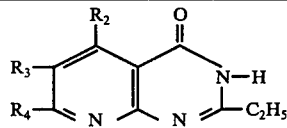

| $R_2$ | $R_3$ | $R_4$ |
|---|---|---|
| H | $OCH_3$ | $CH_3$ |
| H | $OCH_3$ | H |
| H | Cl | H |
| H | $SCH_3$ | H |
| H | $t-C_4H_9$ | H |
| $CH_3$ | Br | $CH_3$ |
| $CH_3$ | $SCH_3$ | H |
| $CH_3$ | Cl | H |
| $CH_3$ | $SOCH_3$* | H |
| H | $SOCH_3$* | H |
| H | $C_2H_5$ | H |
| H | $CH_3$ | H |
| $CH_3$ | Cl | $CH_3$ |
| $CH_3$ | $SC_7H_7$ | H |
| $CH_3$ | $SC_7H_7$ | $CH_3$ |
| $CH_3$ | $SOC_7H_7$* | H |
| H | Cl | $CH_3$ |

*Prepared by oxidation of the corresponding thio compound according to the procedure of Example XXII.

Debenzylation of the benzyl ethers and benzylthio ethers by treatment with trifluoroacetic acid according to the procedure of Example XV affords the corresponding hydroxy and thiol compounds.

EXAMPLE XLII

2-Acetylpyrimido[2,3-d]Pyrimidin-4(3H)-Ones

The products of Example XLI are oxidized by selenium dioxide substantially according to the procedure of Example XXVII to provide compounds of the formula:

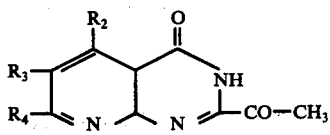

EXAMPLE XLIII

Repetition of the procedure of Example XXXV reactants produces the following compounds:

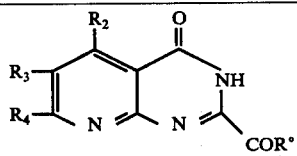

| R° | $R_2$ | $R_3$ | $R_4$ |
|---|---|---|---|
| $OC_2H_5$ | H | $CH_3$ | H |
| $O$-n-$C_3H_7$ | $CH_3$ | H | $CH_3$ |
| $OCH_3$ | H | $CH_3$ | $CH_3$ |
| $OC_2H_5$ | $CH_3$ | H | $CH_3$ |
| $OC_2H_5$ | $CH_3$ | $CH_3$ | $CH_3$ |
| $OCH_3$ | $CH_3$ | Br | $CH_3$ |
| $OC_2H_5$ | Cl | H | H |
| $O$-n-$C_4H_9$ | H | H | H |
| $OCH_3$ | H | H | $CH_3$ |
| $OC_2H_5$ | H | H | i-$C_3H_7$ |
| $OCH_3$ | H | H | i-$C_4H_9$ |
| $OC_2H_5$ | H | $OCH_3$ | $CH_3$ |
| $O$-n-$C_4H_9$ | H | $OCH_3$ | H |
| $OC_2H_5$ | $CH_3$ | H | H |
| $OC_2H_5$ | H | n-$C_3H_7$ | H |
| $OCH_3$ | H | t-$C_4H_9$ | H |
| $OC_2H_5$ | H | Cl | H |
| $O$-i-$C_3H_7$ | H | Br | H |
| $OC_2H_5$ | $CH_3$ | Cl | H |
| $OC_2H_5$ | H | Cl | $CH_3$ |
| $OCH_3$ | $CH_3$ | Cl | $CH_3$ |
| $OC_2H_5$ | H | $SCH_3$ | H |
| $OC_2H_5$ | $CH_3$ | $SCH_3$ | $CH_3$ |
| $OC_2H_5$ | $CH_3$ | $SC_7H_7$ | H |
| $OCH_3$ | $CH_3$ | $SC_7H_7$ | $CH_3$ |
| $OCH_3$ | $CH_3$ | $OC_7H_7$ | H |
| $OC_2H_5$ | $OC_7H_7$ | H | H |
| $OC_2H_5$ | $CH_3$ | $O$-n-$C_4H_9$ | $CH_3$ |
| $OC_2H_5$ | H | $SOCH_3$* | H |
| $OC_2H_5$ | $CH_3$ | $SOCH_3$* | $CH_3$ |
| $OC_2H_5$ | $CH_3$ | $SOC_7H_7$* | H |
| $OCH_3$ | $CH_3$ | $SOC_7H_7$* | $CH_3$ |

*Prepared by oxidation according to the procedure of Example XXII.

Hydrolysis of the ester by the method of Example XXIII-D produces the acid, and disodium salt derivatives. Debenzylation of benzyl ethers and benzylthio ethers in the manner of Example XV affords the corresponding hydroxy and thiol compounds.

EXAMPLE XLIV

The hydroxy and thiol compounds of Examples XL-XLIII are converted to acyloxy derivatives by the procedure of Example XIX. In this manner the formyloxy, acetoxy, butyryloxy and benzyloxy derivatives are prepared.

EXAMPLE XLIV

Pyrido[2,3-d]Pyrimidin-4(3H)-One-2-Carboxamides

The procedure of Example IX is repeated but using the appropriate 2-aminonicotinamide as reactant in place of 2-aminonaphthalene-3-carboxamide to produce the amides corresponding to the esters of Examples XXXIX and XLIII.

EXAMPLE XLVI

Pyrido[2,3-d]Pyrimidin-4(3H)-One-2-Hydroxamic Acids

The esters of Examples XXXIX and XLIII are converted by the procedure of Example XIV to hydroxamic acids of the formula:

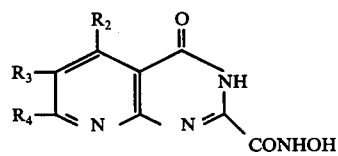

EXAMPLE XLVII

The ester products of Examples I, III-VI, VIII, X, XII, XIII, XVIII, XXVIII, XXXIV-XXXVI, XXXIX, and XLIII are converted to the corresponding acids by the procedure of Example II-D, and to the disodium, dipotassium and diammonium salts by the precedure of examples XXXIV-D and XXXIV-E.

The acids are converted to the calcium, magnesium, aluminum, triethylamine, tri-n-butylamine, piperidine, triethanolamine, diethylaminoethylamine, N,N'-dibenzylethylenediamine and pyrrolidine by reaction with an equivalent amount of the appropriate base (Ca(OH)$_2$, Mg(OH)$_2$, Al(OH)$_3$) or amine in water or ethanol followed by filtration of the salt if insoluble or by evaporation of the solvent if the salt is soluble therein.

EXAMPLE XLVIII

Injectable Preparation

One thousand grams of ethyl pyrimido[4,5-b]quinolin-4(3H)-one-2-carboxylate are intimately mixed and ground with 2500 grams of sodium ascorbate. The ground, dry mixture is placed in vials and sterilized with ethylene oxide after which the vials are sterilely stoppered. For intravenous administration, sufficient water is added to the materials in the vials to form a solution containing 5.0 mg. of active ingredient per milliliter of injectable solution.

EXAMPLE XLIX

Tablets

A tablet base is prepared by blending the following ingredients in the proportion by weight indicated:

Sucrose, U.S.P. 80.3

Tapioca Starch 13.2

Magnesium Stearate 6.5

Into this tablet base there is blended sufficient ethyl 7,8-dimethoxypyrimido[4,5-b]quinolin-4(3H)-one-2-carboxylate to provide tablets containing 20, 100 and 250 mg. of active ingredient per tablet. The compositions are each compressed into tablets, each weighing 360 mg. by mg., means.

EXAMPLE L

Capsules

A blend is prepared containing the following ingredients:

| | |
|---|---|
| Calcium carbonate, U.S.P. | 17.6 |
| Dicalcium phosphate | 18.8 |
| Magnesium trisilicate, U.S.P. | 5.2 |
| Lactose, U.S.P. | 5.2 |
| Potato starch | 5.2 |
| Magnesium stearate A | 0.8 |
| Magnesium stearate B | 0.35 |

To this blend is added sufficient ethyl 7,8-dimethoxypyrimido[4,5-b] quinolin-4(3H)-one-2-carboxylate to provide capsules containing 10, 25 and 50 mg of active ingredient per capsule. The compositions are filled into conventional hard gelatin capsules in the amount of 350 mg. per capsule.

In like manner, capsules containing 2.0 mg. and 6.0 mg. of drug, ethyl7,8-dimethoxypyrimido[4,5-b]quinoline-4-(3H)-one-2-carboxylate, and having 300 mg. of the following blends per capsule are prepared

| Ingredients | Weight mg/capsule |
|---|---|
| Drug | 2.00 |
| N-methylglucamine | 18.00 |
| Lactose, Anhydrous | 241.20 |
| Corn Starch, Anhydrous | 30.00 |
| *Talc | 8.80 |
| | 300.00 |
| Drug | 6.00 |
| N-methylglucamine | 18.00 |
| Lactose, Anhydrous | 237.20 |
| Corn Starch, Anhydrous | 30.00 |
| *Talc | 8.80 |
| | 300.00 |

*Talc added before encapsulation

EXAMPLE LI

Suspension

A suspension of pyrimido[4,5-b]quinolin-4(3H)-one-2-carboxylic acid is prepared with the following composition:

| | |
|---|---|
| Effective ingredient | 25.00 g. |
| 70% aqueous sorbitol | 741.29 g. |
| Glycerine, U.S.P. | 185.35 g. |
| Gum acacia (10% solution) | 100.00 ml. |
| Polyvinylpyrrolidone | 0.50 g. |
| Distilled water | sufficient to make 1 liter |

To this suspension, various sweeteners and flavorants are added to improve the palatability of the suspension. The suspension contains approximately 25 mg. of effective agent per milliliter.

EXAMPLE LII

In like manner, the remaining products of this invention are formulated into tablets, capsules, solutions and suspensions.

EXAMPLE LIII

Solution

A solution of ethyl 2-methylpyrimido[4,5-b]quinolin-4(3H)-one-2-carboxylate is prepared with the following composition:

| | |
|---|---|
| Effective ingredient | 6.04 grams |
| Magnesium chloride hexahydrate | 12.36 grams |
| Monoethanolamine | 8.85 ml. |
| Propylene glycol | 376.00 grams |
| Water, distilled | 94.00 ml. |

The resultant solution has a concentration of effective ingredient of 10 mg./ml. and is suitable for parenteral and, especially, for intramuscular administration.

EXAMPLE LIV

Aerosol Suspension

A mixture of ethyl 7,8-dimethoxypyrimidin[4,5-b]quinolin-4(3H)-one-2-carboxylate (antiallergy agent) and the other ingredients under (a) in the examples below are microinized to a particle size of 1 to 5 microns in a ball mill. The resulting slurry is then placed in a container equipped with a valve and propellant (b) introduced by pressure filling through the valve nozzle to a gauge pressure of approximately 35-40 pounds per square inch at 20° C.

| Suspension A | | Percent |
|---|---|---|
| (a) | Antiallergy agent | 0.25 |
| | Isopropyl myristate | 0.10 |
| | Ethanol | 26.40 |
| (b) | 60-40% mixture of 1,2-dichlorotetrafluoroethane-1-chloropentafluoroethane | 73.25 |

| Suspension B | | |
|---|---|---|
| (a) | Antiallergy agent | 0.25 |
| | Ethanol | 26.50 |
| (b) | A 60-40% mixture of 1,2-dichlorotetrafluoroethane-1-chloropentafluoroethane | 73.25 |

EXAMPLE LV

Aerosol Administration

An aqueous solution of ethyl 7,8-dimethoxypyrimido[4,5-b]quinolin-4-(3H)-one-2-carboxylic acid(Drug A, containing 3 mg. of drug per ml. of solution) is placed in a standard nebulizer such as is available from the Vaponephrine Co., Edison, N.J. The solution is sprayed under an air pressure of 6 lbs. per square inch into a closed 8 × 8 × 12 inch plastic container for 6 minutes. The container has four openings to accommodate the heads of four rats. Four rats are exposed to the drug simultaneously with only their heads coming in contact with the aerosol. Disodium cromoglycate (Drug B, 50 mg./ml.) is used as a basis for comparison. The results obtained in the PCA reaction above are tabulated below:

| Drug | Concn. | Time Interval between Drug and Challenge | % Animals Protected |
|---|---|---|---|
| A | 3 mg/ml. | 0 min. | 82 |
| A | 3 mg/ml. | 5 min. | 56 |
| B | 50 mg./ml. | 0 min. | 0 |
| B | 50 mg./ml. | 5 min. | 0 |

PREPARATION A

2-Amino-5-Alkylnicotinamides

The following 2-amino-5-alkylnicotinamides are produced from the corresponding 2-amino-5-alkylnicotinonitriles via treatment with alkaline hydrogen peroxide according to the procedure of Taylor et al., J. Org. Chem. 19, 1633–9 (1954).

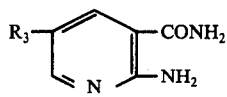

| $R_3$ |
|---|
| $C_2H_5$ |
| n-$C_3H_7$ |
| i-$C_3H_7$ |
| n-$C_4H_9$ |
| t-$C_4H_9$ |
| s-$C_4H_9$ |

PREPARATION B

2-Amino-5Halonicotinic Acids and Amides

A. 2-Amino-5-chloronicotinic acid and hydrochloride

A suspension of 40.0 g. of 2-aminonicotinic acid in 2 l. of acetic acid is stirred while chlorine gas is bubbled through the reaction mixture at a moderate rate for 1.25 hours. The resulting solution is allowed to stir at ambient temperatures for 20 hours, and is then treated with an equal volume of diethyl ether. The resulting precipitate of 2-amino-5-chloronicotinic acid hydrochloride is filtered, washed with ether and dried in vacuo at 80° C. for several hours, 51.0 g., m.p. 251° C. (dec.).

The free acid is obtained by treating a cold aqueous solution of the hydrochloric salt with sufficient ammonium hydroxide to provide a pH 5. The resulting product is filtered, washed with a small amount of acetone and dried in vacuo.

B. 2-Amino-5-bromonicotinic acid and hydrobromide

2-Aminonicotinic acid (3.6 g.) in 450 ml. of acetic acid is treated dropwise over a period of 10-15 minutes with 4 ml. of bromine in 50 ml. of acetic acid. The reaction mixture is allowed to stir at room temperature for 1.5-2 hours, and is then diluted with 2 liters of diethyl ether. The precipitate which forms, 2-amino-5-bromonicotinic acid hydrobromide, is filtered and dried, 5.6 g., m.p. 280° C. (dec.).

The free acid is liberated by adding sufficient ammonium hydroxide to an aqueous solution of the hydrobromide salt to provide a solution of pH 5. The resulting free acid is filtered from the cooled mixture and dried in vacuo.

C. 2-Amino-5-chloro-6-methylnicotinic acid hydrochloride

In a manner similar to that of Preparation B-A, 2-amino-6-methylnicotinic acid is chlorinated in acetic acid to provide the desired product.

D. 2-Amino-4-methyl-5chloronicotinic acid hydrochloride

3-Cyano-4-methylpyridine, Webb et al., J. Am. Chem. Soc., 66, 1456 (1944) is converted via the sequences of Taylor et al., J. Org. Chem., 19, 1633 (1954) to 2-amino-4-methylnicotinic acid, which under the conditions of Preparation B-A is chlorinated at the 5-position to provide the desired intermediate, 2-amino-4-methyl-5-chloronicotinic acid hydrochloride.

E. 2-Amino-4-methyl-5-bromonicotinic acid hydrobromide

In a manner analogous to that of Preparation B-B, 2-amino-4-methyl-nicotinic acid is brominated in an acetic acid solvent to provide the desired compound in good yield.

F. 2-Amino-4,6-dimethyl-5-chloronicotinic acid hydrochloride

Chlorine gas is bubbled through a solution of 1.89 g. of 2-amino4,6-dimethylnicotinic acid hydrochloride in 150 ml. of acetic acid at 36° C. for 20–25 minutes. The resulting solid is filtered, washed with diethyl ether and dried, 1.29 g., m.p. 232°–234° C. (dec.).

G. 2-Amino-5-chloro-6and 4-methylnicotinamide

Fifty grams of 2-amino-5-chloro-6-methylnicotinic acid hydrochloride is added in small portions to 185 ml. of cold (3° C.) acetyl chloride containing 80 g. of phosphorous pentachloride and the resulting reaction mixture allowed to stir at room temperature for 16 hours. The precipitate which forms is filtered, washed with 150 ml. of methylene chloride and partially dissolved in 1.2 liters of acetonitrile. While the solution of 2-amino-5-chloronicotinic acid chloride is being stirred at ambient temperatures, ammonia gas is bubbled through the slurry for 40 min. at a moderate rate. The solids are filtered and the residue, remaining after the filtrate is concentrated to dryness, is partially dissolved in acetone. The acetone suspension is filtered and the filtrate concentrated in vacuo to give 13.9 g. of the desired nicotinamide, m.p. 227°–229° C.

In like manner the remaining nicotinic acid derivatives described above are converted to the corresponding amides.

PREPARATION C

2-Amino-5-Alkylnicotinonitriles

2-Amino-4-methyl-5-ethylnicotinonitrile

To 67.0 g. (0.5 mole) of 1-methylbutylidene malononitrile (Cope, et al., J. Am. Chem. Soc., 63, 733 (1941) is added 260 ml. of acetic anhydride and 50 ml. of triethyl orthoformate and the resulting solution heated to reflux for 18 hours. The reaction mixture is concentrated under reduced pressure, and the residue is dissolved in 300 ml. of acetonitrile. Ammonia gas is bubbled through the reaction mixture at a moderate rate for 2 hours and the mixture then heated to reflux for 4 hours. The solvent is removed from the filtered mixture under reduced pressure and the residual material triturated with diethyl ether. Filtration and drying give the desired crude product.

The above reaction procedure is repeated, employing the indicated malononitrile and ortho ester starting materials to provide the corresponding substituted 2-aminonicotinonitriles.

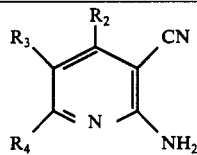

| Starting Materials | | | Product | |
|---|---|---|---|---|
| Malononitrile | ortho ester | R₄ | R₃ | R₂ |
| CH₃CH₂CH₂C(CH₃)=C(CN)₂ | CH₃C(OC₂H₅)₃ | CH₃— | C₂H₅— | CH₃— |
| CH₃(CH₂)₃CH=C(CN)₂ | CH₃C(OC₂H₅)₃ | CH₃ | n-C₃H₇— | H— |
| CH₃(CH₂)₃C(CH₃)=C(CN)₂ | CH₃C(OC₂H₅)₃ | CH₃— | n-C₃H₇— | CH₃— |
| (CH₃)₂CHCH₂C(CH₃)=C(CN)₂ | CH₃C(OC₂H₅)₃ | CH₃ | i-C₃H₇— | CH₃— |
| CH₃(CH₂)₄CH=C(CN)₂ | CH₃C(OC₂H₅)₃ | CH₃— | n-C₄H₉— | H— |
| CH₃CH(C₂H₅)CH₂C(CH₃)=C(CN)₂ | HC(OC₂H₅)₃ | H— | s-C₄H₉— | CH₃— |
| (CH₃)₃CCH₂C(CH₃)=C(CN)₂ | CH₃C(OC₂H₅)₃ | CH₃ | t-C₄H₉— | CH₃— |

The nitriles are converted to the corresponding amides by the procedure of Taylor et al., J. Org. Chem. 19, 1633-9 (1954).

PREPARATION D

2-Amino-4-Substituted-quinoline-3-Carboxamides

The appropriate substituted 2-aminobenzophenone or alkyl-(2-aminophenyl)ketone of the formula

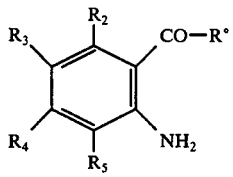

wherein the R variables have the values given below, and malononitrile are mixed together in pyridine in a 1:2 molar ratio and heated under reflux for 24 hours. Sufficient pyridine is used to achieve solution of the reactants. The mixture is then cooled an concentrated in vacuo. The precipitate is collected, washed with ethanol and recrystallized from ethanol.

The thus-obtained nitrile is hydrolyzed by heating in excess of 95% sulfuric acid for three hours on a steam bath. The mixture is then poured into a large volume of ice water and allowed to stand overnight. The aqueous mixture is filtered if necessary and the filtrate made alkaline (pH 11-11.5) with 5N sodium hydroxide. The amide product precipitates and is recovered by filtration. It is washed with water and dried.

The following compounds are thus prepared:

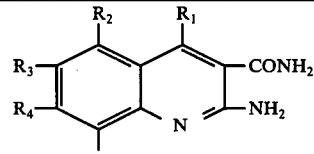

| R₂ | R₃ | R₄ | R₅ | R₁ |
|---|---|---|---|---|
| H | H | H | Cl | C₆H₅ |
| H | Cl | H | H | C₆H₅ |
| H | Br | H | H | C₆H₅ |
| H | F | H | H | C₆H₅ |
| H | H | CH₃ | H | C₆H₅ |
| H | Cl | Cl | H | C₆H₅ |
| H | CH₃ | CH₃ | H | C₆H₅ |
| H | OCH₃ | H | H | C₆H₅ |
| H | H | OCH₃ | H | C₆H₅ |
| H | CH₃ | Cl | H | C₆H₅ |
| H | H | CH₃ | CH₃ | C₆H₅ |

-continued

| R₂ | R₃ | R₄ | R₅ | R₁ |
|---|---|---|---|---|
| H | Br | H | H | C₂H₅ |
| H | H | Cl | H | C₂H₅ |
| H | OCH₃ | H | H | C₂H₅ |
| H | OCH₃ | OCH₃ | H | C₂H₅ |
| H | H | H | H | CH₃ |
| H | H | H | H | C₂H₅ |
| H | H | H | H | n-C₃H₇ |
| H | H | H | H | n-C₄H₉ |
| H | H | Br | H | CH₃ |
| H | Cl | H | H | CH₃ |
| H | H | H | OCH₃ | CH₃ |
| H | OCH₃ | OCH₃ | H | CH₃ |
| H | Cl | CH₃ | H | CH₃ |
| H | H | OCH₃ | OCH₃ | CH₃ |
| H | H | OC₂H₅ | OC₂H₅ | CH₃ |
| H | CH₃ | CH₃ | H | CH₃ |
| H | H | I | H | CH₃ |
| H | Cl | H | H | n-C₃H₇ |
| H | Cl | H | H | n-C₄H₉ |
| CH₃ | CH₃ | CH₃ | OCH₃ | CH₃ |
| H | OCH₃ | H | H | CH₃ |

PREPARATION E

α-Cyano-β-(2-Nitro-MethylthiophenylAcrylamides

The following compounds are prepared by reaction of the appropriate α-Cyano-β-(2-nitro-chlorophenyl)acrylamide with sodium methylmercaptide or sodibenzylmercaptide according to the procedure of Example XXI-A.

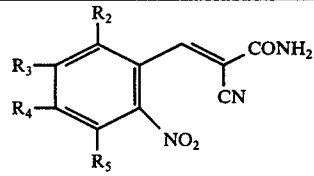

| R₂ | R₃ | R₄ | R₅ |
|---|---|---|---|
| CH₃S | H | H | H |
| H | CH₃S | CH₃S | H |
| CH₃S | H | H | CH₃S |
| H | H | CH₃S | H |
| C₆H₅S | H | H | H |
| C₆H₅S | H | H | C₆H₅S |
| H | C₆H₅S | C₆H₅S | H |
| H | C₆H₅S | H | H |

PREPARATION F

Reaction of the appropriate chloro substituted 2-aminonaphthalene-3-carboxamide or the appropriate chlorosubstituted 2-aminonicotinamide with sodium methylmercaptide, sodium benzylmercaptide, sodium benzylate or the appropriate sodium alcoholate according to the procedure of Example XXI-A affods the following compounds:

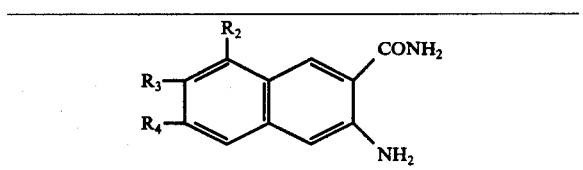

| $R_2$ | $R_3$ | $R_4$ | $R_2$ | $R_3$ | $R_4$ |
|---|---|---|---|---|---|
| $SCH_3$ | H | H | H | $OC_2H_5$ | H |
| H | $SCH_3$ | H | H | $O-n-C_4H_9$ | H |
| H | H | $SCH_3$ | H | $OC_7H_7$ | H |
| $SC_7H_7$ | H | H | $OC_7H_7$ | H | H |
| H | $SC_7H_7$ | H | | | |
| H | H | $SC_7H_7$ | | | |

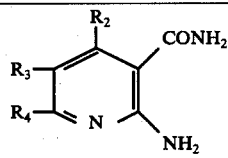

| $R_2$ | $R_3$ | $R_4$ | $R_2$ | $R_3$ | $R_4$ |
|---|---|---|---|---|---|
| H | $SCH_3$ | H | $CH_3$ | $OC_2H_5$ | H |
| $CH_3$ | $SCH_3$ | H | $CH_3$ | $O-n-C_4H_9$ | $CH_3$ |
| $CH_3$ | $SCH_3$ | $CH_3$ | $CH_3$ | $OC_7H_7$ | H |
| $CH_3$ | $SC_7H_7$ | H | | $OC_7H_7$ | H |
| $CH_3$ | $SC_7H_7$ | $CH_3$ | 67 2 | | |
| H | 71 | | | | |

PREPARATION G

Benzyl Ethers of Hydroxy Substituted Benzaldehydes

A mixture of the appropriate hydroxy substituted benzaldehyde (0.66 mole), absolute ethanol (450 ml.), anhydrous potassium carbonate (91.5g.) and freshly distilled benzyl chloride (95.6g., 0.76 mole) is refluxed for 2–3 days. The reaction mixture is filtered to remove the salts and the filtrate concentrated under reduced pressure. The oily residue is cooled and the resulting solid is recrystallized from an appropriate solvent such as ethanol.

In this manner, the following benzyl ethers are prepared:

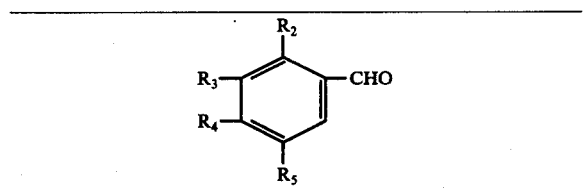

| $R_2$ | $R_3$ | $R_4$ | $R_5$ |
|---|---|---|---|
| H | H | $OC_7H_7$ | H |
| $OC_7H_7$ | $OCH_3$ | H | H |
| H | $OC_7H_7$ | $OC_7H_7$ | H |
| $OC_7H_7$ | H | H | H |
| $OC_7H_7$ | Br | H | Br |

-continued

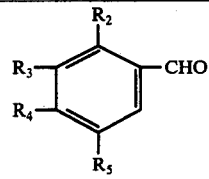

| $R_2$ | $R_3$ | $R_4$ | $R_5$ |
|---|---|---|---|
| H | $OCH_3$ | $OC_7H_7$ | Br |
| H | $OCH_3$ | $OC_7H_7$ | $OCH_3$ |
| $OC_7H_7$ | $OCH_3$ | $OCH_3$ | H |
| H | Br | H | $OC_7H_7$ |
| H | H | H | $OC_7H_7$ |
| $C_2H_5$ | $OC_7H_7$ | H | H |
| $C_2H_5$ | H | $OC_7H_7$ | H |
| H | $OC_7H_7$ | $OC_2H_5$ | H |
| H | $OC_2H_5$ | $OC_7H_7$ | H |
| H | F | $OC_7H_7$ | H |
| H | Br | $OC_7H_7$ | H |
| H | Cl | $OC_7H_7$ | H |
| H | $OC_7H_7$ | H | $OCH_3$ |
| $CH_3$ | $CH_3$ | $OC_7H_7$ | $CH_3$ |
| $CH_3$ | $OC_7H_7$ | $CH_3$ | $CH_3$ |
| H | $i-C_3H_7$ | $OC_7H_7$ | $i-C_3H_7$ |

PREPARATION H

5-Benzyloxy-4-Methoxy-2-Nitrobenzaldehyde

To concentrated nitric acid (200 ml.) maintained at 0° C. is added 3-benzyloxy-4-methoxybenzaldehyde (48 g., 0.198 mole) over a 30 minute period with stirring. When addition is complete, the temperature is allowed to rise to 15° C. and stirring continued for another 30 minutes. The mixture is then added to ice-water and the yellow precipitate collected by filtration and dried. Yield = 52.8g. (94%); m.p. 131°–132° C.

In like manner, the products of Preparation G are nitrated to their 2-nitro derivatives. In those cases wherein a mixture of products is obtained the products are separated by chromatography on an acid-washed silica using an appropriate solvent such as benzene or chloroform.

What is claimed is:

1. The method of controlling allergic symptoms in a mammalian subject which comprises administering to the subject an allergy symptom-controlling amount of a compound selected from the group consisting of those having the formula

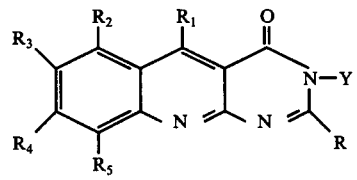

and the pharmaceutically acceptable cation salts thereof wherein R is selected from the group consisting of methyl, ethyl, acetyl and Cor° wherein R° is selected from the group consisting of hydroxy, alkoxy having 1 to 4 carbon atoms, hydroxyalkoxy having 2 to 4 carbon atoms, amino and hydroxyamino;

Y is selected from the group consisting of (a) hydrogen and (b) alkyl having 1 to 4 carbon atoms, carbalkoxyalkyl having 2 to 5 carbon atoms in the carbalkoxy moiety and 1 to 4 carbon atoms in the alkyl moiety, carboxyalkyl having 1 to 4 carbon atoms in the alkyl moiety, —(CH$_2$)$_m$—O—CO—C$_6$H$_5$ and —(CH$_2$)$_m$—O—CO—alkyl having 1 to 4 carbon atoms in the alkyl moiety; with the proviso that when R is COR° wherein R° is amino or hydroxyamino, Y is hydrogen; m is an integer from 2 up to and including 4;

R$_1$ is selected from the group consisting of hydrogen, alkyl having 1 to 4 carbon atoms and phenyl;

each of R$_2$, R$_3$, R$_4$ and R$_5$ is selected from the group consisting of hydrogen, alkyl having 1 to 4 carbon atoms, alkoxy having 1 to 4 carbon atoms, halo, benzyloxy, hydroxy, thiol, alkanoyloxy having 1 to 4 carbon atoms, benzylthio, benzoyloxy, benzylsulfinyl, methylthio and methylsulfinyl and R$_2$ and R$_3$ and R$_3$ and R$_4$ when taken together are selected from the group consisting of methylenedioxy and ethylenedioxy.

2. The method of claim 1 wherein each of R$_1$, R$_2$, R$_5$, and Y is hydrogen; each of R$_3$ and R$_4$ is alkoxy, and R is methyl.

3. The method of claim 1 wherein each of R$_1$, R$_2$, R$_5$, and Y is hydrogen; R is COR° wherein R° is alkoxy; one of R$_3$ and R$_4$ is hydroxy and the other is alkoxy.

4. The method of claim 1 wherein each of R$_1$, R$_2$, R$_5$, and Y is hydrogen; one of R$_3$ and R$_4$ is hydroxy and the other is alkoxy; and R is COR° wherein R° is hydroxy.

5. The method of claim 1 wherein each of R$_1$, R$_2$, R$_5$, and Y is hydrogen; R is COR° wherein R° is hydroxy; and each of R$_3$ and R$_4$ is alkoxy.

6. The method of claim 2 wherein each of R$_3$ and R$_4$ is methoxy.

7. The method of claim 3 wherein R° is n-butoxy; R$_3$ is hydroxy; and R$_4$ is methoxy.

8. The method of claim 4 wherein R$_3$ is hydroxy; and R$_4$ is methoxy.

9. The method of claim 5 wherein each of R$_3$ and R$_4$ is methoxy.

10. A pharmaceutical composition active as an antiallergy agent comprising a pharmaceutically acceptable carrier and a compound selected from the group consisting of those having the formula

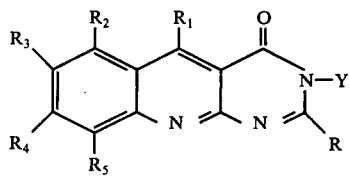

and the pharmaceutically acceptable cation salts thereof wherein R is selected from the group consisting of methyl, ethyl, acetyl and COR° wherein R° is selected from the group consisting of hydroxy, alkoxy having 1 to 4 carbon atoms, hydroxyalkoxy having 2 to 4 carbon atoms, amino and hydroxyamino;

Y is selected from the group consisting of (a) hydrogen and (b) alkyl having 1 to 4 carbon atoms, carbalkoxyalkyl having 2 to 5 carbon atoms in the carbalkoxy moiety and 1 to 4 carbon atoms in the alkyl moiety, carboxyalkyl having 1 to 4 carbon atoms in the alkyl moiety, —(CH$_2$)$_m$—O—CO—C$_6$H$_5$ and —(CH$_2$)$_m$—O—CO—alkyl having 1 to 4 carbon atoms in the alkyl moiety; with the proviso that when R is COR° wherein R° is amino or hydroxyamino, Y is hydrogen; m is an integer from 2 up to and including 4;

R$_1$ is selected from the group consisting of hydrogen, alkyl having 1 to 4 carbon atoms and phenyl;

each of R$_2$, R$_3$, R$_4$ and R$_5$ is selected from the group consisting of hydrogen, alkyl having 1 to 4 carbon atoms, alkoxy having 1 to 4 carbon atoms, halo, benzyloxy, hydroxy, thiol, alkanoyloxy having 1 to 4 carbon atoms, benzylthio, benzoyloxy, benzylsulfinyl, methythio and methylsulfinyl;

R$_2$ and R$_3$, and R$_3$ and R$_4$ when taken together are selected from the group consisting of methylenedioxy and ethylenedioxy;

and a pharamaceutical carrier, said compound of said formula or the pharmaceutically acceptable cation salt thereof being present in an amount of from 0.5 to about 95% by weight of said carrier.

11. A composition according to claim 10 wherein each of R$_1$, R$_2$, R$_5$ and Y is hydrogen; each of R$_3$ and R$_4$ is methoxy; and R is methyl.

12. A composition according to claim 10 wherein each of R$_1$, R$_2$, Y and R$_5$ is hydrogen; each of R$_3$ and R$_4$ is methoxy and R is COR° wherein R° is ethoxy.

13. A composition according to claim 10 wherein each of R$_1$, R$_2$, R$_5$, and Y is hydrogen; R$_3$ is hydroxy; R$_4$ is methoxy; and R is COR° wherein R° is n-butoxy.

14. A pharmaceutical composition as claimed in claim 10 in a form suitable for administration by inhalation.

15. A pharmaceutical composition as claimed in claim 10 comprising a solution or suspension of the antiallergy agent in water.

16. A pharmaceutical composition as claimed in claim 10 comprising a suspension of the antiallergy agent in a liquefied propellant.

17. A pharmaceutical composition as claimed in claim 10 comprising the solid antiallergy agent and a solid diluent.

* * * * *

UNITED STATES PATENT AND TRADEMARK OFFICE
CERTIFICATE OF CORRECTION

PATENT NO. : 4,044,134
DATED : August 23, 1977
INVENTOR(S) : Thomas H. Althuis et al It is certified that error appears in the above-identified patent and that said Letters Patent are hereby corrected as shown below:

Col. 5, line 24, that portion of the formula reading

Col. 9, line 57, "comprises" should read -- routes comprises --.

Col. 10, line 64, "20%" should read -- 5% to about 20% --.

Col. 23, line 53, "$4,5-b]$" should read -- [4,5-b] --.

Col. 27, line 20, "Yield = C." should read -- 219°C. --.

Col. 28, lines 53-59; Col. 29, lines 2-8; and Col. 30, lines 2-8, each occurrence, that portion of the formula reading

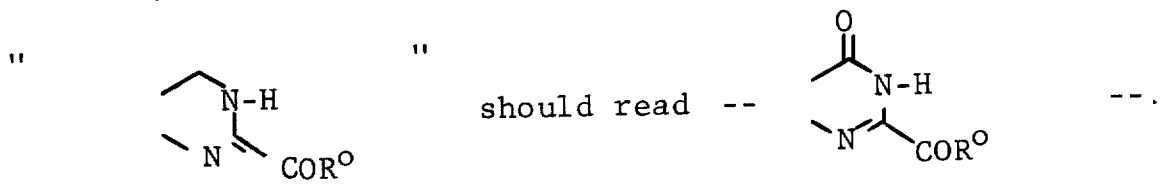

UNITED STATES PATENT AND TRADEMARK OFFICE
CERTIFICATE OF CORRECTION

PATENT NO. : 4,044,134
DATED : August 23, 1977
INVENTOR(S) : Thomas H. Althuis et al It is certified that error appears in the above-identified patent and that said Letters Patent are hereby corrected as shown below:

Col. 31, lines 5-10, that portion of the formula reading

Col. 36, line 7, "4(SH)-One" should read -- 4(3H)-One --.

Col. 43, line 66, "0.135" should read -- 0.133 --.

Col. 50, line 68, "by mg.," should read -- , by conventional

Col. 57, line 34, "CH₃ 63 7 65" should read -- CH₃ -- and delete "67 2"; line 36, delete "H" and "71".

Signed and Sealed this

Fifteenth Day of August 1978

[SEAL]

Attest:

RUTH C. MASON
Attesting Officer

DONALD W. BANNER
Commissioner of Patents and Trademarks